United States Patent
Minomi et al.

(10) Patent No.: US 10,047,110 B2
(45) Date of Patent: *Aug. 14, 2018

(54) RNA AGENTS FOR GST-PI GENE MODULATION

(71) Applicant: Nitto Denko Corporation, Osaka (JP)

(72) Inventors: Kenjirou Minomi, Osaka (JP); Hirokazu Takahashi, Osaka (JP); Erika Terada, Osaka (JP); Jens Harborth, Carlsbad, CA (US); Jun Zhang, San Diego, CA (US); Mohammad Ahmadian, Carlsbad, CA (US); Wenbin Ying, San Diego, CA (US)

(73) Assignee: Nitto Denko Corporation, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/979,567

(22) Filed: Dec. 28, 2015

(65) Prior Publication Data

US 2016/0208254 A1 Jul. 21, 2016

Related U.S. Application Data

(60) Provisional application No. 62/266,664, filed on Dec. 13, 2015, provisional application No. 62/184,239, filed on Jun. 24, 2015.

(30) Foreign Application Priority Data

Dec. 26, 2014 (JP) .................. 2014-266198

(51) Int. Cl.
| | | |
|---|---|---|
| C12N 15/113 | (2010.01) | |
| C07H 21/02 | (2006.01) | |
| C07F 9/6533 | (2006.01) | |
| C12Q 1/02 | (2006.01) | |
| G01N 33/58 | (2006.01) | |
| A61K 31/713 | (2006.01) | |

(52) U.S. Cl.
CPC .......... *C07F 9/6533* (2013.01); *C12N 15/113* (2013.01); *C12N 15/1135* (2013.01); *C12N 15/1137* (2013.01); *C12Q 1/02* (2013.01); *G01N 33/582* (2013.01); *H05K 999/99* (2013.01); *A61K 31/713* (2013.01); *C12N 2310/14* (2013.01); *C12N 2310/322* (2013.01); *C12N 2310/344* (2013.01); *C12N 2310/3515* (2013.01); *C12N 2310/531* (2013.01); *C12N 2320/30* (2013.01); *C12N 2320/32* (2013.01); *C12N 2320/35* (2013.01); *C12N 2320/53* (2013.01)

(58) Field of Classification Search
None
See application file for complete search history.

(56) References Cited

U.S. PATENT DOCUMENTS

| | | |
|---|---|---|
| 5,968,737 A | 10/1999 | Ali-Osman |
| 8,067,390 B2 | 11/2011 | Merritt |
| 8,367,628 B2 | 2/2013 | Goodwin |
| 8,664,376 B2 | 3/2014 | Niitsu |
| 8,686,052 B2 | 4/2014 | Niitsu |
| 8,710,209 B2 | 4/2014 | Jin |
| 8,741,867 B2 | 6/2014 | Niitsu |
| 8,895,717 B2 | 11/2014 | Sood |
| 9,151,758 B2 | 10/2015 | Zetter |
| 9,206,424 B2 | 12/2015 | Jin |
| 2004/0219600 A1 | 11/2004 | Williams |
| 2005/0255487 A1 | 11/2005 | Khvorova |
| 2007/0083334 A1 | 4/2007 | Mintz |
| 2007/0083945 A1 | 4/2007 | Byrum |
| 2013/0028885 A1 | 1/2013 | Zetter |
| 2013/0052160 A1 | 2/2013 | Zitvogel |
| 2013/0053270 A1 | 2/2013 | Gill |
| 2014/0134158 A1 | 5/2014 | Bardelli |
| 2014/0303237 A1 | 10/2014 | Shapiro et al. |
| 2014/0315975 A1 | 10/2014 | Niitsu |
| 2014/0315976 A1 | 10/2014 | Brahmbhatt et al. |
| 2016/0187319 A1 | 6/2016 | Tanaka |

FOREIGN PATENT DOCUMENTS

| | | |
|---|---|---|
| EP | 2724729 A1 | 4/2014 |
| WO | 1998021359 A1 | 5/1998 |
| WO | 2004094636 A1 | 11/2004 |
| WO | 2007061922 A2 | 5/2007 |

(Continued)

OTHER PUBLICATIONS

Futreal, A Census of Human Cancer Genes, Nature Reviews Cancer 2004, vol. 4, pp. 177-183.
Takahashi et al., Gan to Kagaku Ryoho. 1994; 21 (7): 945-51, English summary p. 951.
Ban et al., Cancer Res. 1996; 56 (15): 3577-82, Transfection of Glutathione S-Transferase (GST)-n' Antisense Complementary DNA Increases the Sensitivity of a Colon Cancer Cell Line to Adriamycin, Cisplatin, Melphalan, and Etoposide.
Nakajima et al., J Pharmacol Exp Ther. 2003; 306 (3): 861-9, Reversal of Multiple Drug Resistance in Cholangiocarcinoma by the Glutathione S-Transferase-Pi-Specific Inhibitor O1-Hexadecyl-gamma-glutamyl-S-benzylcysteinyl-D-phenylglycine Ethylester.
Hokaiwado et al., Carcinogenesis. 2008; 29 (6): 1134-8, Glutathione S-transferase Pi mediates proliferation of androgen-independent prostate cancer cells.

(Continued)

*Primary Examiner* — Richard A Schnizer
(74) *Attorney, Agent, or Firm* — Eckman Law Group

(57) ABSTRACT

This invention provides compounds, compositions and methods for modulating the expression of human GST-π using RNA interference. The RNA interference molecules can be used in methods for preventing or treating diseases such as malignant tumor. A nucleic acid molecule can have a) a polynucleotide sense strand and a polynucleotide antisense strand; b) each strand of the molecule being from 15 to 30 nucleotides in length; c) a contiguous region of from 15 to 30 nucleotides of the antisense strand being complementary to a sequence of an mRNA encoding GST-π; and d) at least a portion of the sense strand can be complementary to at least a portion of the antisense strand, and the molecule has a duplex region of from 15 to 30 nucleotides in length.

10 Claims, 4 Drawing Sheets

(56) References Cited

FOREIGN PATENT DOCUMENTS

| WO | 2012176282 A1 | 12/2012 |
|---|---|---|
| WO | 2013192364 A1 | 12/2013 |
| WO | 2014098210 A1 | 6/2014 |

OTHER PUBLICATIONS

Adler et.al, EMBO J. 1999, 18, 1321-1334, Regulation of JNK signaling by GSTp.
Townsend, et al, J. Biol. Chem. 2009, 284, 436-445, Novel Role for Glutathione S-Transferase Pi Regulator of Protein S-Glutathionylation Following Oxidative and Nitrosative Stress.
Yin et.al, Cancer Res. 2000 60, 4053-4057, Glutathione S-Transferase p Elicits Protection against H2O2-induced Cell Death via Coordinated Regulation of Stress Kinases.
Nishita et al., AACR 102nd Annual Meeting, Abstract No. 1065, 2011, Regulation of autophagy and MAPK signaling by glutathione S-transferase Pi in KRAS mutated cancer cells.
Love, Lipid-like materials for low-dose, in vivo gene silencing, Proc Natl Acad Sci U S A., 2010, vol. 107(5), pp. 1864-1869.
Xue, Small RNA combination therapy for lung cancer, Proc Natl Acad Sci U S A, 2014, vol. 111(34), pp. E3553-E3561.
Xu, Enhancing tumor cell response to chemotherapy through nanoparticle-mediated codelivery of siRNA and cisplatin prodrug, Proc Natl Acad Sci U S A, 2013, vol. 110, No. 46, pp. 18638-18643.
Ui-Tei, Functional dissection of siRNA sequence by systematic DNA substitution: modified siRNA with a DNA seed arm is a powerful tool for mammalian gene silencing with significantly reduced off-target effect, Nucleic Acids Res., 2008, vol. 36(7), pp. 2136-2151.
Niitsu, Serum Glutathione-S-Transferase-rr as a Tumor Marker for Gastrointestinal Malignancies, Cancer, Jan. 15, 1989, vol. 63, pp. 317-323.
Hirata, Significance of Glutathione S-Transferase-Pi as a Tumor Marker in Patients with Oral Cancer, Cancer, Nov. 15, 1992, vol. 70, No. 10, pp. 2381-2387.
Hida, Serum Glutathione S-Transferase-Pi Level as a Tumor Marker for Non-Small Cell Lung Cancer, Cancer, Mar. 1, 1994, vol. 73, No. 5, pp. 1377-1382.
Ban, Transfection of Glutathione S-Transferase (GST)-Pi Antisense Complementary DNA Increases the Sensitivity of a Colon Cancer Cell Line to Adriamycin, Cisplatin, Melphalan, and Etoposide, Cancer Research, Aug. 1, 1996, vol. 56, 3577-3582.
Morgan, Tumor Efficacy and Bone Marrow-sparing Properties of TER286, a Cytotoxin Activated by Glutathione S-Transferase, Cancer Research, Jun. 15. 1998, vol. 58, pp. 2568-2575.
Niitsu, A proof of glutathione S-transferase-pi-related multidrug resistance by transfer of antisense gene to cancer cells and sense gene to bone marrow stem cell, Chemico-Biological Interactions, 1998, vol. 111-112, pp. 325-332.
Miyanishi, Glutathione S-Transferase-pi Overexpression is Closely Associated With K-ras Mutation During Human Colon Carcinogenesis, Gastroenterology, 2001, vol. 121, pp. 865-874.
Matsunaga, C(H)OP refractory chronic lymphocytic leukemia patients in whom salvage chemotherapy chosen by evaluating multiple chemotherapeutic drug-resistant factors was remarkably effective, Int J Clin Oncol, 2003, vol. 8, pp. 326-331.
Hayashi, Suppressive effect of sulindac on branch duct-intraductal papillary mucinous neoplasms, J Gastroenterol, 2009, vol. 44, pp. 964-975.
Morse, The role of glutathione S-transferase P1-1 in colorectal cancer: friend or foe?, Gastroenterology, 2001, vol. 121(4), pp. 1010-1013.
Steckel, Determination of synthetic lethal interactions in KRAS oncogene-dependent cancer cells reveals novel therapeutic targeting strategies, Cell Res., 2012, vol. 22(8), pp. 1227-1245.
Collins, KRAS as a key oncogene and therapeutic target in pancreatic cancer, Front Physiol., 2013, vol. 4, Article 407, pp. 1-8.
Ruan, Analysis of EGFR signaling pathway in nasopharyngeal carcinoma cells by quantitative phosphoproteomics, Proteome Science, Jun. 28, 2011, vol. 9, pp. 1-11.
Singhal, 1,3-Bis(3,5-dichlorophenyl) urea compound 'COH-SR4' inhibits proliferation and activates apoptosis in melanoma, Biochemical Pharmacology, Dec. 1, 2012, vol. 84, Iss. 11, pp. 1419-1427.
Hokaiwado, Glutathione S-transferase Pi mediates proliferation of androgen-independent prostate cancer cells, Carcinogenesis, Apr. 15, 2008, vol. 29, pp. 1134-1138.
AC114115, GenBank Accession No. AC114115, Rattus norvegicus clone CH230-2808, Working Draft Sequence, 6 unordered pieces, May 13, 2003 [online]. [Retrieved on Apr. 30, 2016). Retrieved from the Internet <URL: http://www.ncbi.nlm.nih.gov/nuccore/AC114115>.
JU528663, GenBank Accession No. JU528663, TSA: Ctenomys sociabilis 330326.Ctso mRNA sequence, Oct. 10, 2012 [online]. [Retrieved on Apr. 30, 2016). Retrieved from the Internet <URL: http://www.ncbi.nlm.nih.gov/nuccore/JU528663>.
GO761423, GenBank Accession No. G0761423, 0010260TNA004657HT OTNA Ovis aries cDNA 5-, mRNA sequence May 8, 2009 [online]. [Retrieved on Apr. 30, 2016]. Retrieved from the Internet <URL: http://www.ncbi.nlm.nih.gov/nucest/G0761423>.
GO786145, GenBank Accession No. G0786145, 0009200TNA002813HT OTNA Ovis aries cDNA 5-,.mRNA sequence May 8, 2009 [online). [Retrieved on Apr. 30, 2016]. Retrieved from the internet <URL: http://www.ncbi.nlm.nih.gov/nucest/G0786145>.
AC230665, GenBank Accession No. AC230665, Bos taurus clone CH240-502B15, Jul. 10, 2008 [online]. [Retrieved on May 1, 2016]. Retrieved from the internet <URL:http://www.ncbi.nlm.nih.gov/nuccore/AC230665>.
AC230574, GenBank Accession No. AC230574, Bos taurus clone CH240-504M17, Jul. 10, 2008 [online]. [Retrieved on May 1, 2016]. Retrieved from the internet <URL:http://www.ncbi.nlm.nih.gov/nuccore/AC230574>.
BV207757, GenBank Accession No. BV207757, sqnm2244B3 Human DNA (Sequenom) Homo sapiens STS genomic, Oct. 17, 2009 [online]. [Retrieved on May 1, 2016). Retrieved from the internet <URL: http://www.ncbi.nlm.nih.gov/nuccore/BV207757>.
AW374759, GenBank Accession No. AW374759, MR1-CT005B-291199-003-a05 CT0058 Homo sapiens cDNA. mRNA sequence, Jan. 9, 2011 [online]. (Retrieved on May 1, 2016). Retrieved from the internet <URL: http://www.ncbi.nlm.nih.gov/nucest/6B79413/>.
Wagner, In Situ Evidence of KRAS Amplification and Association With Increased p21 Levels in Non-Small Cell Lung Carcinoma, 2009, Am J Clin Pathol, vol. 132, pp. 500-505.
https://cansar.icr.ac.uk/cansar/cell-lines/A549/mutations/ retrieved from the web on Jun. 20, 2016.
Valtorta, KRAS gene amplification in colorectal cancer and impact on response to EGFR-targeted therapy, 2013, Int. J. Cancer, vol. 133, pp. 1259-1266.
Birkeland, KRAS gene amplification and overexpression but not mutation associates with aggressive and metastatic endometrial cancer, 2012, British Journal of Cancer, vol. 107, pp. 1997-2004.
Muller, Thiazolides inhibit growth and induce glutathione-S-transferase Pi (GSTP1)-dependent cell death in human aolon cancer cells, 2008, Int. J. Cancer, vol. 123, pp. 1797-1806.
Sawers, Glutathione S-transferase Pi (GSTP1) directly influences platinum drug chemosensitivity in ovarian tumour cell lines, British Journal of Cancer, 2014, vol. 111, pp. 1150-1158.

SEQ ID NO:1

```
TGGGAAAGAGGGAAAGGCTTCCCCGGCCAGCTGCGCGGCGACTCCGGGGACTCCAGGGCGCCCCTCTGCG
GCCGACGCCCGGGGTGCAGCGGCCGCCGGGGCTGGGGCCGGCGGGAGTCCGCGGGACCCTCCAGAAGAGC
GGCCGGCGCCGTGACTCAGCACTGGGGCGGAGCGGGGCGGGACCACCCTTATAAGGCTCGGAGGCCGCGA
GGCCTTCGCTGGAGTTTCGCCGCCGCAGTCTTCGCCACCATGCCGCCCTACACCGTGGTCTATTTCCCAG
TTCGAGGCCGCTGCGCGGCCCTGCGCATGCTGCTGGCAGATCAGGGCCAGAGCTGGAAGGAGGAGGTGGT
GACCGTGGAGACGTGGCAGGAGGGCTCACTCAAAGCCTCCTGCCTATACGGGCAGCTCCCCAAGTTCCAG
GACGGAGACCTCACCCTGTACCAGTCCAATACCATCCTGCGTCACCTGGGCCGCACCCTTGGGCTCTATG
GGAAGGACCAGCAGGAGGCAGCCCTGGTGGACATGGTGAATGACGGCGTGGAGGACCTCCGCTGCAAATA
CATCTCCCTCATCTACACCAACTATGAGGCGGGCAAGGATGACTATGTGAAGGCACTGCCCGGGCAACTG
AAGCCTTTTGAGACCCTGCTGTCCCAGAACCAGGGAGGCAAGACCTTCATTGTGGGAGACCAGATCTCCT
TCGCTGACTACAACCTGCTGGACTTGCTGCTGATCCATGAGGTCCTAGCCCCTGGCTGCCTGGATGCGTT
CCCCCTGCTCTCAGCATATGTGGGGCGCCTCAGTGCCCGGCCCAAGCTCAAGGCCTTCCTGGCCTCCCCT
GAGTACGTGAACCTCCCCATCAATGGCAACGGGAAACAGTGAGGGTTGGGGGGACTCTGAGCGGGAGGCA
GAGTTTGCCTTCCTTTCTCCAGGACCAATAAAATTTCTAAGAGAGCTAAAAAAAAAAAAAAAAAAAAAAA
AAAAAA
```

FIG. 1

SEQUENCE LISTING

```
<160> NUMBER OF SEQ ID NOS: 1345

<210> SEQ ID NO 1
<211> LENGTH: 986
<212> TYPE: DNA
<213> ORGANISM: Homo sapiens

<400> SEQUENCE: 1
tgggaaagag ggaaaggctt ccccggccag ctgcgcggcg actccgggga ctccagggcg        60 ccctctgcg gccgacgccc ggggtgcagc ggccgccggg gctggggccg gcgggagtcc       120
gcgggaccct ccagaagagc ggccggcgcc gtgactcagc actgggcgg agcggggcgg       180 gaccaccctt ataaggctcg gaggccgcga ggccttcgct ggagtttcgc cgccgcagtc       240
ttcgccacca tgccgcccta caccgtggtc tatttcccag ttcgaggccg ctgcgcggcc       300
ctgcgcatgc tgctggcaga tcagggccag agctggaagg aggaggtggt gaccgtggag       360
acgtggcagg agggctcact caaagcctcc tgcctatacg ggcagctccc caagttccag       420
gacggagacc tcaccctgta ccagtccaat accatcctgc gtcacctggg ccgcacccTT       480
gggctctatg ggaaggacca gcaggaggca gccctggtgg acatggtgaa tgacggcgtg       540
gaggacctcc gctgcaaata catctccctc atctacacca actatgaggc gggcaaggat       600
gactatgtga aggcactgcc cgggcaactg aagccttttg agaccctgct gtcccagaac       660
cagggaggca agaccttcat tgtgggagac cagatctcct tcgctgacta caacctgctg       720
gacttgctgc tgatccatga ggtcctagcc cctggctgcc tggatgcgtt ccccctgctc       780
tcagcatatg tggggcgcct cagtgcccgg cccaagctca aggccttcct ggcctcccct       840
gagtacgtga acctccccat caatggcaac gggaaacagt gagggttggg gggactctga       900
```
gcgggaggca gagtttgcct tcctttctcc aggaccaata aaatttctaa gagagctaaa    960
aaaaaaaaaa aaaaaaaaaa aaaaaa                                         986

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2
gccgcagucu ucgccaccat t                                              21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 3
ccgcagucuu cgccaccaut t                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4
cgcagucuuc gccaccaugt t                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 5
gcagucuucg ccaccaugct t                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

```
                    Synthetic oligonucleotide

<400> SEQUENCE: 6
cagucuucgc caccaugcct t                                          21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 7
agucuucgcc accaugccgt t                                          21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 8
gucuucgcca ccaugccgct t                                          21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 9
ucuucgccac caugccgcct t                                          21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 10
cuucgccacc augccgccct t                                          21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

<223> OTHER INFORMATION: Description of Combined DNA/RNA Molecule:
      Synthetic oligonucleotide

<400> SEQUENCE: 11
uucgccacca ugccgcccut t                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 12
ucgccaccau gccgcccuat t                                              21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 13
cgccaccaug ccgcccuact t                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 14
gccaccaugc cgcccuacat t                                              21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 15
ccaccaugcc gcccuacact t                                              21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 16
caccaugccg cccuacacct t                                               21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 17
accaugccgc ccuacaccgt t                                               21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 18
ccaugccgcc cuacaccgut t                                               21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 19
caugccgccc uacaccgugt t                                               21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 20
augccgcccu acaccguggt t                                               21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: Description of Combined DNA/RNA Molecule:
      Synthetic oligonucleotide

<400> SEQUENCE: 21
ugccgcccua caccguggut t                                                    21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 22
gccgcccuac accgugguct t                                                    21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 23
ccgcccuaca ccguggucut t                                                    21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 24
cgcccuacac cguggucuat t                                                    21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 25
gcccuacacc guggucuaut t                                                    21

<210> SEQ ID NO 26
<211> LENGTH: 21
<212> TYPE: DNA
<213> ORGANISM: Artificial Sequence
<220> FEATURE:

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 26
cccuacaccg uggucuauut t                                              21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 27
ccuacaccgu ggucuauuut t                                              21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 28
cuacaccgug gucuauuuct t                                              21

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 29
uacaccgugg ucuauuucct t                                              21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 30
acaccguggu cuauuuccct t                                              21

<210> SEQ ID NO 31
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 31
caccgugguc uauuucccat t                                                21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 32
accguggucu auuucccagt t                                                21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 33
ccguggucua uuucccagut t                                                21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 34
cguggucuau uucccaguut t                                                21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 35
guggucuauu ucccaguuct t                                                21

<210> SEQ ID NO 36
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 36 uggcuauuu cccaguucgt t                                              21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 37
ggucuauuuc ccaguucgat t                                             21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 38
gucuauuccc caguucgagt t                                             21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 39
ucuauuuccc aguucgaggt t                                             21

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 40
cuauuuccca guucgaggct t                                             21

<210> SEQ ID NO 41
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 41
uauuucccag uucgaggcct t                                              21

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 42
auuucccagu ucgaggccgt t                                              21

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 43
uuucccaguu cgaggccgct t                                              21

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 44
uucccaguuc gaggccgcut t                                              21

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 45
ucccaguucg aggccgcugt t                                              21

<210> SEQ ID NO 46
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 46
cccaguucga ggccgcugct t                                             21

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 47
ccaguucgag gccgcugcgt t                                             21

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 48
caguucgagg ccgcugcgct t                                             21

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 49
aguucgaggc cgcugcgcgt t                                             21

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 50
guucgaggcc gcugcgcggt t                                             21
```

```
<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 51
uucgaggccg cugcgcggct t                                              21

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 52
ucgaggccgc ugcgcggcct t                                              21

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 53
cgaggccgcu gcgcggccct t                                              21

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 54
gaggccgcug cgcggcccut t                                              21

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 55
aggccgcugc gcggcccugt t                                              21
```

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 56
ggccgcugcg cggcccugct t                                              21

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 57
gccgcugcgc ggcccugcgt t                                              21

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 58
ccgcugcgcg gcccugcgct t                                              21

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 59
cgcugcgcgg cccugcgcat t                                              21

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 60
gcugcgcggc ccugcgcaut t                                              21

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 61
cugcgcggcc cugcgcaugt t                                          21

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 62
ugcgcggccc ugcgcaugct t                                          21

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 63
gcgcggcccu gcgcaugcut t                                          21

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 64
cgcggcccug cgcaugcugt t                                          21

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 65
gcggcccugc gcaugcugct t                                              21

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 66
cggcccugcg caugcugcut t                                              21

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 67
ggcccugcgc augcugcugt t                                              21

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 68
gcccugcgca ugcugcuggt t                                              21

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 69
cccugcgcau gcugcuggct t                                              21

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 70
ccugcgcaug cugcuggcat t                                              21

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 71
cugcgcaugc ugcuggcagt t                                              21

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 72
ugcgcaugcu gcuggcagat t                                              21

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 73
gcgcaugcug cuggcagaut t                                              21

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 74
cgcaugcugc uggcagauct t                                              21

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 75
gcaugcugcu ggcagaucat t                                              21

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 76
caugcugcug gcagaucagt t                                              21

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 77
augcugcugg cagaucaggt t                                              21

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 78
ugcugcuggc agaucagggt t                                              21

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 79
gcugcuggca gaucagggct t                                              21

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 80
cugcuggcag aucagggcct t                                              21

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 81
ugcuggcaga ucagggccat t                                              21

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 82
gcuggcagau cagggccagt t                                              21

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 83
cuggcagauc agggccagat t                                              21

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 84
uggcagauca gggccagagt t                                              21

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 85
ggcagaucag ggccagagct t                                              21

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 86
gcagaucagg gccagagcut t                                              21

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 87
cagaucaggg ccagagcugt t                                              21

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 88
agaucagggc cagagcuggt t                                              21

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 89
gaucagggcc agagcuggat t                                              21

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 90
aucagggcca gagcuggaat t                                              21

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 91
ucagggccag agcuggaagt t                                              21

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 92
cagggccaga gcuggaaggt t                                              21

<210> SEQ ID NO 93
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 93
agggccagag cuggaaggat t                                              21

<210> SEQ ID NO 94
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 94
gggccagagc uggaaggagt t                                              21

<210> SEQ ID NO 95
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 95
ggccagagcu ggaaggaggt t                                              21

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 96
gccagagcug gaaggaggat t                                              21

<210> SEQ ID NO 97
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 97
ccagagcugg aaggaggagt t                                              21

<210> SEQ ID NO 98
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 98
cagagcugga aggaggaggt t                                              21

<210> SEQ ID NO 99
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 99
agagcuggaa ggaggaggut t                                              21

<210> SEQ ID NO 100
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
                      oligonucleotide
<220> FEATURE:
<223> OTHER INFORMATION: Description of Combined DNA/RNA Molecule:
      Synthetic oligonucleotide

<400> SEQUENCE: 100
gagcuggaag gaggaggugt t                                              21

<210> SEQ ID NO 101
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 101
gagcuggaag gaggagguat t                                              21

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 102
agcuggaagg aggagguggt t                                              21

<210> SEQ ID NO 103
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 103
gcuggaagga ggagguggut t                                              21

<210> SEQ ID NO 104
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 104
cuggaaggag gagguggugt t                                              21

<210> SEQ ID NO 105
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 105
uggaaggagg agguggugat t                                              21

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 106
ggaaggagga gguggugact t                                              21

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 107
gaaggaggag guggugacct t                                              21

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 108
aaggaggagg uggugaccgt t                                              21

<210> SEQ ID NO 109
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 109
aggaggaggu ggugaccgut t                                              21

<210> SEQ ID NO 110
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 110
ggaggaggug gugaccgugt t                                              21

<210> SEQ ID NO 111
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 111
gaggaggugg ugaccguggt t                                              21

<210> SEQ ID NO 112
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 112
aggagguggu gaccguggat t                                              21

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 113
ggagguggug accguggagt t                                              21

<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 114
gaggugguga ccguggagat t                                              21

<210> SEQ ID NO 115
<211> LENGTH: 21
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 115
agguggugac cguggagact t                                              21

<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 116
gguggugacc guggagacgt t                                              21

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 117
guggugaccg uggagacgut t                                              21

<210> SEQ ID NO 118
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 118
uggugaccgu ggagacgugt t                                              21

<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 119
ggugaccgug gagacguggt t                                              21

<210> SEQ ID NO 120
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 120
gugaccgugg agacguggct t                                              21

<210> SEQ ID NO 121
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 121
ugaccgugga gacguggcat t                                              21

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 122
gaccguggag acguggcagt t                                              21

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 123
accguggaga cguggcaggt t                                              21

<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 124
ccguggagac guggcaggat t                                              21

<210> SEQ ID NO 125
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 125
cguggagacg uggcaggagt t                                              21

<210> SEQ ID NO 126
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 126
guggagacgu ggcaggaggt t                                              21

<210> SEQ ID NO 127
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 127
uggagacgug gcaggagggt t                                              21

<210> SEQ ID NO 128
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 128
ggagacgugg caggagggct t                                              21

<210> SEQ ID NO 129
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 129
gagacguggc aggagggcut t                                              21
```

```
<210> SEQ ID NO 130
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 130
agacguggca ggagggcuct t                                              21

<210> SEQ ID NO 131
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 131
gacguggcag gagggcucat t                                              21

<210> SEQ ID NO 132
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 132
acguggcagg agggcucact t                                              21

<210> SEQ ID NO 133
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 133
cguggcagga gggcucacut t                                              21

<210> SEQ ID NO 134
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 134
guggcaggag ggcucacuct t                                              21
```

```
<210> SEQ ID NO 135
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 135
uggcaggagg gcucacucat t                                                    21

<210> SEQ ID NO 136
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 136
ggcaggaggg cucacucaat t                                                    21

<210> SEQ ID NO 137
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 137
gcaggagggc ucacucaaat t                                                    21

<210> SEQ ID NO 138
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 138
caggagggcu cacucaaagt t                                                    21

<210> SEQ ID NO 139
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 139
aggagggcuc acucaaagct t                                                    21
```

```
<210> SEQ ID NO 140
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 140
ggagggcuca cucaaagcct t                                              21

<210> SEQ ID NO 141
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 141
gagggcucac ucaaagccut t                                              21

<210> SEQ ID NO 142
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 142
agggcucacu caaagccuct t                                              21

<210> SEQ ID NO 143
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 143
gggcucacuc aaagccucct t                                              21

<210> SEQ ID NO 144
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 144
```
ggcucacuca aagccuccut t                                              21

<210> SEQ ID NO 145
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 145
gcucacucaa agccuccugt t                                              21

<210> SEQ ID NO 146
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 146
cucacucaaa gccuccugct t                                              21

<210> SEQ ID NO 147
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 147
ucacucaaag ccuccugcct t                                              21

<210> SEQ ID NO 148
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 148
cacucaaagc cuccugccut t                                              21

<210> SEQ ID NO 149
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 149
acucaaagcc uccugccuat t                                               21

<210> SEQ ID NO 150
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 150
cucaaagccu ccugccuaut t                                               21

<210> SEQ ID NO 151
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 151
ucaaagccuc cugccuauat t                                               21

<210> SEQ ID NO 152
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 152
caaagccucc ugccuauact t                                               21

<210> SEQ ID NO 153
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 153
aaagccuccu gccuauacgt t                                               21

<210> SEQ ID NO 154
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide -continued

```
<400> SEQUENCE: 154
aagccuccug ccuauacggt t                                              21

<210> SEQ ID NO 155
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 155
agccuccugc cuauacgggt t                                              21

<210> SEQ ID NO 156
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 156
gccuccugcc uauacgggct t                                              21

<210> SEQ ID NO 157
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 157
ccuccugccu auacgggcat t                                              21

<210> SEQ ID NO 158
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 158
cuccugccua uacgggcagt t                                              21

<210> SEQ ID NO 159
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 159
uccugccuau acgggcagct t        21

<210> SEQ ID NO 160
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 160
ccugccuaua cgggcagcut t        21

<210> SEQ ID NO 161
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 161
cugccuauac gggcagcuct t        21

<210> SEQ ID NO 162
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 162
ugccuauacg ggcagcucct t        21

<210> SEQ ID NO 163
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 163
gccuauacgg gcagcuccct t        21

<210> SEQ ID NO 164
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

```
                            Synthetic oligonucleotide

<400> SEQUENCE: 164
cccaaguucc aggacggagt t                                               21

<210> SEQ ID NO 165
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 165
ccaaguucca ggacggagat t                                               21

<210> SEQ ID NO 166
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 166
caaguuccag gacggagact t                                               21

<210> SEQ ID NO 167
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 167
aaguuccagg acggagacct t                                               21

<210> SEQ ID NO 168
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 168
aguuccagga cggagaccut t                                               21

<210> SEQ ID NO 169
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

<223> OTHER INFORMATION: Description of Combined DNA/RNA Molecule:
      Synthetic oligonucleotide

<400> SEQUENCE: 169
guuccaggac ggagaccuct t                                              21

<210> SEQ ID NO 170
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 170
uuccaggacg gagaccucat t                                              21

<210> SEQ ID NO 171
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 171
uccaggacgg agaccucact t                                              21

<210> SEQ ID NO 172
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 172
ccaggacgga gaccucacct t                                              21

<210> SEQ ID NO 173
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 173
caggacggag accucaccct t                                              21

<210> SEQ ID NO 174
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide -continued <220> FEATURE:
<223> OTHER INFORMATION: Description of Combined DNA/RNA Molecule:
     Synthetic oligonucleotide

<400> SEQUENCE: 174
aggacggaga ccucacccut t                                              21

<210> SEQ ID NO 175
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide

<400> SEQUENCE: 175
ggacggagac cucacccugt t                                              21

<210> SEQ ID NO 176
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide

<400> SEQUENCE: 176
gacggagacc ucacccugut t                                              21

<210> SEQ ID NO 177
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide

<400> SEQUENCE: 177
acggagaccu cacccuguat t                                              21

<210> SEQ ID NO 178
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide

<400> SEQUENCE: 178
cggagaccuc acccuguact t                                              21

<210> SEQ ID NO 179
<211> LENGTH: 21
<212> TYPE: DNA
<213> ORGANISM: Artificial Sequence
<220> FEATURE:
<223> OTHER INFORMATION: Description of Artificial Sequence: Synthetic

```
      oligonucleotide
<220> FEATURE:
<223> OTHER INFORMATION: Description of Combined DNA/RNA Molecule:
      Synthetic oligonucleotide

<400> SEQUENCE: 179
ggagaccuca cccuguacct t                                          21

<210> SEQ ID NO 180
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 180
gagaccucac ccuguaccat t                                          21

<210> SEQ ID NO 181
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 181
agaccucacc cuguaccagt t                                          21

<210> SEQ ID NO 182
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 182
gaccucaccc uguaccagut t                                          21

<210> SEQ ID NO 183
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 183
accucacccu guaccaguct t                                          21

<210> SEQ ID NO 184
<211> LENGTH: 21
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 184
ccucacccug uaccagucct t                                              21

<210> SEQ ID NO 185
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 185
cucacccugu accaguccat t                                              21

<210> SEQ ID NO 186
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 186
ucacccugua ccaguccaat t                                              21

<210> SEQ ID NO 187
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 187
cacccuguac caguccaaut t                                              21

<210> SEQ ID NO 188
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 188 acccguacc aguccaauat t                                               21

<210> SEQ ID NO 189
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 189
cccuguacca guccaauact t                                                   21

<210> SEQ ID NO 190
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 190
ccuguaccag uccaauacct t                                                   21

<210> SEQ ID NO 191
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 191
cuguaccagu ccaauaccat t                                                   21

<210> SEQ ID NO 192
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 192
uguaccaguc caauaccaut t                                                   21

<210> SEQ ID NO 193
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 193
guaccagucc aauaccauct t                                                   21

<210> SEQ ID NO 194
<211> LENGTH: 21
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 194
uaccagucca auaccaucct t                                              21

<210> SEQ ID NO 195
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 195
accaguccaa uaccauccut t                                              21

<210> SEQ ID NO 196
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 196
ccaguccaau accauccugt t                                              21

<210> SEQ ID NO 197
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 197
caguccaaua ccauccugct t                                              21

<210> SEQ ID NO 198
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 198
aguccaauac cauccugcgt t                                              21

<210> SEQ ID NO 199
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 199
guccaauacc auccugcgut t                                              21

<210> SEQ ID NO 200
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 200
uccaauacca uccugcguct t                                              21

<210> SEQ ID NO 201
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 201
ccaauaccau ccugcgucat t                                              21

<210> SEQ ID NO 202
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 202
caauaccauc cugcgucact t                                              21

<210> SEQ ID NO 203
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 203
aauaccaucc ugcgucacct t                                              21

<210> SEQ ID NO 204
```

-continued

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 204
auaccauccu gcgucaccut t                                              21

<210> SEQ ID NO 205
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 205
uaccauccug cgucaccugt t                                              21

<210> SEQ ID NO 206
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 206
accauccugc gucaccuggt t                                              21

<210> SEQ ID NO 207
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 207
ccauccugcg ucaccugggt t                                              21

<210> SEQ ID NO 208
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 208
cauccugcgu caccugggct t                                              21
```

```
<210> SEQ ID NO 209
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 209
auccugcguc accugggcct t                                              21

<210> SEQ ID NO 210
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 210
uccugcguca ccugggccgt t                                              21

<210> SEQ ID NO 211
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 211
ccugcgucac cugggccgct t                                              21

<210> SEQ ID NO 212
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 212
cugcgucacc ugggccgcat t                                              21

<210> SEQ ID NO 213
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 213
ugcgucaccu gggccgcact t                                              21
```

<210> SEQ ID NO 214
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 214
gcgucaccug ggccgcacct t                                              21

<210> SEQ ID NO 215
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 215
cgucaccugg gccgcaccct t                                              21

<210> SEQ ID NO 216
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 216
gucaccuggg ccgcacccut t                                              21

<210> SEQ ID NO 217
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 217
ucaccugggc cgcacccuut t                                              21

<210> SEQ ID NO 218
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 218
caccugggcc gcacccuugt t                                              21

<210> SEQ ID NO 219
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 219
accugggccg cacccuuggt t                                            21

<210> SEQ ID NO 220
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 220
ccugggccgc acccuugggt t                                            21

<210> SEQ ID NO 221
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 221
cugggccgca cccuugggct t                                            21

<210> SEQ ID NO 222
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 222
ugggccgcac ccuugggcut t                                            21

<210> SEQ ID NO 223
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 223
gggccgcacc cuugggcuct t                                                      21

<210> SEQ ID NO 224
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 224
ggccgcaccc uugggcucut t                                                      21

<210> SEQ ID NO 225
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 225
gccgcacccu ugggcucuat t                                                      21

<210> SEQ ID NO 226
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 226
ccgcacccuu gggcucuaut t                                                      21

<210> SEQ ID NO 227
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 227
cgcacccuug ggcucuaugt t                                                      21

<210> SEQ ID NO 228
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 228
gcacccuugg gcucuauggt t                                              21

<210> SEQ ID NO 229
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 229
cacccuuggg cucuaugggt t                                              21

<210> SEQ ID NO 230
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 230
acccuugggc ucuaugggat t                                              21

<210> SEQ ID NO 231
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 231
cccuugggcu cuaugggaat t                                              21

<210> SEQ ID NO 232
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 232
ccuugggcuc uaugggaagt t                                              21

<210> SEQ ID NO 233
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 233
cuugggcucu augggaaggt t                                              21

<210> SEQ ID NO 234
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 234
uugggcucua ugggaaggat t                                              21

<210> SEQ ID NO 235
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 235
ugggcucuau gggaaggact t                                              21

<210> SEQ ID NO 236
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 236
gggcucuaug ggaaggacct t                                              21

<210> SEQ ID NO 237
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 237
ggcucuaugg gaaggaccat t                                              21

<210> SEQ ID NO 238
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 238
gcucuauggg aaggaccagt t                                              21

<210> SEQ ID NO 239
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 239
cucuauggga aggaccagct t                                              21

<210> SEQ ID NO 240
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 240 ucuauggggaa ggaccagcat t                                             21

<210> SEQ ID NO 241
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 241
cuaugggaag gaccagcagt t                                              21

<210> SEQ ID NO 242
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 242
uaugggaagg accagcaggt t                                              21

<210> SEQ ID NO 243
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 243
augggaagga ccagcaggat t                                              21

<210> SEQ ID NO 244
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 244
ugggaaggac cagcaggagt t                                              21

<210> SEQ ID NO 245
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 245
gggaaggacc agcaggaggt t                                              21

<210> SEQ ID NO 246
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 246
ggaaggacca gcaggaggct t                                              21

<210> SEQ ID NO 247
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 247
gaaggaccag caggaggcat t                                              21

<210> SEQ ID NO 248
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

-continued

```
<223> OTHER INFORMATION: Description of Combined DNA/RNA Molecule:
      Synthetic oligonucleotide

<400> SEQUENCE: 248
aaggaccagc aggaggcagt t                                              21

<210> SEQ ID NO 249
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 249
aggaccagca ggaggcagct t                                              21

<210> SEQ ID NO 250
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 250
ggaccagcag gaggcagcct t                                              21

<210> SEQ ID NO 251
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 251
gaccagcagg aggcagccct t                                              21

<210> SEQ ID NO 252
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 252
accagcagga ggcagcccut t                                              21

<210> SEQ ID NO 253
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 253
ccagcaggag gcagcccugt t                                              21

<210> SEQ ID NO 254
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 254
cagcaggagg cagcccuggt t                                              21

<210> SEQ ID NO 255
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 255
agcaggaggc agcccuggut t                                              21

<210> SEQ ID NO 256
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 256
gcaggaggca gcccuggugt t                                              21

<210> SEQ ID NO 257
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 257
caggaggcag cccugguggt t                                              21

<210> SEQ ID NO 258
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
        oligonucleotide
<220> FEATURE:
<223> OTHER INFORMATION: Description of Combined DNA/RNA Molecule:
      Synthetic oligonucleotide

<400> SEQUENCE: 258
aggaggcagc ccuggguggat t                                              21

<210> SEQ ID NO 259
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 259
ggaggcagcc cugguggact t                                               21

<210> SEQ ID NO 260
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 260
gaggcagccc ugguggacat t                                               21

<210> SEQ ID NO 261
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 261
aggcagcccu ggugggacaut t                                              21

<210> SEQ ID NO 262
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 262
ggcagcccug guggacaugt t                                               21

<210> SEQ ID NO 263
<211> LENGTH: 21
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 263
gcagcccugg uggacauggt t                                             21

<210> SEQ ID NO 264
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 264
cagcccuggu ggacauggut t                                             21

<210> SEQ ID NO 265
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 265
agcccuggug gacauggugt t                                             21

<210> SEQ ID NO 266
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 266
gcccuggugg acauggugat t                                             21

<210> SEQ ID NO 267
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 267
cccuggugga cauggugaat t                                             21

<210> SEQ ID NO 268
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 268
ccugguggac auggugaaut t                                              21

<210> SEQ ID NO 269
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 269
cugguggaca uggugaaugt t                                              21

<210> SEQ ID NO 270
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 270
ugguggacau ggugaaugat t                                              21

<210> SEQ ID NO 271
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 271
gguggacaug gugaaugact t                                              21

<210> SEQ ID NO 272
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 272
guggacaugg ugaaugacgt t                                              21

<210> SEQ ID NO 273
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 273
uggacauggu gaaugacggt t                                              21

<210> SEQ ID NO 274
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 274
ggacauggug aaugacggct t                                              21

<210> SEQ ID NO 275
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 275
gacaugguga augacggcgt t                                              21

<210> SEQ ID NO 276
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 276
acauggugaa ugacggcgut t                                              21

<210> SEQ ID NO 277
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 277
cauggugaau gacggcgugt t                                              21

<210> SEQ ID NO 278
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 278
auggugaaug acggcguggt t                                             21

<210> SEQ ID NO 279
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 279
uggugaauga cggcguggat t                                             21

<210> SEQ ID NO 280
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 280
ggugaaugac ggcguggagt t                                             21

<210> SEQ ID NO 281
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 281
gugaaugacg gcguggaggt t                                             21

<210> SEQ ID NO 282
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 282
ugaaugacgg cguggaggat t                                             21

<210> SEQ ID NO 283
```

-continued

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 283
gaaugacggc guggaggact t                                              21

<210> SEQ ID NO 284
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 284
aaugacggcg uggaggacct t                                              21

<210> SEQ ID NO 285
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 285
augacggcgu ggaggaccut t                                              21

<210> SEQ ID NO 286
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 286
ugacggcgug gaggaccuct t                                              21

<210> SEQ ID NO 287
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 287
gacggcgugg aggaccucct t                                              21
```

```
<210> SEQ ID NO 288
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 288
acggcgugga ggaccuccgt t                                           21

<210> SEQ ID NO 289
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 289
cggcguggag gaccuccgct t                                           21

<210> SEQ ID NO 290
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 290
ggcguggagg accuccgcut t                                           21

<210> SEQ ID NO 291
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 291
gcguggagga ccuccgcugt t                                           21

<210> SEQ ID NO 292
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 292
cguggaggac cuccgcuget t                                           21
```

<210> SEQ ID NO 293
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 293
guggaggacc uccgcugcat t                                              21

<210> SEQ ID NO 294
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 294
uggaggaccu ccgcugcaat t                                              21

<210> SEQ ID NO 295
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 295
ggaggaccuc cgcugcaaat t                                              21

<210> SEQ ID NO 296
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 296
gaggaccucc gcugcaaaut t                                              21

<210> SEQ ID NO 297
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 297
aggaccuccg cugcaaauat t                                              21

<210> SEQ ID NO 298
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 298
ggaccuccgc ugcaaauact t                                        21

<210> SEQ ID NO 299
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 299
gaccuccgcu gcaaauacat t                                        21

<210> SEQ ID NO 300
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 300
accuccgcug caaauacaut t                                        21

<210> SEQ ID NO 301
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 301
ccuccgcugc aaauacauct t                                        21

<210> SEQ ID NO 302
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 302
cuccgcugca aauacaucut t                                              21

<210> SEQ ID NO 303
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 303
uccgcugcaa auacaucuct t                                              21

<210> SEQ ID NO 304
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 304
ccgcugcaaa uacaucucct t                                              21

<210> SEQ ID NO 305
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 305
cgcugcaaau acaucuccct t                                              21

<210> SEQ ID NO 306
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 306
gcugcaaaua caucccccut t                                              21

<210> SEQ ID NO 307
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 307

-continued cugcaaauac aucucccuct t                                                       21

<210> SEQ ID NO 308
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 308
ugcaaauaca ucucccucat t                                                       21

<210> SEQ ID NO 309
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 309
gcaaauacau cucccucaut t                                                       21

<210> SEQ ID NO 310
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 310
caaauacauc ucccucauct t                                                       21

<210> SEQ ID NO 311
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 311
aaauacaucu cccucaucut t                                                       21

<210> SEQ ID NO 312
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 312
aauacaucuc ccucaucuat t                                              21

<210> SEQ ID NO 313
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 313
auacaucucc cucaucuact t                                              21

<210> SEQ ID NO 314
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 314
uacaucuccc ucaucuacat t                                              21

<210> SEQ ID NO 315
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 315
acaucucccu caucuacact t                                              21

<210> SEQ ID NO 316
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 316
caucucccuc aucuacacct t                                              21

<210> SEQ ID NO 317
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 317
aucucccuca ucuacaccat t                                              21

<210> SEQ ID NO 318
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 318
ucucccucau cuacaccaat t                                              21

<210> SEQ ID NO 319
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 319
gcucccucau cuacaccaat t                                              21

<210> SEQ ID NO 320
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 320
cucccucauc uacaccaact t                                              21

<210> SEQ ID NO 321
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 321
ucccucaucu acaccaacut t                                              21

<210> SEQ ID NO 322
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 322
cucccucauc uacaccaaat t					21

<210> SEQ ID NO 323
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 323
cccucaucua caccaacuat t					21

<210> SEQ ID NO 324
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 324
ccucaucuac accaacuaut t					21

<210> SEQ ID NO 325
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 325
ccucaucuac accaacuaat t					21

<210> SEQ ID NO 326
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 326
cucaucuaca ccaacuaugt t					21

<210> SEQ ID NO 327
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: Description of Combined DNA/RNA Molecule:
      Synthetic oligonucleotide

<400> SEQUENCE: 327
ucaucuacac caacuaugat t                                              21

<210> SEQ ID NO 328
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 328
caucuacacc aacuaugagt t                                              21

<210> SEQ ID NO 329
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 329
aucuacacca acuaugaggt t                                              21

<210> SEQ ID NO 330
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 330
ucuacaccaa cuaugaggct t                                              21

<210> SEQ ID NO 331
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 331
cuacaccaac uaugaggcgt t                                              21

<210> SEQ ID NO 332
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 332
uacaccaacu augaggcggt t                                              21

<210> SEQ ID NO 333
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 333
acaccaacua ugaggcgggt t                                              21

<210> SEQ ID NO 334
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 334
caccaacuau gaggcgggct t                                              21

<210> SEQ ID NO 335
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 335
accaacuaug aggcgggcat t                                              21

<210> SEQ ID NO 336
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 336
ccaacuauga ggcgggcaat t                                              21

<210> SEQ ID NO 337
<211> LENGTH: 21
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: Description of Combined DNA/RNA Molecule:
      Synthetic oligonucleotide

<400> SEQUENCE: 337
caacuaugag gcgggcaagt t                                              21

<210> SEQ ID NO 338
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 338
aacuaugagg cgggcaaggt t                                              21

<210> SEQ ID NO 339
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 339
acuaugaggc gggcaaggat t                                              21

<210> SEQ ID NO 340
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 340
cuaugaggcg ggcaaggaut t                                              21

<210> SEQ ID NO 341
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 341
uaugaggcgg gcaaggaugt t                                              21

<210> SEQ ID NO 342
<211> LENGTH: 21
<212> TYPE: DNA
<213> ORGANISM: Artificial Sequence
<220> FEATURE:

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 342
augaggcggg caaggaugat t                                           21

<210> SEQ ID NO 343
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 343
ugaggcgggc aaggaugact t                                           21

<210> SEQ ID NO 344
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 344
gaggcgggca aggaugacut t                                           21

<210> SEQ ID NO 345
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 345
aggcgggcaa ggaugacuat t                                           21

<210> SEQ ID NO 346
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 346
ggcgggcaag gaugacuaut t                                           21

<210> SEQ ID NO 347
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 347
gcgggcaagg augacuaugt t                                              21

<210> SEQ ID NO 348
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 348
cgggcaagga ugacuaugut t                                              21

<210> SEQ ID NO 349
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 349
gggcaaggau gacuaugugt t                                              21

<210> SEQ ID NO 350
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 350
ggcaaggaug acuaugugat t                                              21

<210> SEQ ID NO 351
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 351
gcaaggauga cuaugugaat t                                              21

<210> SEQ ID NO 352
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 352
caaggaugac uaugugaagt t                                              21

<210> SEQ ID NO 353
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 353
aaggaugacu augugaaggt t                                              21

<210> SEQ ID NO 354
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 354
aggaugacua ugugaaggct t                                              21

<210> SEQ ID NO 355
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 355
ggaugacuau gugaaggcat t                                              21

<210> SEQ ID NO 356
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 356
gaugacuaug ugaaggcact t                                              21

<210> SEQ ID NO 357
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 357
augacuaugu gaaggcacut t                                          21

<210> SEQ ID NO 358
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 358
ugacuaugug aaggcacugt t                                          21

<210> SEQ ID NO 359
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 359
gacuauguga aggcacugct t                                          21

<210> SEQ ID NO 360
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 360
acuaugugaa ggcacugcct t                                          21

<210> SEQ ID NO 361
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 361
cuaugugaag gcacugccct t                                          21

<210> SEQ ID NO 362
```

-continued

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 362
uaugugaagg cacugcccgt t                                              21

<210> SEQ ID NO 363
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 363
augugaaggc acugcccggt t                                              21

<210> SEQ ID NO 364
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 364
ugugaaggca cugcccgggt t                                              21

<210> SEQ ID NO 365
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 365
gugaaggcac ugcccgggct t                                              21

<210> SEQ ID NO 366
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 366
ugaaggcacu gcccgggcat t                                              21
```

```
<210> SEQ ID NO 367
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 367
gaaggcacug cccgggcaat t                                             21

<210> SEQ ID NO 368
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 368
aaggcacugc ccgggcaact t                                             21

<210> SEQ ID NO 369
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 369
aggcacugcc cgggcaacut t                                             21

<210> SEQ ID NO 370
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 370
ggcacugccc gggcaacugt t                                             21

<210> SEQ ID NO 371
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 371
gcacugcccg ggcaacugat t                                             21
```

```
<210> SEQ ID NO 372
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 372
cacugcccgg gcaacugaat t                                              21

<210> SEQ ID NO 373
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 373
acugcccggg caacugaagt t                                              21

<210> SEQ ID NO 374
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 374
cugcccgggc aacugaagct t                                              21

<210> SEQ ID NO 375
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 375
ugcccgggca acugaagcct t                                              21

<210> SEQ ID NO 376
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 376
gcccgggcaa cugaagccut t                                              21
```

<210> SEQ ID NO 377
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 377
cccgggcaac ugaagccuut t                                              21

<210> SEQ ID NO 378
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 378
ccgggcaacu gaagccuuut t                                              21

<210> SEQ ID NO 379
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 379
cgggcaacug aagccuuuut t                                              21

<210> SEQ ID NO 380
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 380
gggcaacuga agccuuuugt t                                              21

<210> SEQ ID NO 381
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 381
ggcaacugaa gccuuuugat t                                              21

<210> SEQ ID NO 382
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 382
gcaacugaag ccuuuugagt t                                              21

<210> SEQ ID NO 383
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 383
caacugaagc cuuuugagat t                                              21

<210> SEQ ID NO 384
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 384
aacugaagcc uuuugagact t                                              21

<210> SEQ ID NO 385
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 385
acugaagccu uuugagacct t                                              21

<210> SEQ ID NO 386
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 386
acugaagccu uuugagacat t                                                21

<210> SEQ ID NO 387
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 387
cugaagccuu uugagaccct t                                                21

<210> SEQ ID NO 388
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 388
ugaagccuuu ugagacccut t                                                21

<210> SEQ ID NO 389
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 389
gaagccuuuu gagacccugt t                                                21

<210> SEQ ID NO 390
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 390
aagccuuuug agacccugct t                                                21

<210> SEQ ID NO 391
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 391
gaagccuuuu gagacccuat t                                              21

<210> SEQ ID NO 392
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 392
agccuuuuga gacccugcut t                                              21

<210> SEQ ID NO 393
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 393
cgccuuuuga gacccugcat t                                              21

<210> SEQ ID NO 394
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 394
agccuuuuga gacccugcat t                                              21

<210> SEQ ID NO 395
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 395
gccuuuugag acccugcugt t                                              21

<210> SEQ ID NO 396
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 396
ccuuuugaga cccugcugut t                                          21

<210> SEQ ID NO 397
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 397
ccuuuugaga cccugcugat t                                          21

<210> SEQ ID NO 398
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 398
cuuuugagac ccugcuguct t                                          21

<210> SEQ ID NO 399
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 399
cuuuugagac ccugcuguat t                                          21

<210> SEQ ID NO 400
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 400
uuuugagacc cugcugucct t                                          21

<210> SEQ ID NO 401
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide

<400> SEQUENCE: 401
uuugagaccc ugcugucccu t                                             21

<210> SEQ ID NO 402
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 402
uugagacccu gcugucccau t                                             21

<210> SEQ ID NO 403
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 403
ugagacccug cugucccagt t                                             21

<210> SEQ ID NO 404
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 404
gagacccugc ugucccagat t                                             21

<210> SEQ ID NO 405
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 405
agacccugcu gucccagaat t                                             21

<210> SEQ ID NO 406
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 406
gacccugcug ucccagaact t                                              21

<210> SEQ ID NO 407
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 407
acccugcugu cccagaacct t                                              21

<210> SEQ ID NO 408
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 408
acccugcugu cccagaacat t                                              21

<210> SEQ ID NO 409
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 409
cccugcuguc ccagaaccat t                                              21

<210> SEQ ID NO 410
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 410
ccugcugucc cagaaccagt t                                              21

<210> SEQ ID NO 411
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 411
cugcuguccc agaaccaggt t                                                 21

<210> SEQ ID NO 412
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 412
ugcuguccca gaaccagggt t                                                 21

<210> SEQ ID NO 413
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 413
ugcuguccca gaaccaggat t                                                 21

<210> SEQ ID NO 414
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 414
gcugucccag aaccagggat t                                                 21

<210> SEQ ID NO 415
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 415
cugucccaga accagggagt t                                                 21

<210> SEQ ID NO 416
<211> LENGTH: 21
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: Description of Combined DNA/RNA Molecule:
      Synthetic oligonucleotide

<400> SEQUENCE: 416
ugucccagaa ccagggaggt t                                              21

<210> SEQ ID NO 417
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 417
gucccagaac cagggaggct t                                              21

<210> SEQ ID NO 418
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 418
ucccagaacc agggaggcat t                                              21

<210> SEQ ID NO 419
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 419
cccagaacca gggaggcaat t                                              21

<210> SEQ ID NO 420
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 420
ccagaaccag ggaggcaagt t                                              21

<210> SEQ ID NO 421
<211> LENGTH: 21
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 421
cagaaccagg gaggcaagat t                                               21

<210> SEQ ID NO 422
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 422
agaaccaggg aggcaagact t                                               21

<210> SEQ ID NO 423
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 423
gaaccaggga ggcaagacct t                                               21

<210> SEQ ID NO 424
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 424
aaccagggag gcaagaccut t                                               21

<210> SEQ ID NO 425
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 425
accagggagg caagaccuut t                                               21

<210> SEQ ID NO 426
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 426
ccagggaggc aagaccuuct t                                            21

<210> SEQ ID NO 427
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 427
cagggaggca agaccuucat t                                            21

<210> SEQ ID NO 428
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 428
agggaggcaa gaccuucaut t                                            21

<210> SEQ ID NO 429
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 429
gggaggcaag accuucauut t                                            21

<210> SEQ ID NO 430
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 430
ggaggcaaga ccuucauugt t                                            21

<210> SEQ ID NO 431
<211> LENGTH: 21
<212> TYPE: DNA
```

<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 431
gaggcaagac cuucauugut t                                              21

<210> SEQ ID NO 432
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 432
aggcaagacc uucauugugt t                                              21

<210> SEQ ID NO 433
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 433
ggcaagaccu ucauguggt t                                               21

<210> SEQ ID NO 434
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 434
gcaagaccuu cauguggt t                                                21

<210> SEQ ID NO 435
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 435
caagaccuuc auguggat t                                                21

<210> SEQ ID NO 436
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 436
aagaccuuca uugugggagt t                                              21

<210> SEQ ID NO 437
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 437
agaccuucau ugugggagat t                                              21

<210> SEQ ID NO 438
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 438
gaccuucauu gugggagact t                                              21

<210> SEQ ID NO 439
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 439
accuucauug ugggagacct t                                              21

<210> SEQ ID NO 440
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 440
ccuucauugu gggagaccat t                                              21

<210> SEQ ID NO 441
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 441
cuucauugug ggagaccagt t                                            21

<210> SEQ ID NO 442
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 442
uucauugugg gagaccagat t                                            21

<210> SEQ ID NO 443
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 443 ucauguggg agaccagaut t                                             21

<210> SEQ ID NO 444
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 444
cauuguggga gaccagauct t                                            21

<210> SEQ ID NO 445
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 445
auugugggag accagaucut t                                            21
```

```
<210> SEQ ID NO 446
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 446
uugugggaga ccagaucuct t                                              21

<210> SEQ ID NO 447
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 447
ugugggagac cagaucucct t                                              21

<210> SEQ ID NO 448
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 448
gugggagacc agaucuccut t                                              21

<210> SEQ ID NO 449
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 449
ugggagacca gaucuccuut t                                              21

<210> SEQ ID NO 450
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 450
gggagaccag aucccuuct t                                               21
```

```
<210> SEQ ID NO 451
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 451
ggagaccaga ucuccuucgt t                                              21

<210> SEQ ID NO 452
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 452
gagaccagau cuccuucgct t                                              21

<210> SEQ ID NO 453
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 453
agaccagauc uccuucgcut t                                              21

<210> SEQ ID NO 454
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 454
gaccagaucu ccuucgcugt t                                              21

<210> SEQ ID NO 455
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 455
accagaucuc cuucgcugat t                                              21
```

<210> SEQ ID NO 456
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 456
ccagaucucc uucgcugact t                                              21

<210> SEQ ID NO 457
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 457
cagaucuccu ucgcugacut t                                              21

<210> SEQ ID NO 458
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 458
agaucuccuu cgcugacuat t                                              21

<210> SEQ ID NO 459
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 459
gaucuccuuc gcugacuact t                                              21

<210> SEQ ID NO 460
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 460
aucuccuucg cugacuacat t            21

<210> SEQ ID NO 461
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 461 ucccuucgc ugacuacaat t            21

<210> SEQ ID NO 462
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 462
cuccuucgcu gacuacaact t            21

<210> SEQ ID NO 463
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 463
uccuucgcug acuacaacct t            21

<210> SEQ ID NO 464
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 464
ccuucgcuga cuacaaccut t            21

<210> SEQ ID NO 465
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 465
cuucgcugac uacaaccugt t					21

<210> SEQ ID NO 466
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 466
uucgcugacu acaaccugct t					21

<210> SEQ ID NO 467
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 467
ucgcugacua caaccugcut t					21

<210> SEQ ID NO 468
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 468
cgcugacuac aaccugcugt t					21

<210> SEQ ID NO 469
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 469
gcugacuaca accugcuggt t					21

<210> SEQ ID NO 470
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide -continued

<400> SEQUENCE: 470
cugacuacaa ccugcuggat t                                              21

<210> SEQ ID NO 471
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 471
ugacuacaac cugcuggact t                                              21

<210> SEQ ID NO 472
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 472
gacuacaacc ugcuggacut t                                              21

<210> SEQ ID NO 473
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 473
acuacaaccu gcuggacuut t                                              21

<210> SEQ ID NO 474
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 474
cuacaaccug cuggacuugt t                                              21

<210> SEQ ID NO 475
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 475
uacaaccugc uggacuugct t                                              21

<210> SEQ ID NO 476
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 476
acaaccugcu ggacuugcut t                                              21

<210> SEQ ID NO 477
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 477
caaccugcug gacuugcugt t                                              21

<210> SEQ ID NO 478
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 478
aaccugcugg acuugcugct t                                              21

<210> SEQ ID NO 479
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 479
accugcugga cuugcugcut t                                              21

<210> SEQ ID NO 480
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide

<400> SEQUENCE: 480
ccugcuggac uugcugcugt t                                              21

<210> SEQ ID NO 481
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 481
cugcuggacu ugcugcugat t                                              21

<210> SEQ ID NO 482
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 482
ugcuggacuu gcugcugaut t                                              21

<210> SEQ ID NO 483
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 483
gcuggacuug cugcugauct t                                              21

<210> SEQ ID NO 484
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 484
cuggacuugc ugcugaucct t                                              21

<210> SEQ ID NO 485
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

-continued

```
<223> OTHER INFORMATION: Description of Combined DNA/RNA Molecule:
      Synthetic oligonucleotide

<400> SEQUENCE: 485
uggacuugcu gcugauccat t                                              21

<210> SEQ ID NO 486
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 486
ggacuugcug cugauccaut t                                              21

<210> SEQ ID NO 487
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 487
gacuugcugc ugauccaugt t                                              21

<210> SEQ ID NO 488
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 488
acuugcugcu gauccaugat t                                              21

<210> SEQ ID NO 489
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 489
cuugcugcug auccaugagt t                                              21

<210> SEQ ID NO 490
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 490
uugcugcuga uccaugaggt t                                              21

<210> SEQ ID NO 491
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 491
ugcugcugau ccaugaggut t                                              21

<210> SEQ ID NO 492
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 492
gcugcugauc caugagguct t                                              21

<210> SEQ ID NO 493
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 493
cugcugaucc augaggucct t                                              21

<210> SEQ ID NO 494
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 494
ugcugaucca ugagguccut t                                              21

<210> SEQ ID NO 495
<211> LENGTH: 21
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: Description of Combined DNA/RNA Molecule:
      Synthetic oligonucleotide

<400> SEQUENCE: 495
gcugauccau gagguccuat t                                              21

<210> SEQ ID NO 496
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 496
cugauccaug agguccuagt t                                              21

<210> SEQ ID NO 497
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 497
ugauccauga gguccuagct t                                              21

<210> SEQ ID NO 498
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 498
gauccaugag guccuagcct t                                              21

<210> SEQ ID NO 499
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 499
auccaugagg uccuagccct t                                              21

<210> SEQ ID NO 500
<211> LENGTH: 21
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 500
cccuggcugc cuggaugcgt t                                              21

<210> SEQ ID NO 501
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 501
ccuggcugcc uggaugcguu t                                              21

<210> SEQ ID NO 502
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 502
cuggcugccu ggaugcguut t                                              21

<210> SEQ ID NO 503
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 503
uggcugccug gaugcguuct t                                              21

<210> SEQ ID NO 504
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 504
ggcugccugg augcguucct t                                              21

<210> SEQ ID NO 505
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 505
gcugccugga ugcguuccct t                                              21

<210> SEQ ID NO 506
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 506
cccugcucuc agcauaugut t                                              21

<210> SEQ ID NO 507
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 507
ccugcucuca gcauaugugt t                                              21

<210> SEQ ID NO 508
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 508
cugcucucag cauauguggt t                                              21

<210> SEQ ID NO 509
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 509
ugcucucagc auaugugggt t                                              21

<210> SEQ ID NO 510
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 510
gggcgccuca gugcccggct t                                              21

<210> SEQ ID NO 511
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 511
ggcgccucag ugcccggcct t                                              21

<210> SEQ ID NO 512
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 512
gcgccucagu gcccggccct t                                              21

<210> SEQ ID NO 513
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 513
cgccucagug cccggcccat t                                              21

<210> SEQ ID NO 514
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 514
gccucagugc ccggcccaat t                                              21

<210> SEQ ID NO 515
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 515
ccucagugcc cggcccaagt t                                              21

<210> SEQ ID NO 516
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 516
cucagugccc ggcccaagct t                                              21

<210> SEQ ID NO 517
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 517
ucagugcccg gcccaagcut t                                              21

<210> SEQ ID NO 518
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 518
cagugcccgg cccaagcuct t                                              21

<210> SEQ ID NO 519
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 519
agugcccggc ccaagcucat t                                              21

<210> SEQ ID NO 520
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 520
gugcccggcc caagcucaat t                                              21

<210> SEQ ID NO 521
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 521
ugcccggccc aagcucaagt t                                              21

<210> SEQ ID NO 522
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 522
gcccggccca agcucaaggt t                                              21

<210> SEQ ID NO 523
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 523
cccggcccaa gcucaaggct t                                              21

<210> SEQ ID NO 524
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 524
ccggcccaag cucaaggcct t                                              21
```

```
<210> SEQ ID NO 525
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 525
cggcccaagc ucaaggccut t                                              21

<210> SEQ ID NO 526
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 526
ggcccaagcu caaggccuut t                                              21

<210> SEQ ID NO 527
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 527
gcccaagcuc aaggccuuct t                                              21

<210> SEQ ID NO 528
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 528
cccaagcuca aggccuucct t                                              21

<210> SEQ ID NO 529
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 529
ccaagcucaa ggccuuccut t                                              21
```

<210> SEQ ID NO 530
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 530
caagcucaag gccuuccugt t          21

<210> SEQ ID NO 531
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 531
aagcucaagg ccuuccuggt t          21

<210> SEQ ID NO 532
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 532
agcucaaggc cuuccuggct t          21

<210> SEQ ID NO 533
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 533
gcucaaggcc uuccuggcct t          21

<210> SEQ ID NO 534
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 534
cucaaggccu uccuggccut t          21

<210> SEQ ID NO 535
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 535
ucaaggccuu ccuggccuct t                                              21

<210> SEQ ID NO 536
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 536
caaggccuuc cuggccucct t                                              21

<210> SEQ ID NO 537
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 537
aaggccuucc uggccuccct t                                              21

<210> SEQ ID NO 538
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 538
cccugaguac gugaaccuct t                                              21

<210> SEQ ID NO 539
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 539
ccugaguacg ugaaccucct t                                          21

<210> SEQ ID NO 540
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 540
cugaguacgu gaaccuccct t                                          21

<210> SEQ ID NO 541
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 541
cccaucaaug gcaacgggat t                                          21

<210> SEQ ID NO 542
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 542
ccaucaaugg caacgggaat t                                          21

<210> SEQ ID NO 543
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 543
caucaauggc aacgggaaat t                                          21

<210> SEQ ID NO 544
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 544
aucaauggca acgggaaact t				21

<210> SEQ ID NO 545
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 545
ucaauggcaa cgggaaacat t				21

<210> SEQ ID NO 546
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 546
caauggcaac gggaaacagt t				21

<210> SEQ ID NO 547
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 547
aauggcaacg ggaaacagut t				21

<210> SEQ ID NO 548
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 548
auggcaacgg gaaacagugt t				21

<210> SEQ ID NO 549
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide -continued

```
<400> SEQUENCE: 549
uggcaacggg aaacagugat t                                              21

<210> SEQ ID NO 550
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 550
ggcaacggga aacagugagt t                                              21

<210> SEQ ID NO 551
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 551
gcaacgggaa acagugaggt t                                              21

<210> SEQ ID NO 552
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 552
caacgggaaa cagugagggt t                                              21

<210> SEQ ID NO 553
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 553
aacgggaaac agugagggut t                                              21

<210> SEQ ID NO 554
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 554
acgggaaaca gugagggguut t                                            21

<210> SEQ ID NO 555
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 555
cgggaaacag ugaggguugt t                                             21

<210> SEQ ID NO 556
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 556
gggaaacagu gaggguuggt t                                             21

<210> SEQ ID NO 557
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 557
ggaaacagug aggguugggt t                                             21

<210> SEQ ID NO 558
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 558
gggacucuga gcgggaggct t                                             21

<210> SEQ ID NO 559
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 559
ggacucugag cgggaggcat t                                              21

<210> SEQ ID NO 560
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 560
acucugagcg ggaggcagat t                                              21

<210> SEQ ID NO 561
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 561
ucugagcggg aggcagagut t                                              21

<210> SEQ ID NO 562
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 562
cugagcggga ggcagaguut t                                              21

<210> SEQ ID NO 563
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 563
ugagcgggag gcagaguuut t                                              21

<210> SEQ ID NO 564
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 564
gagcgggagg cagaguuugt t                                              21

<210> SEQ ID NO 565
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 565
agcgggaggc agaguuugct t                                              21

<210> SEQ ID NO 566
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 566
gcgggaggca gaguuugcct t                                              21

<210> SEQ ID NO 567
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 567
cgggaggcag aguuugccut t                                              21

<210> SEQ ID NO 568
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 568
gggaggcaga guuugccuut t                                              21

<210> SEQ ID NO 569
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 569
ggaggcagag uuugccuuct t                                              21

<210> SEQ ID NO 570
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 570
gaggcagagu uugccuucct t                                              21

<210> SEQ ID NO 571
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 571
aggcagaguu ugccuuccut t                                              21

<210> SEQ ID NO 572
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 572
ggcagaguuu gccuuccuut t                                              21

<210> SEQ ID NO 573
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 573
gcagaguuug ccuuccuuut t                                              21

<210> SEQ ID NO 574
<211> LENGTH: 21
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: Description of Combined DNA/RNA Molecule:
      Synthetic oligonucleotide

<400> SEQUENCE: 574
cagaguuugc cuuccuuuct t                                              21

<210> SEQ ID NO 575
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 575
agaguuugcc uuccuuucut t                                              21

<210> SEQ ID NO 576
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 576
gaguuugccu uccuuucuct t                                              21

<210> SEQ ID NO 577
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 577
aguuugccuu ccuuucucct t                                              21

<210> SEQ ID NO 578
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 578
guuugccuuc cuuucuccat t                                              21

<210> SEQ ID NO 579
<211> LENGTH: 21
<212> TYPE: DNA
<213> ORGANISM: Artificial Sequence
<220> FEATURE:

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 579
uuugccuucc uuucuccagt t                                           21

<210> SEQ ID NO 580
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 580
uugccuuccu uucuccaggt t                                           21

<210> SEQ ID NO 581
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 581
ugccuuccuu ucuccaggat t                                           21

<210> SEQ ID NO 582
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 582
gccuuccuuu cuccaggact t                                           21

<210> SEQ ID NO 583
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 583
ccuuccuuuc uccaggacct t                                           21

<210> SEQ ID NO 584
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 584
cuuccuuucu ccaggaccat t                                            21

<210> SEQ ID NO 585
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 585
uuccuuucuc caggaccaat t                                            21

<210> SEQ ID NO 586
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 586
uccuuucucc aggaccaaut t                                            21

<210> SEQ ID NO 587
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 587
ccuuucucca ggaccaauat t                                            21

<210> SEQ ID NO 588
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 588
cuuucuccag gaccaauaat t                                            21

<210> SEQ ID NO 589
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 589
uuucuccagg accaauaaat t                                              21

<210> SEQ ID NO 590
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 590
uucuccagga ccaauaaaat t                                              21

<210> SEQ ID NO 591
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 591
ucuccaggac caauaaaaut t                                              21

<210> SEQ ID NO 592
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 592
cuccaggacc aauaaaauut t                                              21

<210> SEQ ID NO 593
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 593
uccaggacca auaaaauuut t                                              21

<210> SEQ ID NO 594
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 594
ccaggaccaa uaaaauuuct t                                              21

<210> SEQ ID NO 595
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 595
caggaccaau aaaauuucut t                                              21

<210> SEQ ID NO 596
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 596
aggaccaaua aaauuucuat t                                              21

<210> SEQ ID NO 597
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 597
ggaccaauaa aauuucuaat t                                              21

<210> SEQ ID NO 598
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 598
gaccaauaaa auuucuaagt t                                              21

<210> SEQ ID NO 599
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 599
accaauaaaa uuucuaagat t                                              21

<210> SEQ ID NO 600
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 600
ccaauaaaau uucuaagagt t                                              21

<210> SEQ ID NO 601
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 601
caauaaaauu ucuaagagat t                                              21

<210> SEQ ID NO 602
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 602
aauaaaauuu cuaagagagt t                                              21

<210> SEQ ID NO 603
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 603
auaaaauuuc uaagagagct t                                              21
```

```
<210> SEQ ID NO 604
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 604
uaaaauuucu aagagagcut t                                          21

<210> SEQ ID NO 605
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 605
aaaauuucua agagagcuat t                                          21

<210> SEQ ID NO 606
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 606
aaauuucuaa gagagcuaat t                                          21

<210> SEQ ID NO 607
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 607
aauuucuaag agagcuaaat t                                          21

<210> SEQ ID NO 608
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 608
auuucuaaga gagcuaaaat t                                          21
```

<210> SEQ ID NO 609
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 609
ugguggcgaa gacugcggcg g                                              21

<210> SEQ ID NO 610
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 610
augguggcga agacugcggc g                                              21

<210> SEQ ID NO 611
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 611
caugguggcg aagacugcgg c                                              21

<210> SEQ ID NO 612
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 612
gcaugguggc gaagacugcg g                                              21

<210> SEQ ID NO 613
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 613
ggcauggugg cgaagacugc g                                              21

<210> SEQ ID NO 614
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 614
cggcauggug gcgaagacug c                                              21

<210> SEQ ID NO 615
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 615
gcggcauggu ggcgaagact g                                              21

<210> SEQ ID NO 616
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 616
ggcggcaugg uggcgaagac t                                              21

<210> SEQ ID NO 617
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 617
gggcggcaug guggcgaaga c                                              21

<210> SEQ ID NO 618
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 618

-continued agggcggcau gguggcgaag a                                           21

<210> SEQ ID NO 619
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 619
uagggcggca ugguggcgaa g                                           21

<210> SEQ ID NO 620
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 620
guagggcggc augguggcga a                                           21

<210> SEQ ID NO 621
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 621
uguagggcgg caugguggcg a                                           21

<210> SEQ ID NO 622
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 622
guguagggcg gcaugguggc g                                           21

<210> SEQ ID NO 623
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 623
gguguagggc ggcauggugg c                               21

<210> SEQ ID NO 624
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 624
cgguguaggg cggcauggug g                               21

<210> SEQ ID NO 625
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 625
acgguguagg gcggcauggt g                               21

<210> SEQ ID NO 626
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 626
cacgguguag ggcggcaugg t                               21

<210> SEQ ID NO 627
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 627
ccacggugua gggcggcaug g                               21

<210> SEQ ID NO 628
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 628
accacggugu agggcggcat g                                      21

<210> SEQ ID NO 629
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 629
gaccacggug uagggcggca t                                      21

<210> SEQ ID NO 630
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 630
agaccacggu guagggcggc a                                      21

<210> SEQ ID NO 631
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 631
uagaccacgg uguagggcgg c                                      21

<210> SEQ ID NO 632
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 632
auagaccacg guguagggcg g                                      21

<210> SEQ ID NO 633
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 633
aauagaccac gguguagggc g          21

<210> SEQ ID NO 634
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 634
aaauagacca cgguguaggg c          21

<210> SEQ ID NO 635
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 635
gaaauagacc acgguguagg g          21

<210> SEQ ID NO 636
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 636
ggaaauagac cacgguguag g          21

<210> SEQ ID NO 637
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 637
gggaaauaga ccacggugua g          21

<210> SEQ ID NO 638
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 638
ugggaaauag accacggugt a					21

<210> SEQ ID NO 639
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 639
cugggaaaua gaccacggug t					21

<210> SEQ ID NO 640
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 640
acugggaaau agaccacggt g					21

<210> SEQ ID NO 641
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 641
aacugggaaa uagaccacgg t					21

<210> SEQ ID NO 642
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic
      oligonucleotide

<400> SEQUENCE: 642
gaacugggaa auagaccacg g					21

<210> SEQ ID NO 643
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 643
cgaacuggga aauagaccac g                                              21

<210> SEQ ID NO 644
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 644
ucgaacuggg aaauagacca c                                              21

<210> SEQ ID NO 645
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 645
cucgaacugg gaaauagacc a                                              21

<210> SEQ ID NO 646
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 646
ccucgaacug ggaaauagac c                                              21

<210> SEQ ID NO 647
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 647
gccucgaacu gggaaauaga c                                              21

<210> SEQ ID NO 648
<211> LENGTH: 21
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: Description of Combined DNA/RNA Molecule:
      Synthetic oligonucleotide

<400> SEQUENCE: 648
ggccucgaac ugggaaauag a                                          21

<210> SEQ ID NO 649
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 649
cggccucgaa cugggaaaua g                                          21

<210> SEQ ID NO 650
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 650
gcggccucga acugggaaat a                                          21

<210> SEQ ID NO 651
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 651
agcggccucg aacugggaaa t                                          21

<210> SEQ ID NO 652
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 652
cagcggccuc gaacugggaa a                                          21

<210> SEQ ID NO 653
<211> LENGTH: 21
<212> TYPE: DNA
<213> ORGANISM: Artificial Sequence
<220> FEATURE:

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 653
gcagcggccu cgaacuggga a                                              21

<210> SEQ ID NO 654
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 654
cgcagcggcc ucgaacuggg a                                              21

<210> SEQ ID NO 655
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 655
gcgcagcggc cucgaacugg g                                              21

<210> SEQ ID NO 656
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 656
cgcgcagcgg ccucgaacug g                                              21

<210> SEQ ID NO 657
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 657
ccgcgcagcg gccucgaact g                                              21

<210> SEQ ID NO 658
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 658
gccgcgcagc ggccucgaac t                                              21

<210> SEQ ID NO 659
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 659
ggccgcgcag cggccucgaa c                                              21

<210> SEQ ID NO 660
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 660
gggccgcgca gcggccucga a                                              21

<210> SEQ ID NO 661
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 661
agggccgcgc agcggccucg a                                              21

<210> SEQ ID NO 662
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 662
cagggccgcg cagcggccuc g                                              21

<210> SEQ ID NO 663
<211> LENGTH: 21
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 663
gcagggccgc gcagcggcct c                                              21

<210> SEQ ID NO 664
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 664
cgcagggccg cgcagcggcc t                                              21

<210> SEQ ID NO 665
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 665
gcgcagggcc gcgcagcggc c                                              21

<210> SEQ ID NO 666
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 666
ugcgcagggc cgcgcagcgg c                                              21

<210> SEQ ID NO 667
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 667
augcgcaggg ccgcgcagcg g                                              21

<210> SEQ ID NO 668
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 668
caugcgcagg gccgcgcagc g                                              21

<210> SEQ ID NO 669
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 669
gcaugcgcag ggccgcgcag c                                              21

<210> SEQ ID NO 670
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic
      oligonucleotide

<400> SEQUENCE: 670
agcaugcgca gggccgcgca g                                              21

<210> SEQ ID NO 671
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 671
cagcaugcgc agggccgcgc a                                              21

<210> SEQ ID NO 672
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 672
gcagcaugcg cagggccgcg c                                              21
```

```
<210> SEQ ID NO 673
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 673
agcagcaugc gcagggccgc g                                              21

<210> SEQ ID NO 674
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 674
cagcagcaug cgcagggccg c                                              21

<210> SEQ ID NO 675
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 675
ccagcagcau gcgcagggcc g                                              21

<210> SEQ ID NO 676
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 676
gccagcagca ugcgcagggc c                                              21

<210> SEQ ID NO 677
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 677
ugccagcagc augcgcaggg c                                              21
```

<210> SEQ ID NO 678
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 678
cugccagcag caugcgcagg g                                              21

<210> SEQ ID NO 679
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 679
ucugccagca gcaugcgcag g                                              21

<210> SEQ ID NO 680
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 680
aucugccagc agcaugcgca g                                              21

<210> SEQ ID NO 681
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 681
gaucugccag cagcaugcgc a                                              21

<210> SEQ ID NO 682
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 682
ugaucugcca gcagcaugcg c                                              21

<210> SEQ ID NO 683
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 683
cugaucugcc agcagcaugc g                                              21

<210> SEQ ID NO 684
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 684
ccugaucugc cagcagcaug c                                              21

<210> SEQ ID NO 685
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 685
cccugaucug ccagcagcat g                                              21

<210> SEQ ID NO 686
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 686
gcccugaucu gccagcagca t                                              21

<210> SEQ ID NO 687
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 687
ggcccugauc ugccagcagc a                          21

<210> SEQ ID NO 688
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 688
uggcccugau cugccagcag c                          21

<210> SEQ ID NO 689
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 689
cuggcccuga ucugccagca g                          21

<210> SEQ ID NO 690
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 690
ucuggcccug aucugccagc a                          21

<210> SEQ ID NO 691
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 691
cucuggcccu gaucugccag c                          21

<210> SEQ ID NO 692
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 692
gcucuggccc ugaucugcca g                                              21

<210> SEQ ID NO 693
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 693
agcucuggcc cugaucugcc a                                              21

<210> SEQ ID NO 694
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 694
cagcucuggc ccugaucugc c                                              21

<210> SEQ ID NO 695
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 695
ccagcucugg cccugaucug c                                              21

<210> SEQ ID NO 696
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 696
uccagcucug gcccugauct g                                              21

<210> SEQ ID NO 697
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 697
uuccagcucu ggcccugauc t    21

<210> SEQ ID NO 698
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 698
cuuccagcuc uggcccugat c    21

<210> SEQ ID NO 699
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 699
ccuuccagcu cuggcccuga t    21

<210> SEQ ID NO 700
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 700
uccuuccagc ucuggcccug a    21

<210> SEQ ID NO 701
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 701
cuccuuccag cucuggccct g    21

<210> SEQ ID NO 702
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 702
ccuccuucca gcucuggccc t                                              21

<210> SEQ ID NO 703
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 703
uccuccuucc agcucuggcc c                                              21

<210> SEQ ID NO 704
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 704
cuccuccuuc cagcucuggc c                                              21

<210> SEQ ID NO 705
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 705
ccuccuccuu ccagcucugg c                                              21

<210> SEQ ID NO 706
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 706
accuccuccu uccagcucug g                                              21

<210> SEQ ID NO 707
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide

<400> SEQUENCE: 707
caccuccucc uuccagcuct g    21

<210> SEQ ID NO 708
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 708
uaccuccucc uuccagcuct g    21

<210> SEQ ID NO 709
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 709
ccaccuccuc cuuccagcuc t    21

<210> SEQ ID NO 710
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 710
accaccuccu ccuuccagct c    21

<210> SEQ ID NO 711
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic
      oligonucleotide

<400> SEQUENCE: 711
caccaccucc uccuuccagc t    21

<210> SEQ ID NO 712
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 712
ucaccaccuc cuccuuccag c                                              21

<210> SEQ ID NO 713
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 713
gucaccaccu ccuccuucca g                                              21

<210> SEQ ID NO 714
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 714
ggucaccacc uccuccuucc a                                              21

<210> SEQ ID NO 715
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 715
cggucaccac cuccuccuuc c                                              21

<210> SEQ ID NO 716
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 716
acggucacca ccuccuccut c                                              21

<210> SEQ ID NO 717
<211> LENGTH: 21
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: Description of Combined DNA/RNA Molecule:
      Synthetic oligonucleotide

<400> SEQUENCE: 717
cacggucacc accuccucct t                                                 21

<210> SEQ ID NO 718
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 718
ccacggucac caccuccucc t                                                 21

<210> SEQ ID NO 719
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 719
uccacgguca ccaccuccuc c                                                 21

<210> SEQ ID NO 720
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 720
cuccacgguc accaccucct c                                                 21

<210> SEQ ID NO 721
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 721
ucuccacggu caccaccucc t                                                 21

<210> SEQ ID NO 722
<211> LENGTH: 21
<212> TYPE: DNA
<213> ORGANISM: Artificial Sequence
<220> FEATURE:

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 722
gucuccacgg ucaccaccuc c                                            21

<210> SEQ ID NO 723
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 723
cgucuccacg gucaccacct c                                            21

<210> SEQ ID NO 724
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 724
acgucuccac ggucaccacc t                                            21

<210> SEQ ID NO 725
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 725
cacgucucca cggucaccac c                                            21

<210> SEQ ID NO 726
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 726
ccacgucucc acggucacca c                                            21

<210> SEQ ID NO 727
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 727
gccacgucuc cacggucacc a                                               21

<210> SEQ ID NO 728
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 728
ugccacgucu ccacggucac c                                               21

<210> SEQ ID NO 729
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 729
cugccacguc uccacgguca c                                               21

<210> SEQ ID NO 730
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 730
ccugccacgu cuccacgguc a                                               21

<210> SEQ ID NO 731
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 731
uccugccacg ucuccacggt c                                               21

<210> SEQ ID NO 732
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 732
cuccugccac gucuccacgg t                                          21

<210> SEQ ID NO 733
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 733
ccuccugcca cgucuccacg g                                          21

<210> SEQ ID NO 734
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 734
cccuccugcc acgucuccac g                                          21

<210> SEQ ID NO 735
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 735
gcccuccugc cacgucucca c                                          21

<210> SEQ ID NO 736
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 736
agcccuccug ccacgucucc a                                          21

<210> SEQ ID NO 737
<211> LENGTH: 21
```

<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 737
gagcccuccu gccacgucuc c                                            21

<210> SEQ ID NO 738
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 738
ugagcccucc ugccacguct c                                            21

<210> SEQ ID NO 739
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 739
gugagcccuc cugccacguc t                                            21

<210> SEQ ID NO 740
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 740
agugagcccu ccugccacgt c                                            21

<210> SEQ ID NO 741
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 741
gagugagccc uccugccacg t                                            21

<210> SEQ ID NO 742

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 742
ugagugagcc cuccugccac g                                              21

<210> SEQ ID NO 743
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 743
uugagugagc ccuccugcca c                                              21

<210> SEQ ID NO 744
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 744
uuugagugag cccuccugcc a                                              21

<210> SEQ ID NO 745
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 745
cuuugaguga gcccuccugc c                                              21

<210> SEQ ID NO 746
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 746
gcuuugagug agcccuccug c                                              21
```

<210> SEQ ID NO 747
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 747
ggcuuugagu gagcccucct g                              21

<210> SEQ ID NO 748
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 748
aggcuuugag ugagcccucc t                              21

<210> SEQ ID NO 749
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 749
gaggcuuuga gugagcccuc c                              21

<210> SEQ ID NO 750
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 750
ggaggcuuug agugagccct c                              21

<210> SEQ ID NO 751
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 751
aggaggcuuu gagugagccc t                              21

<210> SEQ ID NO 752
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 752
caggaggcuu ugagugagcc c                                              21

<210> SEQ ID NO 753
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 753
gcaggaggcu uugagugagc c                                              21

<210> SEQ ID NO 754
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 754
ggcaggaggc uuugagugag c                                              21

<210> SEQ ID NO 755
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 755
aggcaggagg cuuugaguga g                                              21

<210> SEQ ID NO 756
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 756
uaggcaggag gcuuugagug a    21

<210> SEQ ID NO 757
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 757
auaggcagga ggcuuugagt g    21

<210> SEQ ID NO 758
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 758
uauaggcagg aggcuuugag t    21

<210> SEQ ID NO 759
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 759
guauaggcag gaggcuuuga g    21

<210> SEQ ID NO 760
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 760
cguauaggca ggaggcuuug a    21

<210> SEQ ID NO 761
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 761
ccguauaggc aggaggcuut g                                              21

<210> SEQ ID NO 762
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 762
cccguauagg caggaggcut t                                              21

<210> SEQ ID NO 763
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 763
gcccguauag gcaggaggct t                                              21

<210> SEQ ID NO 764
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 764
ugcccguaua ggcaggaggc t                                              21

<210> SEQ ID NO 765
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 765
cugcccguau aggcaggagg c                                              21

<210> SEQ ID NO 766
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 766
gcugcccgua uaggcaggag g                                              21

<210> SEQ ID NO 767
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 767
agcugcccgu auaggcagga g                                              21

<210> SEQ ID NO 768
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 768
gagcugcccg uauaggcagg a                                              21

<210> SEQ ID NO 769
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 769
ggagcugccc guauaggcag g                                              21

<210> SEQ ID NO 770
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 770
gggagcugcc cguauaggca g                                              21

<210> SEQ ID NO 771
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 771
cuccguccug gaacuugggg a                                              21

<210> SEQ ID NO 772
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 772
ucuccguccu ggaacuuggg g                                              21

<210> SEQ ID NO 773
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 773
gucuccgucc uggaacuugg g                                              21

<210> SEQ ID NO 774
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 774
ggucuccguc cuggaacuug g                                              21

<210> SEQ ID NO 775
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 775
aggucuccgu ccuggaacut g                                              21

<210> SEQ ID NO 776
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 776
gaggucuccg uccuggaact t                                              21

<210> SEQ ID NO 777
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 777
ugaggucucc guccuggaac t                                              21

<210> SEQ ID NO 778
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 778
gugaggucuc cguccuggaa c                                              21

<210> SEQ ID NO 779
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 779
ggugaggucu ccguccugga a                                              21

<210> SEQ ID NO 780
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 780
gggugagguc uccguccugg a                                              21

<210> SEQ ID NO 781
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: Description of Combined DNA/RNA Molecule:
       Synthetic oligonucleotide

<400> SEQUENCE: 781
agggugaggu cuccguccug g                                                    21

<210> SEQ ID NO 782
<211> LENGTH: 21
<212> TYPE: DNA
<213> ORGANISM: Artificial Sequence
<220> FEATURE:
<223> OTHER INFORMATION: Description of Artificial Sequence: Synthetic
       oligonucleotide
<220> FEATURE:
<223> OTHER INFORMATION: Description of Combined DNA/RNA Molecule:
       Synthetic oligonucleotide

<400> SEQUENCE: 782
cagggugagg ucuccguccu g                                                    21

<210> SEQ ID NO 783
<211> LENGTH: 21
<212> TYPE: DNA
<213> ORGANISM: Artificial Sequence
<220> FEATURE:
<223> OTHER INFORMATION: Description of Artificial Sequence: Synthetic
       oligonucleotide
<220> FEATURE:
<223> OTHER INFORMATION: Description of Combined DNA/RNA Molecule:
       Synthetic oligonucleotide

<400> SEQUENCE: 783
acagggugag gucuccgucc t                                                    21

<210> SEQ ID NO 784
<211> LENGTH: 21
<212> TYPE: DNA
<213> ORGANISM: Artificial Sequence
<220> FEATURE:
<223> OTHER INFORMATION: Description of Artificial Sequence: Synthetic
       oligonucleotide
<220> FEATURE:
<223> OTHER INFORMATION: Description of Combined DNA/RNA Molecule:
       Synthetic oligonucleotide

<400> SEQUENCE: 784
uacaggguga ggucuccguc c                                                    21

<210> SEQ ID NO 785
<211> LENGTH: 21
<212> TYPE: DNA
<213> ORGANISM: Artificial Sequence
<220> FEATURE:
<223> OTHER INFORMATION: Description of Artificial Sequence: Synthetic
       oligonucleotide
<220> FEATURE:
<223> OTHER INFORMATION: Description of Combined DNA/RNA Molecule:
       Synthetic oligonucleotide

<400> SEQUENCE: 785
guacagggug aggucuccgt c                                                    21

<210> SEQ ID NO 786
<211> LENGTH: 21
<212> TYPE: DNA
<213> ORGANISM: Artificial Sequence
<220> FEATURE:
<223> OTHER INFORMATION: Description of Artificial Sequence: Synthetic
       oligonucleotide

```
<220> FEATURE:
<223> OTHER INFORMATION: Description of Combined DNA/RNA Molecule:
      Synthetic oligonucleotide

<400> SEQUENCE: 786
gguacagggu gaggucuccg t                                              21

<210> SEQ ID NO 787
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 787
ugguacaggg ugaggucucc g                                              21

<210> SEQ ID NO 788
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 788
cugguacagg gugaggucuc c                                              21

<210> SEQ ID NO 789
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 789
acugguacag ggugagguct c                                              21

<210> SEQ ID NO 790
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 790
gacugguaca gggugagguc t                                              21

<210> SEQ ID NO 791
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
      oligonucleotide
<220> FEATURE:
<223> OTHER INFORMATION: Description of Combined DNA/RNA Molecule:
      Synthetic oligonucleotide

<400> SEQUENCE: 791
ggacuggvac agggugaggt c                                            21

<210> SEQ ID NO 792
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 792
uggacuggua cagggugagg t                                            21

<210> SEQ ID NO 793
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 793
uuggacuggu acagggugag g                                            21

<210> SEQ ID NO 794
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 794
auuggacugg uacaggguga g                                            21

<210> SEQ ID NO 795
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 795
uauuggacug guacagggug a                                            21

<210> SEQ ID NO 796
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 796
guauuggacu gguacagggt g                                              21

<210> SEQ ID NO 797
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 797
gguauuggac ugguacaggg t                                              21

<210> SEQ ID NO 798
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 798
ugguauugga cugguacagg g                                              21

<210> SEQ ID NO 799
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 799
augguauugg acugguacag g                                              21

<210> SEQ ID NO 800
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 800
gaugguauug gacugguaca g                                              21

<210> SEQ ID NO 801
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 801
ggaugguauu ggacugguac a                                              21

<210> SEQ ID NO 802
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 802
aggaugguau uggacuggua c                                              21

<210> SEQ ID NO 803
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 803
caggauggua uuggacuggt a                                              21

<210> SEQ ID NO 804
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 804
gcaggauggu auuggacugg t                                              21

<210> SEQ ID NO 805
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 805
cgcaggaugg uauuggacug g                                              21

<210> SEQ ID NO 806
<211> LENGTH: 21
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 806
acgcaggaug guauuggact g                                              21

<210> SEQ ID NO 807
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 807
gacgcaggau gguauuggac t                                              21

<210> SEQ ID NO 808
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 808
ugacgcagga ugguauugga c                                              21

<210> SEQ ID NO 809
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 809
gugacgcagg augguauugg a                                              21

<210> SEQ ID NO 810
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 810
ggugacgcag gaugguauug g                                              21

<210> SEQ ID NO 811
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 811
aggugacgca ggaugguaut g                                           21

<210> SEQ ID NO 812
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 812
caggugacgc aggaugguat t                                           21

<210> SEQ ID NO 813
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 813
ccaggugacg caggauggua t                                           21

<210> SEQ ID NO 814
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 814
cccaggugac gcaggauggt a                                           21

<210> SEQ ID NO 815
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 815
gcccagguga cgcaggaugg t                                           21

<210> SEQ ID NO 816
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 816
ggcccaggug acgcaggaug g                                             21

<210> SEQ ID NO 817
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 817
cggcccaggu gacgcaggat g                                             21

<210> SEQ ID NO 818
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 818
gcggcccagg ugacgcagga t                                             21

<210> SEQ ID NO 819
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 819
ugcggcccag gugacgcagg a                                             21

<210> SEQ ID NO 820
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 820
gugcggccca ggugacgcag g                                             21
```

```
<210> SEQ ID NO 821
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 821
ggugcggccc aggugacgca g                                               21

<210> SEQ ID NO 822
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 822
gggugcggcc caggugacgc a                                               21

<210> SEQ ID NO 823
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 823
agggugcggc ccaggugacg c                                               21

<210> SEQ ID NO 824
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 824
aagggugcgg cccaggugac g                                               21

<210> SEQ ID NO 825
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 825
caagggugcg gcccagguga c                                               21
```

```
<210> SEQ ID NO 826
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 826
ccaagggugc ggcccaggug a                                              21

<210> SEQ ID NO 827
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 827
cccaagggug cggcccaggt g                                              21

<210> SEQ ID NO 828
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 828
gcccaagggu gcggcccagg t                                              21

<210> SEQ ID NO 829
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 829
agcccaaggg ugcggcccag g                                              21

<210> SEQ ID NO 830
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 830
gagcccaagg gugcggccca g                                              21
```

<210> SEQ ID NO 831
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 831
agagcccaag ggugcggccc a                                              21

<210> SEQ ID NO 832
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 832
uagagcccaa gggugcggcc c                                              21

<210> SEQ ID NO 833
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 833
auagagccca agggugcggc c                                              21

<210> SEQ ID NO 834
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 834
cauagagccc aagggugcgg c                                              21

<210> SEQ ID NO 835
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 835
ccauagagcc caagggugcg g         21

<210> SEQ ID NO 836
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 836
cccauagagc caagggugc g         21

<210> SEQ ID NO 837
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 837
ucccauagag cccaagggug c         21

<210> SEQ ID NO 838
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 838
uucccauaga gcccaagggt g         21

<210> SEQ ID NO 839
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 839
cuucccauag agcccaaggg t         21

<210> SEQ ID NO 840
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 840
ccuucccaua gagcccaagg g                                              21

<210> SEQ ID NO 841
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 841
uccuucccau agagcccaag g                                              21

<210> SEQ ID NO 842
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 842
guccuuccca uagagcccaa g                                              21

<210> SEQ ID NO 843
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 843
gguccuuccc auagagccca a                                              21

<210> SEQ ID NO 844
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 844
ugguccuucc cauagagccc a                                              21

<210> SEQ ID NO 845
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 845
cugguccuuc ccauagagcc c                                              21

<210> SEQ ID NO 846
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 846
gcugguccuu cccauagagc c                                              21

<210> SEQ ID NO 847
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 847
ugcugguccu ucccauagag c                                              21

<210> SEQ ID NO 848
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 848
cugcuggucc uucccauaga g                                              21

<210> SEQ ID NO 849
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 849
ccugcugguc cuucccauag a                                              21

<210> SEQ ID NO 850
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 850
uccugcuggu ccuucccaua g					21

<210> SEQ ID NO 851
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 851
cuccugcugg uccuucccat a					21

<210> SEQ ID NO 852
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 852
ccuccugcug guccuuccca t					21

<210> SEQ ID NO 853
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 853
gccuccugcu gguccuuccc a					21

<210> SEQ ID NO 854
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 854
ugccuccugc ugguccuucc c					21

<210> SEQ ID NO 855
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 855
cugccuccug cugguccuuc c                                              21

<210> SEQ ID NO 856
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 856
gcugccuccu gcugguccut c                                              21

<210> SEQ ID NO 857
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 857
ggcugccucc ugcuggucct t                                              21

<210> SEQ ID NO 858
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 858
gggcugccuc cugcuggucc t                                              21

<210> SEQ ID NO 859
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 859
agggcugccu ccugcugguc c                                              21

<210> SEQ ID NO 860
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 860
cagggcugcc uccugcuggt c                                              21

<210> SEQ ID NO 861
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 861
ccagggcugc cuccugcugg t                                              21

<210> SEQ ID NO 862
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 862
accagggcug ccuccugcug g                                              21

<210> SEQ ID NO 863
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 863
caccagggcu gccuccugct g                                              21

<210> SEQ ID NO 864
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 864
ccaccagggc ugccuccugc t                                              21

<210> SEQ ID NO 865
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 865
uccaccaggg cugccuccug c                                              21

<210> SEQ ID NO 866
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 866
guccaccagg gcugccucct g                                              21

<210> SEQ ID NO 867
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 867
uguccaccag ggcugccucc t                                              21

<210> SEQ ID NO 868
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 868
auguccacca gggcugccuc c                                              21

<210> SEQ ID NO 869
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 869
cauguccacc agggcugcct c                                              21

<210> SEQ ID NO 870
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
        oligonucleotide
<220> FEATURE:
<223> OTHER INFORMATION: Description of Combined DNA/RNA Molecule:
      Synthetic oligonucleotide

<400> SEQUENCE: 870
ccauguccac cagggcugcc t                                            21

<210> SEQ ID NO 871
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 871
accaugucca ccagggcugc c                                            21

<210> SEQ ID NO 872
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 872
caccaugucc accagggcug c                                            21

<210> SEQ ID NO 873
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 873
ucaccauguc caccagggct g                                            21

<210> SEQ ID NO 874
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 874 uuccaccaugu ccaccagggc t                                           21

<210> SEQ ID NO 875
<211> LENGTH: 21
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 875
auucaccaug uccaccaggg c                                            21

<210> SEQ ID NO 876
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 876
cauucaccau guccaccagg g                                            21

<210> SEQ ID NO 877
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 877
ucauucacca uguccaccag g                                            21

<210> SEQ ID NO 878
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 878
gucauucacc auguccacca g                                            21

<210> SEQ ID NO 879
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 879
cgucauucac cauguccacc a                                            21

<210> SEQ ID NO 880
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 880
ccgucauuca ccauguccac c                                           21

<210> SEQ ID NO 881
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 881
gccgucauuc accaugucca c                                           21

<210> SEQ ID NO 882
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 882
cgccgucauu caccaugucc a                                           21

<210> SEQ ID NO 883
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 883
acgccgucau ucaccauguc c                                           21

<210> SEQ ID NO 884
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 884
cacgccguca uuccaccaugt c                                          21

<210> SEQ ID NO 885
<211> LENGTH: 21
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 885
ccacgccguc auucaccaug t                                              21

<210> SEQ ID NO 886
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 886
uccacgccgu cauucaccat g                                              21

<210> SEQ ID NO 887
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 887
cuccacgccg ucauucacca t                                              21

<210> SEQ ID NO 888
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 888
ccuccacgcc gucauucacc a                                              21

<210> SEQ ID NO 889
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 889
uccuccacgc cgucauucac c                                              21

<210> SEQ ID NO 890
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 890
guccuccacg ccgucauuca c                                              21

<210> SEQ ID NO 891
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 891
gguccuccac gccgucauuc a                                              21

<210> SEQ ID NO 892
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 892
agguccucca cgccgucaut c                                              21

<210> SEQ ID NO 893
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 893
gagguccucc acgccgucat t                                              21

<210> SEQ ID NO 894
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 894
ggagguccuc cacgccguca t                                              21

<210> SEQ ID NO 895
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 895
cggagguccu ccacgccguc a                                          21

<210> SEQ ID NO 896
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 896
gcggaggucc uccacgccgt c                                          21

<210> SEQ ID NO 897
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 897
agcggagguc cuccacgccg t                                          21

<210> SEQ ID NO 898
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 898
cagcggaggu ccuccacgcc g                                          21

<210> SEQ ID NO 899
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 899
gcagcggagg uccuccacgc c                                          21
```

```
<210> SEQ ID NO 900
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 900
ugcagcggag guccuccacg c                                              21

<210> SEQ ID NO 901
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 901
uugcagcgga gguccuccac g                                              21

<210> SEQ ID NO 902
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 902
uuugcagcgg agguccucca c                                              21

<210> SEQ ID NO 903
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 903
auuugcagcg gagguccucc a                                              21

<210> SEQ ID NO 904
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 904
uauuugcagc ggagguccuc c                                              21
```

<210> SEQ ID NO 905
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 905
guauuugcag cggagguccu c                                              21

<210> SEQ ID NO 906
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 906
uguauuugca gcggaggucc t                                              21

<210> SEQ ID NO 907
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 907
auguauuugc agcggagguc c                                              21

<210> SEQ ID NO 908
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 908
gauguauuug cagcggaggt c                                              21

<210> SEQ ID NO 909
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 909
agauguauuu gcagcggagg t                                              21

<210> SEQ ID NO 910
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 910
gagauguauu ugcagcggag g                                            21

<210> SEQ ID NO 911
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 911
ggagauguau uugcagcgga g                                            21

<210> SEQ ID NO 912
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 912
gggagaugua uuugcagcgg a                                            21

<210> SEQ ID NO 913
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 913
agggagaugu auuugcagcg g                                            21

<210> SEQ ID NO 914
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 914
gagggagaug uauuugcagc g                                              21

<210> SEQ ID NO 915
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 915
ugagggagau guauuugcag c                                              21

<210> SEQ ID NO 916
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 916
augagggaga uguauuugca g                                              21

<210> SEQ ID NO 917
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 917
gaugagggag auguauuugc a                                              21

<210> SEQ ID NO 918
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 918
agaugaggga gauguauuug c                                              21

<210> SEQ ID NO 919
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 919
uagaugaggg agauguauut g                                            21

<210> SEQ ID NO 920
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 920
guagaugagg gagauguaut t                                            21

<210> SEQ ID NO 921
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 921
uguagaugag ggagauguat t                                            21

<210> SEQ ID NO 922
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 922
guguagauga gggagaugua t                                            21

<210> SEQ ID NO 923
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 923
gguguagaug agggagaugt a                                            21

<210> SEQ ID NO 924
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 924
ugguguagau gagggagaug t                                              21

<210> SEQ ID NO 925
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 925
uugguguaga ugagggagat g                                              21

<210> SEQ ID NO 926
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 926
uugguguaga ugagggagct g                                              21

<210> SEQ ID NO 927
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 927
guugguguag augagggaga t                                              21

<210> SEQ ID NO 928
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 928
aguuggugua gaugagggag a                                              21

<210> SEQ ID NO 929
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 929
uuugguguag augagggaga t                                                    21

<210> SEQ ID NO 930
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 930
uaguuggugu agaugaggga g                                                    21

<210> SEQ ID NO 931
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 931
auaguuggug uagaugaggg a                                                    21

<210> SEQ ID NO 932
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 932
uuaguuggug uagaugaggg a                                                    21

<210> SEQ ID NO 933
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 933
cauaguuggu guagaugagg g                                                    21

<210> SEQ ID NO 934
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

-continued

Synthetic oligonucleotide

<400> SEQUENCE: 934
ucauaguugg uguagaugag g                                           21

<210> SEQ ID NO 935
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 935
cucauaguug guguagauga g                                           21

<210> SEQ ID NO 936
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 936
ccucauaguu gguguagaug a                                           21

<210> SEQ ID NO 937
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 937
gccucauagu ugguguagat g                                           21

<210> SEQ ID NO 938
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 938
cgccucauag uugguguaga t                                           21

<210> SEQ ID NO 939
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: Description of Combined DNA/RNA Molecule:
      Synthetic oligonucleotide

<400> SEQUENCE: 939
ccgccucaua guugguguag a                                              21

<210> SEQ ID NO 940
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 940
cccgccucau aguuggugua g                                              21

<210> SEQ ID NO 941
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 941
gcccgccuca uaguuggugt a                                              21

<210> SEQ ID NO 942
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 942
ugcccgccuc auaguuggug t                                              21

<210> SEQ ID NO 943
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 943
uugcccgccu cauaguuggt g                                              21

<210> SEQ ID NO 944
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 944
cuugcccgcc ucauaguugg t                                              21

<210> SEQ ID NO 945
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 945
ccuugcccgc cucauaguug g                                              21

<210> SEQ ID NO 946
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 946
uccuugcccg ccucauagut g                                              21

<210> SEQ ID NO 947
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 947
auccuugccc gccucauagt t                                              21

<210> SEQ ID NO 948
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 948
cauccuugcc cgccucauag t                                              21

<210> SEQ ID NO 949
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
            oligonucleotide
<220> FEATURE:
<223> OTHER INFORMATION: Description of Combined DNA/RNA Molecule:
      Synthetic oligonucleotide

<400> SEQUENCE: 949
ucauccuugc ccgccucaua g                                           21

<210> SEQ ID NO 950
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 950
gucauccuug cccgccucat a                                           21

<210> SEQ ID NO 951
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 951
agucauccuu gcccgccuca t                                           21

<210> SEQ ID NO 952
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 952
uagucauccu ugcccgccuc a                                           21

<210> SEQ ID NO 953
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 953
auagucaucc uugcccgcct c                                           21

<210> SEQ ID NO 954
<211> LENGTH: 21
<212> TYPE: DNA
<213> ORGANISM: Artificial Sequence
<220> FEATURE:
```

<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 954
cauagucauc cuugcccgcc t                                              21

<210> SEQ ID NO 955
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 955
acauagucau ccuugcccgc c                                              21

<210> SEQ ID NO 956
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 956
cacauaguca uccuugcccg c                                              21

<210> SEQ ID NO 957
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 957
ucacauaguc auccuugccc g                                              21

<210> SEQ ID NO 958
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 958
uucacauagu cauccuugcc c                                              21

<210> SEQ ID NO 959
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 959
cuucacauag ucauccuugc c                                          21

<210> SEQ ID NO 960
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 960
ccuucacaua gucauccuug c                                          21

<210> SEQ ID NO 961
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 961
gccuucacau agucauccut g                                          21

<210> SEQ ID NO 962
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 962
ugccuucaca uagucaucct t                                          21

<210> SEQ ID NO 963
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 963
gugccuucac auagucaucc t                                          21

<210> SEQ ID NO 964
<211> LENGTH: 21
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 964
agugccuuca cauagucauc c                                                21

<210> SEQ ID NO 965
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 965
cagugccuuc acauagucat c                                                21

<210> SEQ ID NO 966
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 966
gcagugccuu cacauaguca t                                                21

<210> SEQ ID NO 967
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 967
ggcagugccu ucacauaguc a                                                21

<210> SEQ ID NO 968
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 968
gggcagugcc uucacauagt c                                                21

<210> SEQ ID NO 969
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 969
cgggcagugc cuucacauag t                                           21

<210> SEQ ID NO 970
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 970
ccgggcagug ccuucacaua g                                           21

<210> SEQ ID NO 971
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 971
cccgggcagu gccuucacat a                                           21

<210> SEQ ID NO 972
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 972
gcccgggcag ugccuucaca t                                           21

<210> SEQ ID NO 973
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 973
ugcccgggca gugccuucac a                                           21

<210> SEQ ID NO 974
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 974
uugcccgggc agugccuuca c                                              21

<210> SEQ ID NO 975
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 975
guugcccggg cagugccuuc a                                              21

<210> SEQ ID NO 976
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 976
aguugcccgg gcagugccut c                                              21

<210> SEQ ID NO 977
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 977
caguugcccg ggcagugcct t                                              21

<210> SEQ ID NO 978
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 978
ucaguugccc gggcagugcc t                                              21
```

```
<210> SEQ ID NO 979
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 979
uucaguugcc cgggcagugc c                                             21

<210> SEQ ID NO 980
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 980
cuucaguugc ccgggcagug c                                             21

<210> SEQ ID NO 981
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 981
gcuucaguug cccgggcagt g                                             21

<210> SEQ ID NO 982
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 982
ggcuucaguu gcccgggcag t                                             21

<210> SEQ ID NO 983
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 983
aggcuucagu ugcccgggca g                                             21
```

<210> SEQ ID NO 984
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 984
aaggcuucag uugcccgggc a                                              21

<210> SEQ ID NO 985
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 985
aaaggcuuca guugcccggg c                                              21

<210> SEQ ID NO 986
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 986
aaaaggcuuc aguugcccgg g                                              21

<210> SEQ ID NO 987
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 987
caaaaggcuu caguugcccg g                                              21

<210> SEQ ID NO 988
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 988
ucaaaaggcu ucaguugccc g                                              21

<210> SEQ ID NO 989
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 989
cucaaaaggc uucaguugcc c                                              21

<210> SEQ ID NO 990
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 990
ucucaaaagg cuucaguugc c                                              21

<210> SEQ ID NO 991
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 991
gucucaaaag gcuucaguug c                                              21

<210> SEQ ID NO 992
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 992
ggucucaaaa ggcuucagut g                                              21

<210> SEQ ID NO 993
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 993
ugucucaaaa ggcuucagut g                                      21

<210> SEQ ID NO 994
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 994
gggucucaaa aggcuucagt t                                      21

<210> SEQ ID NO 995
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 995
agggucucaa aaggcuucag t                                      21

<210> SEQ ID NO 996
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 996
cagggucuca aaaggcuuca g                                      21

<210> SEQ ID NO 997
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 997
gcagggucuc aaaaggcuuc a                                      21

<210> SEQ ID NO 998
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 998
uagggucuca aaaggcuuca g                                         21

<210> SEQ ID NO 999
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 999
agcagggucu caaaaggcut c                                         21

<210> SEQ ID NO 1000
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1000
ugcagggucu caaaaggcgt c                                         21

<210> SEQ ID NO 1001
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1001
ugcagggucu caaaaggcut c                                         21

<210> SEQ ID NO 1002
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1002
cagcagdguc ucaaaaggct t                                         21

<210> SEQ ID NO 1003
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1003
acagcagggu cucaaaaggc t                                      21

<210> SEQ ID NO 1004
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1004
ucagcagggu cucaaaaggc t                                      21

<210> SEQ ID NO 1005
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1005
gacagcaggg ucucaaaagg c                                      21

<210> SEQ ID NO 1006
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1006
uacagcaggg ucucaaaagg c                                      21

<210> SEQ ID NO 1007
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1007
ggacagcagg gucucaaaag g                                      21

<210> SEQ ID NO 1008
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide -continued

<400> SEQUENCE: 1008
gggacagcag ggucucaaaa g                                        21

<210> SEQ ID NO 1009
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1009
ugggacagca gggucucaaa a                                        21

<210> SEQ ID NO 1010
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1010
cugggacagc agggucucaa a                                        21

<210> SEQ ID NO 1011
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1011
ucugggacag cagggucuca a                                        21

<210> SEQ ID NO 1012
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1012
uucugggaca gcagggucuc a                                        21

<210> SEQ ID NO 1013
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 1013
guucugggac agcaggguct c                                              21

<210> SEQ ID NO 1014
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1014
gguucuggga cagcagdgguc t                                             21

<210> SEQ ID NO 1015
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1015
uguucuggga cagcaggguc t                                              21

<210> SEQ ID NO 1016
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1016
ugguucuggg acagcagggt c                                              21

<210> SEQ ID NO 1017
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1017
cugguucugg gacagcaggg t                                              21

<210> SEQ ID NO 1018
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 1018
ccugguucug ggacagcagg g                                              21

<210> SEQ ID NO 1019
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1019
cccugguucu gggacagcag g                                              21

<210> SEQ ID NO 1020
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1020
uccugguucu gggacagcag g                                              21

<210> SEQ ID NO 1021
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1021
ucccugguuc ugggacagca g                                              21

<210> SEQ ID NO 1022
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1022
cucccugguu cugggacagc a                                              21

<210> SEQ ID NO 1023
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 1023
ccucccuggu ucugggacag c                                              21

<210> SEQ ID NO 1024
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1024
gccucccugg uucugggaca g                                              21

<210> SEQ ID NO 1025
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1025
ugccucccug guucugggac a                                              21

<210> SEQ ID NO 1026
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1026
uugccucccu gguucuggga c                                              21

<210> SEQ ID NO 1027
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1027
cuugccuccc ugguucuggg a                                              21

<210> SEQ ID NO 1028
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
                         oligonucleotide
<220> FEATURE:
<223> OTHER INFORMATION: Description of Combined DNA/RNA Molecule:
      Synthetic oligonucleotide

<400> SEQUENCE: 1028
ucuugccucc cugguucugg g                                           21

<210> SEQ ID NO 1029
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1029
gucuugccuc ccugguucug g                                           21

<210> SEQ ID NO 1030
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1030
ggucuugccu cccugguuct g                                           21

<210> SEQ ID NO 1031
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1031
aggucuugcc ucccugguuc t                                           21

<210> SEQ ID NO 1032
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1032
aaggucuugc cucccuggut c                                           21

<210> SEQ ID NO 1033
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1033
gaaggucuug ccucccuggt t                                              21

<210> SEQ ID NO 1034
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1034
ugaaggucuu gccucccugg t                                              21

<210> SEQ ID NO 1035
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1035
augaaggucu ugccucccug g                                              21

<210> SEQ ID NO 1036
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1036
aaugaagguc uugccuccct g                                              21

<210> SEQ ID NO 1037
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1037
caaugaaggu cuugccuccc t                                              21

<210> SEQ ID NO 1038
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1038
acaaugaagg ucuugccucc c                                             21

<210> SEQ ID NO 1039
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1039
cacaaugaag gucuugccuc c                                             21

<210> SEQ ID NO 1040
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1040
ccacaaugaa ggucuugcct c                                             21

<210> SEQ ID NO 1041
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1041
cccacaauga aggucuugcc t                                             21

<210> SEQ ID NO 1042
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1042
ucccacaaug aaggucuugc c                                             21

<210> SEQ ID NO 1043
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1043
cucccacaau gaaggucuug c                                              21

<210> SEQ ID NO 1044
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1044
ucucccacaa ugaaggucut g                                              21

<210> SEQ ID NO 1045
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1045
gucucccaca augaagguct t                                              21

<210> SEQ ID NO 1046
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1046
ggucucccac aaugaagguc t                                              21

<210> SEQ ID NO 1047
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1047
uggucuccca caaugaaggt c                                              21

<210> SEQ ID NO 1048
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1048
cuggucuccc acaaugaagg t                                              21

<210> SEQ ID NO 1049
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1049
ucuggucucc cacaaugaag g                                              21

<210> SEQ ID NO 1050
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1050
aucuggucuc ccacaaugaa g                                              21

<210> SEQ ID NO 1051
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1051
gaucuggucu cccacaauga a                                              21

<210> SEQ ID NO 1052
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1052
agaucugguc ucccacaaug a                                              21

<210> SEQ ID NO 1053
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1053
gagaucuggu cucccacaat g                                              21

<210> SEQ ID NO 1054
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1054
ggagaucugg ucucccacaa t                                              21

<210> SEQ ID NO 1055
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1055
aggagaucug gucucccaca a                                              21

<210> SEQ ID NO 1056
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1056
aaggagaucu ggucucccac a                                              21

<210> SEQ ID NO 1057
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1057
gaaggagauc uggucuccca c                                              21
```

```
<210> SEQ ID NO 1058
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1058
cgaaggagau cuggucuccc a                                              21

<210> SEQ ID NO 1059
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1059
gcgaaggaga ucuggucucc c                                              21

<210> SEQ ID NO 1060
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1060
agcgaaggag aucuggucuc c                                              21

<210> SEQ ID NO 1061
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1061
cagcgaagga gaucuggguct c                                             21

<210> SEQ ID NO 1062
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1062
ucagcgaagg agaucugguc t                                              21
```

<210> SEQ ID NO 1063
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1063
gucagcgaag gagaucuggt c                                              21

<210> SEQ ID NO 1064
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1064
agucagcgaa ggagaucugg t                                              21

<210> SEQ ID NO 1065
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1065
uagucagcga aggagaucug g                                              21

<210> SEQ ID NO 1066
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1066
guagucagcg aaggagauct g                                              21

<210> SEQ ID NO 1067
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1067
uguagucagc gaaggagauc t                                              21

<210> SEQ ID NO 1068
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1068
uuguagucag cgaaggagat c                                              21

<210> SEQ ID NO 1069
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1069
guuguaguca gcgaaggaga t                                              21

<210> SEQ ID NO 1070
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1070
gguuguaguc agcgaaggag a                                              21

<210> SEQ ID NO 1071
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1071
agguuguagu cagcgaagga g                                              21

<210> SEQ ID NO 1072
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1072
cagguuguag ucagcgaagg a                                             21

<210> SEQ ID NO 1073
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1073
gcagguugua gucagcgaag g                                             21

<210> SEQ ID NO 1074
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1074
agcagguugu agucagcgaa g                                             21

<210> SEQ ID NO 1075
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1075
cagcagguug uagucagcga a                                             21

<210> SEQ ID NO 1076
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1076
ccagcagguu guagucagcg a                                             21

<210> SEQ ID NO 1077
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1077
uccagcaggu uguagucagc g                                            21

<210> SEQ ID NO 1078
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1078
guccagcagg uuguagucag c                                            21

<210> SEQ ID NO 1079
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1079
aguccagcag guuguaguca g                                            21

<210> SEQ ID NO 1080
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1080
aaguccagca gguuguaguc a                                            21

<210> SEQ ID NO 1081
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1081
caaguccagc agguuguagt c                                            21

<210> SEQ ID NO 1082
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1082
gcaaguccag cagguuguag t                                              21

<210> SEQ ID NO 1083
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1083
agcaagucca gcagguugua g                                              21

<210> SEQ ID NO 1084
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1084
cagcaagucc agcagguugt a                                              21

<210> SEQ ID NO 1085
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1085
gcagcaaguc cagcagguug t                                              21

<210> SEQ ID NO 1086
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1086
agcagcaagu ccagcaggut g                                              21

<210> SEQ ID NO 1087
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide -continued

<400> SEQUENCE: 1087
cagcagcaag uccagcaggt t                                                    21

<210> SEQ ID NO 1088
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1088
ucagcagcaa guccagcagg t                                                    21

<210> SEQ ID NO 1089
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1089
aucagcagca aguccagcag g                                                    21

<210> SEQ ID NO 1090
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1090
gaucagcagc aaguccagca g                                                    21

<210> SEQ ID NO 1091
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1091
ggaucagcag caaguccagc a                                                    21

<210> SEQ ID NO 1092
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

-continued

Synthetic oligonucleotide

<400> SEQUENCE: 1092
uggaucagca gcaaguccag c                                              21

<210> SEQ ID NO 1093
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1093
auggaucagc agcaagucca g                                              21

<210> SEQ ID NO 1094
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1094
cauggaucag cagcaagucc a                                              21

<210> SEQ ID NO 1095
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1095
ucauggauca gcagcaaguc c                                              21

<210> SEQ ID NO 1096
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1096
cucauggauc agcagcaagt c                                              21

<210> SEQ ID NO 1097
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: Description of Combined DNA/RNA Molecule:
      Synthetic oligonucleotide

<400> SEQUENCE: 1097
ccucauggau cagcagcaag t                                              21

<210> SEQ ID NO 1098
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1098
accucaugga ucagcagcaa g                                              21

<210> SEQ ID NO 1099
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1099
gaccucaugg aucagcagca a                                              21

<210> SEQ ID NO 1100
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1100
ggaccucaug gaucagcagc a                                              21

<210> SEQ ID NO 1101
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1101
aggaccucau ggaucagcag c                                              21

<210> SEQ ID NO 1102
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide <220> FEATURE:
<223> OTHER INFORMATION: Description of Combined DNA/RNA Molecule:
      Synthetic oligonucleotide

<400> SEQUENCE: 1102
uaggaccuca uggaucagca g                                              21

<210> SEQ ID NO 1103
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1103
cuaggaccuc auggaucagc a                                              21

<210> SEQ ID NO 1104
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1104
gcuaggaccu cauggaucag c                                              21

<210> SEQ ID NO 1105
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1105
ggcuaggacc ucauggauca g                                              21

<210> SEQ ID NO 1106
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1106
gggcuaggac cucauggauc a                                              21

<210> SEQ ID NO 1107
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:
      Synthetic oligonucleotide

<400> SEQUENCE: 1107
cgcauccagg cagccagggg c                                           21

<210> SEQ ID NO 1108
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1108
acgcauccag gcagccaggg g                                           21

<210> SEQ ID NO 1109
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1109
aacgcaucca ggcagccagg g                                           21

<210> SEQ ID NO 1110
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1110
gaacgcaucc aggcagccag g                                           21

<210> SEQ ID NO 1111
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1111
ggaacgcauc caggcagcca g                                           21

<210> SEQ ID NO 1112
<211> LENGTH: 21
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1112
gggaacgcau ccaggcagcc a                                             21

<210> SEQ ID NO 1113
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1113
acauaugcug agagcagggg g                                             21

<210> SEQ ID NO 1114
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1114
cacauaugcu gagagcaggg g                                             21

<210> SEQ ID NO 1115
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1115
ccacauaugc ugagagcagg g                                             21

<210> SEQ ID NO 1116
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1116
cccacauaug cugagagcag g                                             21

<210> SEQ ID NO 1117
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1117
gccgggcacu gaggcgcccc a                                            21

<210> SEQ ID NO 1118
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1118
ggccgggcac ugaggcgccc c                                            21

<210> SEQ ID NO 1119
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1119
gggccgggca cugaggcgcc c                                            21

<210> SEQ ID NO 1120
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1120
ugggccgggc acugaggcgc c                                            21

<210> SEQ ID NO 1121
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1121
uugggccggg cacugaggcg c                                            21

<210> SEQ ID NO 1122
<211> LENGTH: 21
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1122
cuugggccgg gcacugaggc g                                              21

<210> SEQ ID NO 1123
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1123
gcuugggccg ggcacugagg c                                              21

<210> SEQ ID NO 1124
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1124
agcuugggcc gggcacugag g                                              21

<210> SEQ ID NO 1125
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1125
gagcuugggc cgggcacuga g                                              21

<210> SEQ ID NO 1126
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1126
ugagcuuggg ccgggcacug a                                              21

<210> SEQ ID NO 1127
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1127
uugagcuugg gccgggcact g                                              21

<210> SEQ ID NO 1128
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1128
cuugagcuug gccgggcac t                                               21

<210> SEQ ID NO 1129
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1129
ccuugagcuu gggccgggca c                                              21

<210> SEQ ID NO 1130
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1130
gccuugagcu ugggccgggc a                                              21

<210> SEQ ID NO 1131
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1131
ggccuugagc uugggccggg c                                              21

<210> SEQ ID NO 1132
```

-continued

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1132
aggccuugag cuugggccgg g                                         21

<210> SEQ ID NO 1133
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1133
aaggccuuga gcuugggccg g                                         21

<210> SEQ ID NO 1134
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1134
gaaggccuug agcuugggcc g                                         21

<210> SEQ ID NO 1135
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1135
ggaaggccuu gagcuugggc c                                         21

<210> SEQ ID NO 1136
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1136
aggaaggccu ugagcuuggg c                                         21
```

<210> SEQ ID NO 1137
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1137
caggaaggcc uugagcuugg g                                            21

<210> SEQ ID NO 1138
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1138
ccaggaaggc cuugagcuug g                                            21

<210> SEQ ID NO 1139
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1139
gccaggaagg ccuugagcut g                                            21

<210> SEQ ID NO 1140
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1140
ggccaggaag gccuugagct t                                            21

<210> SEQ ID NO 1141
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1141
aggccaggaa ggccuugagc t                                            21

<210> SEQ ID NO 1142
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1142
gaggccagga aggccuugag c    21

<210> SEQ ID NO 1143
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1143
ggaggccagg aaggccuuga g    21

<210> SEQ ID NO 1144
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1144
gggaggccag gaaggccuug a    21

<210> SEQ ID NO 1145
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1145
gagguucacg uacucagggg a    21

<210> SEQ ID NO 1146
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1146
ggagguucac guacucaggg g    21

<210> SEQ ID NO 1147
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1147
gggagguuca cguacucagg g                                            21

<210> SEQ ID NO 1148
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1148
ucccguugcc auugaugggg a                                            21

<210> SEQ ID NO 1149
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1149
uucccguugc cauugauggg g                                            21

<210> SEQ ID NO 1150
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1150
uuucccguug ccauugaugg g                                            21

<210> SEQ ID NO 1151
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1151
guuucccguu gccauugaug g                                              21

<210> SEQ ID NO 1152
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1152
uguuucccgu ugccauugat g                                              21

<210> SEQ ID NO 1153
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1153 cuguucccg uugccauuga t                                               21

<210> SEQ ID NO 1154
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1154 acuguuccc guugccauug a                                               21

<210> SEQ ID NO 1155
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1155
cacuguuucc cguugccaut g                                              21

<210> SEQ ID NO 1156
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1156
ucacuguuuc ccguugccat t                                              21

<210> SEQ ID NO 1157
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1157
cucacuguuu cccguugcca t                                              21

<210> SEQ ID NO 1158
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1158
ccucacuguu ucccguugcc a                                              21

<210> SEQ ID NO 1159
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1159
cccucacugu uucccguugc c                                              21

<210> SEQ ID NO 1160
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1160
acccucacug uuucccguug c                                              21

<210> SEQ ID NO 1161
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide -continued

<400> SEQUENCE: 1161
aacccucacu guuucccgut g					21

<210> SEQ ID NO 1162
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1162
caacccucac uguuucccgt t					21

<210> SEQ ID NO 1163
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1163
ccaacccuca cuguuucccg t					21

<210> SEQ ID NO 1164
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1164
cccaacccuc acuguuuccc g					21

<210> SEQ ID NO 1165
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1165
gccucccgcu cagaguccccc c				21

<210> SEQ ID NO 1166
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1166
ugccucccgc ucagaguccc c                                              21

<210> SEQ ID NO 1167
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1167
ucugccuccc gcucagaguc c                                              21

<210> SEQ ID NO 1168
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1168
acucugccuc ccgcucagag t                                              21

<210> SEQ ID NO 1169
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1169
aacucugccu cccgcucaga g                                              21

<210> SEQ ID NO 1170
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1170
aaacucugcc ucccgcucag a                                              21

<210> SEQ ID NO 1171
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 1171
caaacucugc cucccgcuca g        21

<210> SEQ ID NO 1172
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1172
gcaaacucug ccucccgcuc a        21

<210> SEQ ID NO 1173
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1173
ggcaaacucu gccucccgct c        21

<210> SEQ ID NO 1174
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1174
aggcaaacuc ugccucccgc t        21

<210> SEQ ID NO 1175
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1175
aaggcaaacu cugccucccg c        21

<210> SEQ ID NO 1176
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

-continued

```
<223> OTHER INFORMATION: Description of Combined DNA/RNA Molecule:
      Synthetic oligonucleotide

<400> SEQUENCE: 1176
gaaggcaaac ucugccuccc g                                              21

<210> SEQ ID NO 1177
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1177
ggaaggcaaa cucugccucc c                                              21

<210> SEQ ID NO 1178
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1178
aggaaggcaa acucugccuc c                                              21

<210> SEQ ID NO 1179
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1179
aaggaaggca aacucugcct c                                              21

<210> SEQ ID NO 1180
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1180
aaaggaaggc aaacucugcc t                                              21

<210> SEQ ID NO 1181
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 1181
gaaaggaagg caaacucugc c                                              21

<210> SEQ ID NO 1182
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1182
agaaaggaag gcaaacucug c                                              21

<210> SEQ ID NO 1183
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1183
gagaaaggaa ggcaaacuct g                                              21

<210> SEQ ID NO 1184
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1184
ggagaaagga aggcaaacuc t                                              21

<210> SEQ ID NO 1185
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1185
uggagaaagg aaggcaaact c                                              21

<210> SEQ ID NO 1186
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
      oligonucleotide
<220> FEATURE:
<223> OTHER INFORMATION: Description of Combined DNA/RNA Molecule:
      Synthetic oligonucleotide

<400> SEQUENCE: 1186
cuggagaaag gaaggcaaac t                                              21

<210> SEQ ID NO 1187
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1187
ccuggagaaa ggaaggcaaa c                                              21

<210> SEQ ID NO 1188
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1188
uccuggagaa aggaaggcaa a                                              21

<210> SEQ ID NO 1189
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1189
guccuggaga aaggaaggca a                                              21

<210> SEQ ID NO 1190
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1190
gguccuggag aaaggaaggc a                                              21

<210> SEQ ID NO 1191
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1191
ugguccugga gaaaggaagg c                                              21

<210> SEQ ID NO 1192
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1192
uugguccugg agaaaggaag g                                              21

<210> SEQ ID NO 1193
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1193
auugguccug gagaaaggaa g                                              21

<210> SEQ ID NO 1194
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1194
uauugguccu ggagaaagga a                                              21

<210> SEQ ID NO 1195
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1195
uuauuggucc uggagaaagg a                                              21

<210> SEQ ID NO 1196
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1196
uuuauugguc cuggagaaag g                                          21

<210> SEQ ID NO 1197
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1197
uuuuauuggu ccuggagaaa g                                          21

<210> SEQ ID NO 1198
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1198
auuuuauugg uccuggagaa a                                          21

<210> SEQ ID NO 1199
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1199
aauuuuauug guccuggaga a                                          21

<210> SEQ ID NO 1200
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1200
aaauuuuauu gguccuggag a                                          21

<210> SEQ ID NO 1201
<211> LENGTH: 21
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1201
gaaauuuuau ugguccugga g                                           21

<210> SEQ ID NO 1202
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1202
agaaauuuua uugguccugg a                                           21

<210> SEQ ID NO 1203
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1203
uagaaauuuu auugguccug g                                           21

<210> SEQ ID NO 1204
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1204
uuagaaauuu uauuggucct g                                           21

<210> SEQ ID NO 1205
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1205
cuuagaaauu uuauuggucc t                                           21

<210> SEQ ID NO 1206
<211> LENGTH: 21

```
<210> SEQ ID NO 1206
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1206
ucuuagaaau uuuauugguc c                                              21

<210> SEQ ID NO 1207
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1207
cucuuagaaa uuuuauuggt c                                              21

<210> SEQ ID NO 1208
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1208
ucucuuagaa auuuuauugg t                                              21

<210> SEQ ID NO 1209
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1209
cucucuuaga aauuuuauug g                                              21

<210> SEQ ID NO 1210
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1210
gcucucuuag aaauuuuaut g                                              21

<210> SEQ ID NO 1211
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1211
agcucucuua gaaauuuuat t                                              21

<210> SEQ ID NO 1212
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1212
uagcucucuu agaaauuuua t                                              21

<210> SEQ ID NO 1213
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1213
uuagcucucu agaaaauuut a                                              21

<210> SEQ ID NO 1214
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1214
uuuagcucuc uuagaaauut t                                              21

<210> SEQ ID NO 1215
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1215
uuuuagcucu cuuagaaaut t                                              21
```

```
<210> SEQ ID NO 1216
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1216
ucccagaacc agggaggcat t                                              21

<210> SEQ ID NO 1217
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1217
cuuuugagac ccugcuguct t                                              21

<210> SEQ ID NO 1218
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1218
cugucccaga accagggagt t                                              21

<210> SEQ ID NO 1219
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1219
ugucccagaa ccagggaggt t                                              21

<210> SEQ ID NO 1220
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1220
aagccuuuug agacccugct t                                              21
```

<210> SEQ ID NO 1221
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1221
uugagacccu gcugucccat t                                          21

<210> SEQ ID NO 1222
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1222
uuuugagacc cugcugucct t                                          21

<210> SEQ ID NO 1223
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1223
gagacccugc ugucccagat t                                          21

<210> SEQ ID NO 1224
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1224
gcuggaagga ggagguggut t                                          21

<210> SEQ ID NO 1225
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1225
cuggaaggag gagguggugt t                                          21

<210> SEQ ID NO 1226
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1226
ucagggccag agcuggaagt t                                             21

<210> SEQ ID NO 1227
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1227
ugagacccug cugucccagt t                                             21

<210> SEQ ID NO 1228
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1228
agggccagag cuggaaggat t                                             21

<210> SEQ ID NO 1229
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1229
agcuggaagg aggagguggt t                                             21

<210> SEQ ID NO 1230
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1230
agacccugcu gucccagaat t                                        21

<210> SEQ ID NO 1231
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1231
gagcuggaag gaggaggugt t                                        21

<210> SEQ ID NO 1232
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1232
ugcuguccca gaaccagggt t                                        21

<210> SEQ ID NO 1233
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1233
cccagaacca gggaggcaat t                                        21

<210> SEQ ID NO 1234
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1234
ccagaaccag ggaggcaagt t                                        21

<210> SEQ ID NO 1235
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1235
uuugagaccc ugcugcccct t        21

<210> SEQ ID NO 1236
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1236
gacccugcug ucccagaact t        21

<210> SEQ ID NO 1237
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1237
gaucagggcc agagcuggat t        21

<210> SEQ ID NO 1238
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1238
agccuuuuga gacccugcut t        21

<210> SEQ ID NO 1239
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1239
gccuuuugag acccugcugt t        21

<210> SEQ ID NO 1240
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1240
ccuuuugaga cccugcugut t                                              21

<210> SEQ ID NO 1241
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1241
cgccuuuuga gacccugcat t                                              21

<210> SEQ ID NO 1242
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1242
ccuacaccgu ggucuauuut t                                              21

<210> SEQ ID NO 1243
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1243
ugugggagac cagaucucct t                                              21

<210> SEQ ID NO 1244
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1244
gcgggaggca gaguuugcct t                                              21

<210> SEQ ID NO 1245
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 1245
ccuuucucca ggaccaauat t                                              21

<210> SEQ ID NO 1246
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1246
acccugcugu cccagaacct t                                              21

<210> SEQ ID NO 1247
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1247
ggucuauuuc ccaguucgat t                                              21

<210> SEQ ID NO 1248
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1248
cccuggugga cauggugaat t                                              21

<210> SEQ ID NO 1249
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1249
acaucucccu caucuacact t                                              21

<210> SEQ ID NO 1250
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide

<400> SEQUENCE: 1250
gcaaggauga cuaugugaat t          21

<210> SEQ ID NO 1251
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1251
ccuucgcuga cuacaaccut t          21

<210> SEQ ID NO 1252
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1252
cuggcagauc agggccagat t          21

<210> SEQ ID NO 1253
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1253
gacggagacc ucacccugut t          21

<210> SEQ ID NO 1254
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1254
cgggcaagga ugacuaugut t          21

<210> SEQ ID NO 1255
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: Description of Combined DNA/RNA Molecule:
      Synthetic oligonucleotide

<400> SEQUENCE: 1255
cuuuugagac ccugcuguat t                                              21

<210> SEQ ID NO 1256
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1256
gagcuggaag gaggagguat t                                              21

<210> SEQ ID NO 1257
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1257
acccugcugu cccagaacat t                                              21

<210> SEQ ID NO 1258
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1258
ugcuguccca gaaccaggat t                                              21

<210> SEQ ID NO 1259
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1259
agccuuuuga gacccugcat t                                              21

<210> SEQ ID NO 1260
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 1260
ccuuuugaga cccugcugat t                                              21

<210> SEQ ID NO 1261
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1261
ugaagccuuu ugagacccut t                                              21

<210> SEQ ID NO 1262
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1262
acugaagccu uuugagacct t                                              21

<210> SEQ ID NO 1263
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1263
aggaugacua ugugaaggct t                                              21

<210> SEQ ID NO 1264
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1264
ggaugacuau gugaaggcat t                                              21

<210> SEQ ID NO 1265
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
           oligonucleotide
<220> FEATURE:
<223> OTHER INFORMATION: Description of Combined DNA/RNA Molecule:
      Synthetic oligonucleotide

<400> SEQUENCE: 1265
gaugacuaug ugaaggcact t                                              21

<210> SEQ ID NO 1266
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1266
cucccucauc uacaccaact t                                              21

<210> SEQ ID NO 1267
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1267
gaagccuuuu gagacccugt t                                              21

<210> SEQ ID NO 1268
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1268
ucucccucau cuacaccaat t                                              21

<210> SEQ ID NO 1269
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1269
ccucaucuac accaacuaut t                                              21

<210> SEQ ID NO 1270
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1270
cccucaucua caccaacuat t                                              21

<210> SEQ ID NO 1271
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1271
caacugaagc cuuugagat t                                               21

<210> SEQ ID NO 1272
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1272
aacugaagcc uuugagact t                                               21

<210> SEQ ID NO 1273
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1273
cugaagccuu uugagaccct t                                              21

<210> SEQ ID NO 1274
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1274
ucccucaucu acaccaacut t                                              21

<210> SEQ ID NO 1275
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1275
gcucccucau cuacaccaat t                                              21

<210> SEQ ID NO 1276
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1276
gaagccuuuu gagacccuat t                                              21

<210> SEQ ID NO 1277
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1277
acugaagccu uuugagacat t                                              21

<210> SEQ ID NO 1278
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1278
cucccucauc uacaccaaat t                                              21

<210> SEQ ID NO 1279
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1279
ccucaucuac accaacuaat t                                              21

<210> SEQ ID NO 1280
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1280
accaauaaaa uuucuaagat t                                              21

<210> SEQ ID NO 1281
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1281
ugccucccug guucugggac a                                              21

<210> SEQ ID NO 1282
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1282
gacagcaggg ucucaaaagg c                                              21

<210> SEQ ID NO 1283
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1283
cucccugguu cugggacagc a                                              21

<210> SEQ ID NO 1284
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1284
ccucccuggu ucugggacag c                                              21

<210> SEQ ID NO 1285
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1285
gcagggucuc aaaaggcuuc a                                              21

<210> SEQ ID NO 1286
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1286
ugggacagca gggucucaaa a                                              21

<210> SEQ ID NO 1287
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1287
ggacagcagg gucucaaaag g                                              21

<210> SEQ ID NO 1288
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1288
ucugggacag cagggucuca a                                              21

<210> SEQ ID NO 1289
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1289
accaccuccu ccuuccagct c                                              21

<210> SEQ ID NO 1290
```

-continued

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1290
caccaccucc uccuuccagc t                                              21

<210> SEQ ID NO 1291
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1291
cuuccagcuc uggcccugat c                                              21

<210> SEQ ID NO 1292
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1292
cugggacagc agggucucaa a                                              21

<210> SEQ ID NO 1293
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1293
uccuuccagc ucuggcccug a                                              21

<210> SEQ ID NO 1294
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1294
ccaccuccuc cuuccagcuc t                                              21
```

```
<210> SEQ ID NO 1295
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1295
uucugggaca gcaggucuc a                                              21

<210> SEQ ID NO 1296
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1296
caccuccucc uuccagcuct g                                             21

<210> SEQ ID NO 1297
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1297
cccugguucu gggacagcag g                                             21

<210> SEQ ID NO 1298
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1298
uugccucccu gguucuggga c                                             21

<210> SEQ ID NO 1299
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1299
cuugccuccc ugguucuggg a                                             21
```

```
<210> SEQ ID NO 1300
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1300
gggacagcag ggucucaaaa g                                              21

<210> SEQ ID NO 1301
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1301 guucuggac agcaggguct c                                               21

<210> SEQ ID NO 1302
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1302
uccagcucug gcccugauct g                                              21

<210> SEQ ID NO 1303
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1303
agcagggucu caaaaggcut c                                              21

<210> SEQ ID NO 1304
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1304
cagcaggguc ucaaaaggct t                                              21
```

<210> SEQ ID NO 1305
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1305
acagcagggu cucaaaaggc t                                            21

<210> SEQ ID NO 1306
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1306
ugcagggucu caaaaggcgt c                                            21

<210> SEQ ID NO 1307
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1307
aaauagacca cguguaggg c                                             21

<210> SEQ ID NO 1308
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1308
ggagaucugg ucucccacaa t                                            21

<210> SEQ ID NO 1309
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1309
ggcaaacucu gccucccgct c                                              21

<210> SEQ ID NO 1310
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1310
uauugguccu ggagaaagga a                                              21

<210> SEQ ID NO 1311
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1311
gguucuggga cagcaggguc t                                              21

<210> SEQ ID NO 1312
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1312
ucgaacuggg aaauagacca c                                              21

<210> SEQ ID NO 1313
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1313
uucaccaugu ccaccagggc t                                              21

<210> SEQ ID NO 1314
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1314
guguagauga gggagaugua t    21

<210> SEQ ID NO 1315
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1315
uucacauagu cauccuugcc c    21

<210> SEQ ID NO 1316
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1316
agguuguagu cagcgaagga g    21

<210> SEQ ID NO 1317
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1317
ucuggcccug aucugccagc a    21

<210> SEQ ID NO 1318
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1318
acagggugag gucuccgucc t    21

<210> SEQ ID NO 1319
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide -continued

<400> SEQUENCE: 1319
acauagucau ccuugcccgc c         21

<210> SEQ ID NO 1320
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1320
uacagcaggg ucucaaaagg c         21

<210> SEQ ID NO 1321
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1321
uaccuccucc uuccagcuct g         21

<210> SEQ ID NO 1322
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1322
uguucuggga cagcaggguc t         21

<210> SEQ ID NO 1323
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1323
uccugguucu gggacagcag g         21

<210> SEQ ID NO 1324
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1324
ugcagggucu caaaaggcut c                                         21

<210> SEQ ID NO 1325
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1325
ucagcagggu cucaaaaggc t                                         21

<210> SEQ ID NO 1326
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1326
agggucucaa aaggcuucag t                                         21

<210> SEQ ID NO 1327
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1327
ggucucaaaa ggcuucagut g                                         21

<210> SEQ ID NO 1328
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1328
gccuucacau agucauccut g                                         21

<210> SEQ ID NO 1329
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 1329
ugccuucaca uagucaucct t                                              21

<210> SEQ ID NO 1330
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1330
gugccuucac auagucaucc t                                              21

<210> SEQ ID NO 1331
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1331
guugguguag augagggaga t                                              21

<210> SEQ ID NO 1332
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1332
cagggucuca aaaggcuuca g                                              21

<210> SEQ ID NO 1333
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1333
uugguguaga ugagggagat g                                              21

<210> SEQ ID NO 1334
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 1334
auaguuggug uagaugaggg a                                              21

<210> SEQ ID NO 1335
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1335
uaguuggugu agaugaggga g                                              21

<210> SEQ ID NO 1336
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1336
ucucaaaagg cuucaguugc c                                              21

<210> SEQ ID NO 1337
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1337
gucucaaaag gcuucaguug c                                              21

<210> SEQ ID NO 1338
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1338
gggucucaaa aggcuucagt t                                              21

<210> SEQ ID NO 1339
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 1339
aguuggugua gaugagggag a                                          21

<210> SEQ ID NO 1340
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1340
uugguguaga ugagggagct g                                          21

<210> SEQ ID NO 1341
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1341
uagggucuca aaaggcuuca g                                          21

<210> SEQ ID NO 1342
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1342
ugucucaaaa ggcuucagut g                                          21

<210> SEQ ID NO 1343
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1343
uuugguguag augagggaga t                                          21

<210> SEQ ID NO 1344
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1344
uuaguuggug uagaugaggg a                                              21

<210> SEQ ID NO 1345
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1345
ucuuagaaau uuuauugguc c                                              21
```

RNA AGENTS FOR GST-PI GENE MODULATION

SEQUENCE LISTING

This application includes a Sequence Listing submitted electronically as an ASCII file created on Dec. 23, 2015, named ND5123202US_SL.txt, which is 443,134 bytes in size, and is hereby incorporated by reference in its entirety.

BACKGROUND OF THE INVENTION

Various human cancer tissues have been found to correlate with the appearance of mutated KRAS gene. In some cases, the tissues also present an elevated level of Glutathione S-Tranferase Pi (GST-π) expression. (Miyanishi et al., Gastroenterology, 2001, Vol. 121:865-874, Abstract) For example, elevated serum GST-π levels were observed in patients with various gastrointestinal malignancies. (Niitsu et al., Cancer, 1989, Vol. 63, No. 2, pp. 317-323, Abstract)

GST-π is a member of a GST family of enzymes that play a role in detoxification by catalyzing the conjugation of hydrophobic and electrophilic compounds with reduced glutathione. GST-π expression can be reduced in vitro with a siRNA. (Niitsu et al., US 2014/0315975 A1)

Therapeutics for inhibition of GST-π expression will require highly potent siRNA sequences and structures.

What is needed are siRNA sequences, compounds and structures for inhibition of GST-π expression.

BRIEF SUMMARY

This invention relates to the fields of biopharmaceuticals and therapeutics composed of nucleic acid based molecules. More particularly, this invention relates to compounds and compositions utilizing RNA interference (RNAi) for modulating the expression of human GST-π.

This invention relates to compounds, compositions and methods for modulating the expression of human GST-π using RNA interference.

In some embodiments, this invention provides molecules for RNA interference gene silencing of GST-π.

In further embodiments, the structures, molecules and compositions of this invention can be used in methods for preventing or treating diseases, or ameliorating symptoms of conditions or disorders associated with GST-π, including malignant tumor.

Embodiments of this invention include the following:

A nucleic acid molecule, wherein:

a) the molecule has a polynucleotide sense strand and a polynucleotide antisense strand;

b) each strand of the molecule is from 15 to 30 nucleotides in length;

c) a contiguous region of from 15 to 30 nucleotides of the antisense strand is complementary to a sequence of an mRNA encoding GST-π;

d) at least a portion of the sense strand is complementary to at least a portion of the antisense strand, and the molecule has a duplex region of from 15 to 30 nucleotides in length.

In some embodiments, the nucleic acid molecule can have contiguous region of from 15 to 30 nucleotides of the antisense strand that is complementary to a sequence of an mRNA encoding GST-π is located in the duplex region of the molecule.

In additional embodiments, the nucleic acid molecule can have a contiguous region of from 15 to 30 nucleotides of the antisense strand that is complementary to a sequence of an mRNA encoding GST-π.

Compounds of this invention can have a sequence of an mRNA encoding GST-π that is selected from the group consisting of 5'UTR positions 1 to 249 of SEQ ID NO:1, CDS positions 250 to 882 of SEQ ID NO:1, and 3'UTR positions 883 to 986 of SEQ ID NO:1.

In certain embodiments, each strand of the nucleic acid molecule can be from 18 to 22 nucleotides in length. The duplex region of the nucleic acid molecule can be 19 nucleotides in length.

In alternative forms, the nucleic acid molecule can have a polynucleotide sense strand and a polynucleotide antisense strand that are connected as a single strand, and form a duplex region connected at one end by a loop.

Some embodiments of a nucleic acid molecule of this disclosure can have a blunt end. In certain embodiments, a nucleic acid molecule can have one or more 3' overhangs.

This invention provides a range of nucleic acid molecules that are RNAi molecules active for gene silencing. The inventive nucleic acid molecules can be a dsRNA, a siRNA, a micro-RNA, or a shRNA active for gene silencing, as well as a DNA-directed RNA (ddRNA), Piwi-interacting RNA (piRNA), or a repeat associated siRNA (rasiRNA). The nucleic acid molecules can be active for inhibiting expression of GST-π.

Embodiments of this invention further provide nucleic acid molecules having an IC50 for knockdown of GST-π of less than 100 pM.

This invention further contemplates compositions containing one or more of the inventive nucleic acid molecules, along with a pharmaceutically acceptable carrier. In certain embodiments, the carrier can be a lipid molecule or liposome.

The compounds and compositions of this invention are useful in methods for preventing or treating a GST-π associated disease, by administering a compound or composition to a subject in need.

The methods of this invention can utilize the inventive compounds for preventing or treating malignant tumor. The malignant tumor can be presented in various diseases, for example, cancers associated with GST-π expression, cancers caused by cells expressing mutated KRAS, sarcomas, fibrosarcoma, malignant fibrous histiocytoma, liposarcoma, rhabdomyosarcoma, leiomyosarcoma, angiosarcoma, Kaposi's sarcoma, lymphangiosarcoma, synovial sarcoma, chondrosarcoma, osteosarcoma, carcinomas, brain tumor, head and neck cancer, breast cancer, lung cancer, esophageal cancer, stomach cancer, duodenal cancer, appendix cancer, colorectal cancer, rectal cancer, liver cancer, pancreatic cancer, gallbladder cancer, bile duct cancer, anus cancer, kidney cancer, urethral cancer, urinary bladder cancer, prostate cancer, testicular cancer, uterine cancer, ovary cancer, skin cancer, leukemia, malignant lymphoma, epithelial malignant tumors, and non-epithelial malignant tumors.

BRIEF DESCRIPTION OF THE DRAWINGS

FIG. 1 shows SEQ ID NO: 1, which is the nucleic acid sequence of target human glutathione S-transferase pi (human GST-π) mRNA, disclosed in GenBank accession number NM_000852.3 (hGSTP1), which is 986 nucleotides in length.

DETAILED DESCRIPTION OF THE INVENTION

Figure 2:
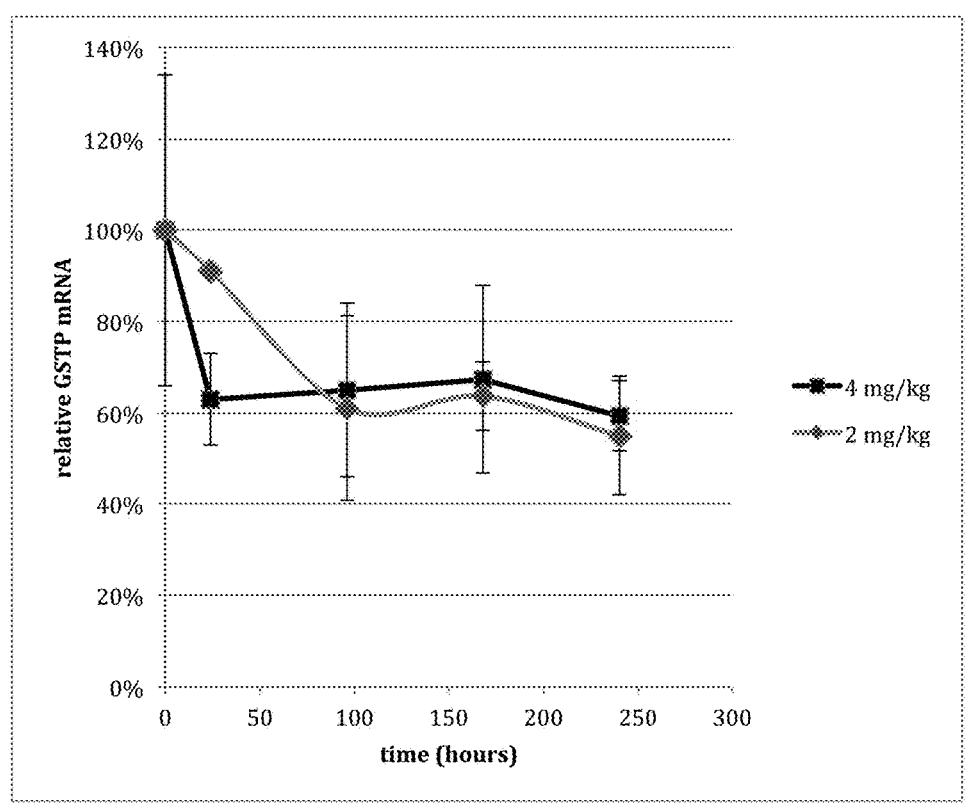
FIG. 2 shows in vivo knockdown efficacy for GST-π siRNA. Dose dependent knockdown of GST-π mRNA was observed in vivo with siRNA targeted to GST-π, as shown in FIG. 2.

This invention relates to compounds, compositions and methods for nucleic acid based therapeutics for modulating expression of GST-π.

In some embodiments, this invention provides molecules active in RNA interference, as well as structures and compositions that can silence expression of GST-π.

The structures and compositions of this disclosure can be used in preventing or treating various diseases such as malignant tumor.

In further embodiments, this invention provides compositions for delivery and uptake of one or more therapeutic RNAi molecules of this invention, as well as methods of use thereof. The RNA-based compositions of this invention can be used in methods for preventing or treating malignant tumors, such as cancers.

Therapeutic compositions of this invention include nucleic acid molecules that are active in RNA interference. The therapeutic nucleic acid molecules can be targeted to GSTP1 (GST-π) for gene silencing.

In various embodiments, this invention provides a range of molecules that can be active as a small interfering RNA (siRNA), and can regulate or silence GST-π gene expression.

The siRNAs of this invention can be used for preventing or treating malignant tumors.

Embodiments of this invention further provide a vehicle, formulation, or lipid nanoparticle formulation for delivery of the inventive siRNAs to subjects in need of preventing or treating a malignant tumor. This invention further contemplates methods for administering siRNAs as therapeutics to mammals.

The therapeutic molecules and compositions of this invention can be used for RNA interference directed to preventing or treating a GST-π associated disease, by administering a compound or composition to a subject in need.

The methods of this invention can utilize the inventive compounds for preventing or treating malignant tumor. The malignant tumor can be presented in various diseases, for example, cancers that highly expressing GST-π, cancers caused by cells expressing mutated KRAS, sarcomas, fibrosarcoma, malignant fibrous histiocytoma, liposarcoma, rhabdomyosarcoma, leiomyosarcoma, angiosarcoma, Kaposi's sarcoma, lymphangiosarcoma, synovial sarcoma, chondrosarcoma, osteosarcoma, carcinomas, brain tumor, head and neck cancer, breast cancer, lung cancer, esophageal cancer, stomach cancer, duodenal cancer, colorectal cancer, liver cancer, pancreatic cancer, gallbladder cancer, bile duct cancer, kidney cancer, urethral cancer, bladder cancer, prostate cancer, testicular cancer, uterine cancer, ovary cancer, skin cancer, leukemia, malignant lymphoma, epithelial malignant tumors, and non-epithelial malignant tumors.

In certain embodiments, a combination of therapeutic molecules of this invention can be used for silencing or inhibiting GST-π gene expression.

This invention provides a range of RNAi molecules, where each molecule has a polynucleotide sense strand and a polynucleotide antisense strand; each strand of the molecule is from 15 to 30 nucleotides in length; a contiguous region of from 15 to 30 nucleotides of the antisense strand is complementary to a sequence of an mRNA encoding GST-π; and at least a portion of the sense strand is complementary to at least a portion of the antisense strand, and the molecule has a duplex region of from 15 to 30 nucleotides in length.

A RNAi molecule of this invention can have a contiguous region of from 15 to 30 nucleotides of the antisense strand that is complementary to a sequence of an mRNA encoding GST-π, which is located in the duplex region of the molecule.

In some embodiments, a RNAi molecule can have a contiguous region of from 15 to 30 nucleotides of the antisense strand that is complementary to a sequence of an mRNA encoding GST-π.

Embodiments of this invention may further provide methods for preventing, treating or ameliorating one or more symptoms of malignant tumor, or reducing the risk of developing malignant tumor, or delaying the onset of malignant tumor in a mammal in need thereof.

GST-π and RNAi Molecules

FIG. 1 shows the nucleic acid sequence of an example target human glutathione S-transferase pi (human GST-π) mRNA, which is disclosed in GenBank accession number NM_000852.3 (hGSTP1), and is 986 nucleotides in length (SEQ ID NO: 1).

One of ordinary skill in the art would understand that a reported sequence may change over time and to incorporate any changes needed in the nucleic acid molecules herein accordingly.

Embodiments of this invention can provide compositions and methods for gene silencing of GST-π expression using small nucleic acid molecules. Examples of nucleic acid molecules include molecules active in RNA interference (RNAi molecules), short interfering RNA (siRNA), double-stranded RNA (dsRNA), micro-RNA (miRNA), and short hairpin RNA (shRNA) molecules, as well as DNA-directed RNAs (ddRNA), Piwi-interacting RNAs (piRNA), and repeat associated siRNAs (rasiRNA). Such molecules are capable of mediating RNA interference against GST-π gene expression.

The composition and methods disclosed herein can also be used in treating various kinds of malignant tumors in a subject.

The nucleic acid molecules and methods of this invention may be used to down regulate the expression of genes that encode GST-π.

The compositions and methods of this invention can include one or more nucleic acid molecules, which, independently or in combination, can modulate or regulate the expression of GST-π protein and/or genes encoding GST-π proteins, proteins and/or genes encoding GST-π associated with the maintenance and/or development of diseases, conditions or disorders associated with GST-π, such as malignant tumor.

The compositions and methods of this invention are described with reference to exemplary sequences of GST-π. A person of ordinary skill in the art would understand that various aspects and embodiments of the invention are directed to any related GST-π genes, sequences, or variants, such as homolog genes and transcript variants, and polymorphisms, including single nucleotide polymorphism (SNP) associated with any GST-π genes.

In some embodiments, the compositions and methods of this invention can provide a double-stranded short interfering nucleic acid (siRNA) molecule that downregulates the expression of a GST-π gene, for example human GST-π.

A RNAi molecule of this invention can be targeted to GST-π and any homologous sequences, for example, using complementary sequences or by incorporating non-canonical base pairs, for example, mismatches and/or wobble base pairs, that can provide additional target sequences.

In instances where mismatches are identified, non-canonical base pairs, for example, mismatches and/or wobble bases can be used to generate nucleic acid molecules that target more than one gene sequence.

For example, non-canonical base pairs such as UU and CC base pairs can be used to generate nucleic acid molecules that are capable of targeting sequences for differing GST-π targets that share sequence homology. Thus, a RNAi molecule can be targeted to a nucleotide sequence that is conserved between homologous genes, and a single RNAi molecule can be used to inhibit expression of more than one gene.

In some aspects, the compositions and methods of this invention include RNAi molecules that are active against GST-π mRNA, where the RNAi molecule includes a sequence complementary to any mRNA encoding a GST-π sequence.

In some embodiments, a RNAi molecule of this disclosure can have activity against GST-π RNA, where the RNAi molecule includes a sequence complementary to an RNA having a variant GST-π encoding sequence, for example, a mutant GST-π gene known in the art to be associated with malignant tumor.

In further embodiments, a RNAi molecule of this invention can include a nucleotide sequence that can interact with a nucleotide sequence of a GST-π gene and mediate silencing of GST-π gene expression.

Examples of RNAi molecules of this invention targeted to GST-π mRNA are shown in Tables 1 and 2.

TABLE 1

RNAi molecule sequences for GST-7c

| Ref Pos | SEQ ID NO | SENSE STRAND (5'-->3') SEQ ID NOS: 2 to 608 | SEQ ID NO | ANTISENSE STRAND (5'-->3') SEQ ID NOS: 609 to 1215 |
|---|---|---|---|---|
| 232 | 2 | GCCGCAGUCUUCGCCACCAtt | 609 | UGGUGGCGAAGACUGCGGCgg |
| 233 | 3 | CCGCAGUCUUCGCCACCAUtt | 610 | AUGGUGGCGAAGACUGCGGcg |
| 234 | 4 | CGCAGUCUUCGCCACCAUGtt | 611 | CAUGGUGGCGAAGACUGCGgc |
| 235 | 5 | GCAGUCUUCGCCACCAUGCtt | 612 | GCAUGGUGGCGAAGACUGCgg |
| 236 | 6 | CAGUCUUCGCCACCAUGCCtt | 613 | GGCAUGGUGGCGAAGACUGcg |
| 237 | 7 | AGUCUUCGCCACCAUGCCGtt | 614 | CGGCAUGGUGGCGAAGACUgc |
| 238 | 8 | GUCUUCGCCACCAUGCCGCtt | 615 | GCGGCAUGGUGGCGAAGACtg |
| 239 | 9 | UCUUCGCCACCAUGCCGCCtt | 616 | GGCGGCAUGGUGGCGAAGAct |
| 240 | 10 | CUUCGCCACCAUGCCGCCCtt | 617 | GGGCGGCAUGGUGGCGAAGac |
| 241 | 11 | UUCGCCACCAUGCCGCCCUtt | 618 | AGGGCGGCAUGGUGGCGAAga |
| 242 | 12 | UCGCCACCAUGCCGCCCUAtt | 619 | UAGGGCGGCAUGGUGGCGAag |
| 243 | 13 | CGCCACCAUGCCGCCCUACtt | 620 | GUAGGGCGGCAUGGUGGCGaa |
| 244 | 14 | GCCACCAUGCCGCCCUACAtt | 621 | UGUAGGGCGGCAUGGUGGCga |
| 245 | 15 | CCACCAUGCCGCCCUACACtt | 622 | GUGUAGGGCGGCAUGGUGGcg |
| 246 | 16 | CACCAUGCCGCCCUACACCtt | 623 | GGUGUAGGGCGGCAUGGUGgc |
| 247 | 17 | ACCAUGCCGCCCUACACCGtt | 624 | CGGUGUAGGGCGGCAUGGUgg |
| 248 | 18 | CCAUGCCGCCCUACACCGUtt | 625 | ACGGUGUAGGGCGGCAUGGtg |
| 249 | 19 | CAUGCCGCCCUACACCGUGtt | 626 | CACGGUGUAGGGCGGCAUGgt |
| 250 | 20 | AUGCCGCCCUACACCGUGGtt | 627 | CCACGGUGUAGGGCGGCAUgg |
| 251 | 21 | UGCCGCCCUACACCGUGGUtt | 628 | ACCACGGUGUAGGGCGGCAtg |
| 252 | 22 | GCCGCCCUACACCGUGGUCtt | 629 | GACCACGGUGUAGGGCGGCat |
| 253 | 23 | CCGCCCUACACCGUGGUCUtt | 630 | AGACCACGGUGUAGGGCGGca |
| 254 | 24 | CGCCCUACACCGUGGUCUAtt | 631 | UAGACCACGGUGUAGGGCGgc |
| 255 | 25 | GCCCUACACCGUGGUCUAUtt | 632 | AUAGACCACGGUGUAGGGCgg |
| 256 | 26 | CCCUACACCGUGGUCUAUUtt | 633 | AAUAGACCACGGUGUAGGGcg |

TABLE 1-continued

RNAi molecule sequences for GST-7c

| Ref Pos | SEQ ID NO | SENSE STRAND (5'-->3') SEQ ID NOS: 2 to 608 | SEQ ID NO | ANTISENSE STRAND (5'-->3') SEQ ID NOS: 609 to 1215 |
|---|---|---|---|---|
| 257 | 27 | CCUACACCGUGGUCUAUUUtt | 634 | AAAUAGACCACGGUGUAGGgc |
| 258 | 28 | CUACACCGUGGUCUAUUUCtt | 635 | GAAAUAGACCACGGUGUAGgg |
| 259 | 29 | UACACCGUGGUCUAUUUCCtt | 636 | GGAAAUAGACCACGGUGUAgg |
| 260 | 30 | ACACCGUGGUCUAUUUCCCtt | 637 | GGGAAAUAGACCACGGUGUag |
| 261 | 31 | CACCGUGGUCUAUUUCCCAtt | 638 | UGGGAAAUAGACCACGGUGta |
| 262 | 32 | ACCGUGGUCUAUUUCCCAGtt | 639 | CUGGGAAAUAGACCACGGUgt |
| 263 | 33 | CCGUGGUCUAUUUCCCAGUtt | 640 | ACUGGGAAAUAGACCACGGtg |
| 264 | 34 | CGUGGUCUAUUUCCCAGUUtt | 641 | AACUGGGAAAUAGACCACGgt |
| 265 | 35 | GUGGUCUAUUUCCCAGUUCtt | 642 | GAACUGGGAAAUAGACCACgg |
| 266 | 36 | UGGUCUAUUUCCCAGUUCGtt | 643 | CGAACUGGGAAAUAGACCAcg |
| 267 | 37 | GGUCUAUUUCCCAGUUCGAtt | 644 | UCGAACUGGGAAAUAGACCac |
| 268 | 38 | GUCUAUUUCCCAGUUCGAGtt | 645 | CUCGAACUGGGAAAUAGACca |
| 269 | 39 | UCUAUUUCCCAGUUCGAGGtt | 646 | CCUCGAACUGGGAAAUAGAcc |
| 270 | 40 | CUAUUUCCCAGUUCGAGGCtt | 647 | GCCUCGAACUGGGAAAUAGac |
| 271 | 41 | UAUUUCCCAGUUCGAGGCCtt | 648 | GGCCUCGAACUGGGAAAUAga |
| 272 | 42 | AUUUCCCAGUUCGAGGCCGtt | 649 | CGGCCUCGAACUGGGAAAUag |
| 273 | 43 | UUUCCCAGUUCGAGGCCGCtt | 650 | GCGGCCUCGAACUGGGAAAta |
| 274 | 44 | UUCCCAGUUCGAGGCCGCUtt | 651 | AGCGGCCUCGAACUGGGAAat |
| 275 | 45 | UCCCAGUUCGAGGCCGCUGtt | 652 | CAGCGGCCUCGAACUGGGAaa |
| 276 | 46 | CCCAGUUCGAGGCCGCUGCtt | 653 | GCAGCGGCCUCGAACUGGGaa |
| 277 | 47 | CCAGUUCGAGGCCGCUGCGtt | 654 | CGCAGCGGCCUCGAACUGGga |
| 278 | 48 | CAGUUCGAGGCCGCUGCGCtt | 655 | GCGCAGCGGCCUCGAACUGgg |
| 279 | 49 | AGUUCGAGGCCGCUGCGCGtt | 656 | CGCGCAGCGGCCUCGAACUgg |
| 280 | 50 | GUUCGAGGCCGCUGCGCGGtt | 657 | CCGCGCAGCGGCCUCGAACtg |
| 281 | 51 | UUCGAGGCCGCUGCGCGGCtt | 658 | GCCGCGCAGCGGCCUCGAAct |
| 282 | 52 | UCGAGGCCGCUGCGCGGCCtt | 659 | GGCCGCGCAGCGGCCUCGAac |
| 283 | 53 | CGAGGCCGCUGCGCGGCCCtt | 660 | GGGCCGCGCAGCGGCCUCGaa |
| 284 | 54 | GAGGCCGCUGCGCGGCCCUtt | 661 | AGGGCCGCGCAGCGGCCUCga |
| 285 | 55 | AGGCCGCUGCGCGGCCCUGtt | 662 | CAGGGCCGCGCAGCGGCCUcg |
| 286 | 56 | GGCCGCUGCGCGGCCCUGCtt | 663 | GCAGGGCCGCGCAGCGGCCtc |
| 287 | 57 | GCCGCUGCGCGGCCCUGCGtt | 664 | CGCAGGGCCGCGCAGCGGCct |
| 288 | 58 | CCGCUGCGCGGCCCUGCGCtt | 665 | GCGCAGGGCCGCGCAGCGGcc |
| 289 | 59 | CGCUGCGCGGCCCUGCGCAtt | 666 | UGCGCAGGGCCGCGCAGCGgc |
| 290 | 60 | GCUGCGCGGCCCUGCGCAUtt | 667 | AUGCGCAGGGCCGCGCAGCgg |
| 291 | 61 | CUGCGCGGCCCUGCGCAUGtt | 668 | CAUGCGCAGGGCCGCGCAGcg |
| 292 | 62 | UGCGCGGCCCUGCGCAUGCtt | 669 | GCAUGCGCAGGGCCGCGCAgc |
| 293 | 63 | GCGCGGCCCUGCGCAUGCUtt | 670 | AGCAUGCGCAGGGCCGCGCag |

TABLE 1-continued

RNAi molecule sequences for GST-7c

| Ref Pos | SEQ ID NO | SENSE STRAND (5'-->3') SEQ ID NOS: 2 to 608 | SEQ ID NO | ANTISENSE STRAND (5'-->3') SEQ ID NOS: 609 to 1215 |
|---|---|---|---|---|
| 294 | 64 | CGCGGCCCUGCGCAUGCUGtt | 671 | CAGCAUGCGCAGGGCCGCca |
| 295 | 65 | GCGGCCCUGCGCAUGCUGCtt | 672 | GCAGCAUGCGCAGGGCCGCgc |
| 296 | 66 | CGGCCCUGCGCAUGCUGCUtt | 673 | AGCAGCAUGCGCAGGGCCGcg |
| 297 | 67 | GGCCCUGCGCAUGCUGCUGtt | 674 | CAGCAGCAUGCGCAGGGCCgc |
| 298 | 68 | GCCCUGCGCAUGCUGCUGGtt | 675 | CCAGCAGCAUGCGCAGGGCcg |
| 299 | 69 | CCCUGCGCAUGCUGCUGGCtt | 676 | GCCAGCAGCAUGCGCAGGGcc |
| 300 | 70 | CCUGCGCAUGCUGCUGGCAtt | 677 | UGCCAGCAGCAUGCGCAGGgc |
| 301 | 71 | CUGCGCAUGCUGCUGGCAGtt | 678 | CUGCCAGCAGCAUGCGCAGgg |
| 302 | 72 | UGCGCAUGCUGCUGGCAGAtt | 679 | UCUGCCAGCAGCAUGCGCAgg |
| 303 | 73 | GCGCAUGCUGCUGGCAGAUtt | 680 | AUCUGCCAGCAGCAUGCGCag |
| 304 | 74 | CGCAUGCUGCUGGCAGAUCtt | 681 | GAUCUGCCAGCAGCAUGCGca |
| 305 | 75 | GCAUGCUGCUGGCAGAUCAtt | 682 | UGAUCUGCCAGCAGCAUGCgc |
| 306 | 76 | CAUGCUGCUGGCAGAUCAGtt | 683 | CUGAUCUGCCAGCAGCAUGcg |
| 307 | 77 | AUGCUGCUGGCAGAUCAGGtt | 684 | CCUGAUCUGCCAGCAGCAUgc |
| 308 | 78 | UGCUGCUGGCAGAUCAGGGtt | 685 | CCCUGAUCUGCCAGCAGCAtg |
| 309 | 79 | GCUGCUGGCAGAUCAGGGCtt | 686 | GCCCUGAUCUGCCAGCAGCat |
| 310 | 80 | CUGCUGGCAGAUCAGGGCCtt | 687 | GGCCCUGAUCUGCCAGCAGca |
| 311 | 81 | UGCUGGCAGAUCAGGGCCAtt | 688 | UGGCCCUGAUCUGCCAGCAgc |
| 312 | 82 | GCUGGCAGAUCAGGGCCAGtt | 689 | CUGGCCCUGAUCUGCCAGCag |
| 313 | 83 | CUGGCAGAUCAGGGCCAGAtt | 690 | UCUGGCCCUGAUCUGCCAGca |
| 314 | 84 | UGGCAGAUCAGGGCCAGAGtt | 691 | CUCUGGCCCUGAUCUGCCAGc |
| 315 | 85 | GGCAGAUCAGGGCCAGAGCtt | 692 | GCUCUGGCCCUGAUCUGCCag |
| 316 | 86 | GCAGAUCAGGGCCAGAGCUtt | 693 | AGCUCUGGCCCUGAUCUGCca |
| 317 | 87 | CAGAUCAGGGCCAGAGCUGtt | 694 | CAGCUCUGGCCCUGAUCUGcc |
| 318 | 88 | AGAUCAGGGCCAGAGCUGGtt | 695 | CCAGCUCUGGCCCUGAUCUgc |
| 319 | 89 | GAUCAGGGCCAGAGCUGGAtt | 696 | UCCAGCUCUGGCCCUGAUCtg |
| 320 | 90 | AUCAGGGCCAGAGCUGGAAtt | 697 | UUCCAGCUCUGGCCCUGAUct |
| 321 | 91 | UCAGGGCCAGAGCUGGAAGtt | 698 | CUUCCAGCUCUGGCCCUGAtc |
| 322 | 92 | CAGGGCCAGAGCUGGAAGGtt | 699 | CCUUCCAGCUCUGGCCCUGat |
| 323 | 93 | AGGGCCAGAGCUGGAAGGAtt | 700 | UCCUUCCAGCUCUGGCCCUga |
| 324 | 94 | GGGCCAGAGCUGGAAGGAGtt | 701 | CUCCUUCCAGCUCUGGCCCtg |
| 325 | 95 | GGCCAGAGCUGGAAGGAGGtt | 702 | CCUCCUUCCAGCUCUGGCCct |
| 326 | 96 | GCCAGAGCUGGAAGGAGGAtt | 703 | UCCUCCUUCCAGCUCUGGCcc |
| 327 | 97 | CCAGAGCUGGAAGGAGGAGtt | 704 | CUCCUCCUUCCAGCUCUGGcc |
| 328 | 98 | CAGAGCUGGAAGGAGGAGGtt | 705 | CCUCCUCCUUCCAGCUCUGgc |
| 329 | 99 | AGAGCUGGAAGGAGGAGGUtt | 706 | ACCUCCUCCUUCCAGCUCUgg |
| 330 | 100 | GAGCUGGAAGGAGGAGGUGtt | 707 | CACCUCCUCCUUCCAGCUCtg |

TABLE 1-continued

RNAi molecule sequences for GST-7c

| Ref Pos | SEQ ID NO | SENSE STRAND (5'-->3') SEQ ID NOS: 2 to 608 | SEQ ID NO | ANTISENSE STRAND (5'-->3') SEQ ID NOS: 609 to 1215 |
|---|---|---|---|---|
| 330 | 101 | GAGCUGGAAGGAGGAGGUAtt | 708 | UACCUCCUCCUUCCAGCUCtg |
| 331 | 102 | AGCUGGAAGGAGGAGGUGGtt | 709 | CCACCUCCUCCUUCCAGCUct |
| 332 | 103 | GCUGGAAGGAGGAGGUGGUtt | 710 | ACCACCUCCUCCUUCCAGCtc |
| 333 | 104 | CUGGAAGGAGGAGGUGGUGtt | 711 | CACCACCUCCUCCUUCCAGct |
| 334 | 105 | UGGAAGGAGGAGGUGGUGAtt | 712 | UCACCACCUCCUCCUUCCAgc |
| 335 | 106 | GGAAGGAGGAGGUGGUGACtt | 713 | GUCACCACCUCCUCCUUCCag |
| 336 | 107 | GAAGGAGGAGGUGGUGACCtt | 714 | GGUCACCACCUCCUCCUUCca |
| 337 | 108 | AAGGAGGAGGUGGUGACCGtt | 715 | CGGUCACCACCUCCUCCUUcc |
| 338 | 109 | AGGAGGAGGUGGUGACCGUtt | 716 | ACGGUCACCACCUCCUCCUtc |
| 339 | 110 | GGAGGAGGUGGUGACCGUGtt | 717 | CACGGUCACCACCUCCUCCtt |
| 340 | 111 | GAGGAGGUGGUGACCGUGGtt | 718 | CCACGGUCACCACCUCCUCct |
| 341 | 112 | AGGAGGUGGUGACCGUGGAtt | 719 | UCCACGGUCACCACCUCCUcc |
| 342 | 113 | GGAGGUGGUGACCGUGGAGtt | 720 | CUCCACGGUCACCACCUCCtc |
| 343 | 114 | GAGGUGGUGACCGUGGAGAtt | 721 | UCUCCACGGUCACCACCUCct |
| 344 | 115 | AGGUGGUGACCGUGGAGACtt | 722 | GUCUCCACGGUCACCACCUcc |
| 345 | 116 | GGUGGUGACCGUGGAGACGtt | 723 | CGUCUCCACGGUCACCACCtc |
| 346 | 117 | GUGGUGACCGUGGAGACGUtt | 724 | ACGUCUCCACGGUCACCACct |
| 347 | 118 | UGGUGACCGUGGAGACGUGtt | 725 | CACGUCUCCACGGUCACCAcc |
| 348 | 119 | GGUGACCGUGGAGACGUGGtt | 726 | CCACGUCUCCACGGUCACCac |
| 349 | 120 | GUGACCGUGGAGACGUGGCtt | 727 | GCCACGUCUCCACGGUCACca |
| 350 | 121 | UGACCGUGGAGACGUGGCAtt | 728 | UGCCACGUCUCCACGGUCAcc |
| 351 | 122 | GACCGUGGAGACGUGGCAGtt | 729 | CUGCCACGUCUCCACGGUCac |
| 352 | 123 | ACCGUGGAGACGUGGCAGGtt | 730 | CCUGCCACGUCUCCACGGUca |
| 353 | 124 | CCGUGGAGACGUGGCAGGAtt | 731 | UCCUGCCACGUCUCCACGGtc |
| 354 | 125 | CGUGGAGACGUGGCAGGAGtt | 732 | CUCCUGCCACGUCUCCACGgt |
| 355 | 126 | GUGGAGACGUGGCAGGAGGtt | 733 | CCUCCUGCCACGUCUCCACgg |
| 356 | 127 | UGGAGACGUGGCAGGAGGGtt | 734 | CCCUCCUGCCACGUCUCCAcg |
| 357 | 128 | GGAGACGUGGCAGGAGGGCtt | 735 | GCCCUCCUGCCACGUCUCCac |
| 358 | 129 | GAGACGUGGCAGGAGGGCUtt | 736 | AGCCCUCCUGCCACGUCUCca |
| 359 | 130 | AGACGUGGCAGGAGGGCUCtt | 737 | GAGCCCUCCUGCCACGUCUcc |
| 360 | 131 | GACGUGGCAGGAGGGCUCAtt | 738 | UGAGCCCUCCUGCCACGUCtc |
| 361 | 132 | ACGUGGCAGGAGGGCUCACtt | 739 | GUGAGCCCUCCUGCCACGUct |
| 362 | 133 | CGUGGCAGGAGGGCUCACUtt | 740 | AGUGAGCCCUCCUGCCACGtc |
| 363 | 134 | GUGGCAGGAGGGCUCACUCtt | 741 | GAGUGAGCCCUCCUGCCACgt |
| 364 | 135 | UGGCAGGAGGGCUCACUCAtt | 742 | UGAGUGAGCCCUCCUGCCAcg |
| 365 | 136 | GGCAGGAGGGCUCACUCAAtt | 743 | UUGAGUGAGCCCUCCUGCCac |
| 366 | 137 | GCAGGAGGGCUCACUCAAAtt | 744 | UUUGAGUGAGCCCUCCUGCca |

TABLE 1-continued

RNAi molecule sequences for GST-7c

| Ref Pos | SEQ ID NO | SENSE STRAND (5'-->3') SEQ ID NOS: 2 to 608 | SEQ ID NO | ANTISENSE STRAND (5'-->3') SEQ ID NOS: 609 to 1215 |
|---|---|---|---|---|
| 367 | 138 | CAGGAGGGCUCACUCAAAGtt | 745 | CUUUGAGUGAGCCCUCCUGcc |
| 368 | 139 | AGGAGGGCUCACUCAAAGCtt | 746 | GCUUUGAGUGAGCCCUCCUGc |
| 369 | 140 | GGAGGGCUCACUCAAAGCCtt | 747 | GGCUUUGAGUGAGCCCUCCtg |
| 370 | 141 | GAGGGCUCACUCAAAGCCUtt | 748 | AGGCUUUGAGUGAGCCCUCct |
| 371 | 142 | AGGGCUCACUCAAAGCCUCtt | 749 | GAGGCUUUGAGUGAGCCCUcc |
| 372 | 143 | GGGCUCACUCAAAGCCUCCtt | 750 | GGAGGCUUUGAGUGAGCCCtc |
| 373 | 144 | GGCUCACUCAAAGCCUCCUtt | 751 | AGGAGGCUUUGAGUGAGCCct |
| 374 | 145 | GCUCACUCAAAGCCUCCUGtt | 752 | CAGGAGGCUUUGAGUGAGCcc |
| 375 | 146 | CUCACUCAAAGCCUCCUGCtt | 753 | GCAGGAGGCUUUGAGUGAGcc |
| 376 | 147 | UCACUCAAAGCCUCCUGCCtt | 754 | GGCAGGAGGCUUUGAGUGAgc |
| 377 | 148 | CACUCAAAGCCUCCUGCCUtt | 755 | AGGCAGGAGGCUUUGAGUGag |
| 378 | 149 | ACUCAAAGCCUCCUGCCUAtt | 756 | UAGGCAGGAGGCUUUGAGUga |
| 379 | 150 | CUCAAAGCCUCCUGCCUAUtt | 757 | AUAGGCAGGAGGCUUUGAGtg |
| 380 | 151 | UCAAAGCCUCCUGCCUAUAtt | 758 | UAUAGGCAGGAGGCUUUGAgt |
| 381 | 152 | CAAAGCCUCCUGCCUAUACtt | 759 | GUAUAGGCAGGAGGCUUUGag |
| 382 | 153 | AAAGCCUCCUGCCUAUACGtt | 760 | CGUAUAGGCAGGAGGCUUUga |
| 383 | 154 | AAGCCUCCUGCCUAUACGGtt | 761 | CCGUAUAGGCAGGAGGCUUtg |
| 384 | 155 | AGCCUCCUGCCUAUACGGGtt | 762 | CCCGUAUAGGCAGGAGGCUtt |
| 385 | 156 | GCCUCCUGCCUAUACGGGCtt | 763 | GCCCGUAUAGGCAGGAGGCtt |
| 386 | 157 | CCUCCUGCCUAUACGGGCAtt | 764 | UGCCCGUAUAGGCAGGAGGct |
| 387 | 158 | CUCCUGCCUAUACGGGCAGtt | 765 | CUGCCCGUAUAGGCAGGAGgc |
| 388 | 159 | UCCUGCCUAUACGGGCAGCtt | 766 | GCUGCCCGUAUAGGCAGGAgg |
| 389 | 160 | CCUGCCUAUACGGGCAGCUtt | 767 | AGCUGCCCGUAUAGGCAGGag |
| 390 | 161 | CUGCCUAUACGGGCAGCUCtt | 768 | GAGCUGCCCGUAUAGGCAGga |
| 391 | 162 | UGCCUAUACGGGCAGCUCCtt | 769 | GGAGCUGCCCGUAUAGGCAgg |
| 392 | 163 | GCCUAUACGGGCAGCUCCCtt | 770 | GGGAGCUGCCCGUAUAGGCag |
| 409 | 164 | CCCAAGUUCCAGGACGGAGtt | 771 | CUCCGUCCUGGAACUUGGGga |
| 410 | 165 | CCAAGUUCCAGGACGGAGAtt | 772 | UCUCCGUCCUGGAACUUGGgg |
| 411 | 166 | CAAGUUCCAGGACGGAGACtt | 773 | GUCUCCGUCCUGGAACUUGgg |
| 412 | 167 | AAGUUCCAGGACGGAGACCtt | 774 | GGUCUCCGUCCUGGAACUUgg |
| 413 | 168 | AGUUCCAGGACGGAGACCUtt | 775 | AGGUCUCCGUCCUGGAACUtg |
| 414 | 169 | GUUCCAGGACGGAGACCUCtt | 776 | GAGGUCUCCGUCCUGGAACtt |
| 415 | 170 | UUCCAGGACGGAGACCUCAtt | 777 | UGAGGUCUCCGUCCUGGAAct |
| 416 | 171 | UCCAGGACGGAGACCUCACtt | 778 | GUGAGGUCUCCGUCCUGGAac |
| 417 | 172 | CCAGGACGGAGACCUCACCtt | 779 | GGUGAGGUCUCCGUCCUGGaa |
| 418 | 173 | CAGGACGGAGACCUCACCCtt | 780 | GGGUGAGGUCUCCGUCCUGga |
| 419 | 174 | AGGACGGAGACCUCACCCUtt | 781 | AGGGUGAGGUCUCCGUCCUgg |

TABLE 1-continued

RNAi molecule sequences for GST-7c

| Ref Pos | SEQ ID NO | SENSE STRAND (5'-->3') SEQ ID NOS: 2 to 608 | SEQ ID NO | ANTISENSE STRAND (5'-->3') SEQ ID NOS: 609 to 1215 |
|---|---|---|---|---|
| 420 | 175 | GGACGGAGACCUCACCCUGtt | 782 | CAGGGUGAGGUCUCCGUCCtg |
| 421 | 176 | GACGGAGACCUCACCCUGUtt | 783 | ACAGGGUGAGGUCUCCGUCct |
| 422 | 177 | ACGGAGACCUCACCCUGUAtt | 784 | UACAGGGUGAGGUCUCCGUcc |
| 423 | 178 | CGGAGACCUCACCCUGUACtt | 785 | GUACAGGGUGAGGUCUCCGtc |
| 424 | 179 | GGAGACCUCACCCUGUACCtt | 786 | GGUACAGGGUGAGGUCUCCgt |
| 425 | 180 | GAGACCUCACCCUGUACCAtt | 787 | UGGUACAGGGUGAGGUCUCCg |
| 426 | 181 | AGACCUCACCCUGUACCAGtt | 788 | CUGGUACAGGGUGAGGUCUcc |
| 427 | 182 | GACCUCACCCUGUACCAGUtt | 789 | ACUGGUACAGGGUGAGGUCtc |
| 428 | 183 | ACCUCACCCUGUACCAGUCtt | 790 | GACUGGUACAGGGUGAGGUct |
| 429 | 184 | CCUCACCCUGUACCAGUCCtt | 791 | GGACUGGUACAGGGUGAGGtc |
| 430 | 185 | CUCACCCUGUACCAGUCCAtt | 792 | UGGACUGGUACAGGGUGAGgt |
| 431 | 186 | UCACCCUGUACCAGUCCAAtt | 793 | UUGGACUGGUACAGGGUGAgg |
| 432 | 187 | CACCCUGUACCAGUCCAAUtt | 794 | AUUGGACUGGUACAGGGUGag |
| 433 | 188 | ACCCUGUACCAGUCCAAUAtt | 795 | UAUUGGACUGGUACAGGGUga |
| 434 | 189 | CCCUGUACCAGUCCAAUACtt | 796 | GUAUUGGACUGGUACAGGGtg |
| 435 | 190 | CCUGUACCAGUCCAAUACCtt | 797 | GGUAUUGGACUGGUACAGGgt |
| 436 | 191 | CUGUACCAGUCCAAUACCAtt | 798 | UGGUAUUGGACUGGUACAGgg |
| 437 | 192 | UGUACCAGUCCAAUACCAUtt | 799 | AUGGUAUUGGACUGGUACAgg |
| 438 | 193 | GUACCAGUCCAAUACCAUCtt | 800 | GAUGGUAUUGGACUGGUACag |
| 439 | 194 | UACCAGUCCAAUACCAUCCtt | 801 | GGAUGGUAUUGGACUGGUAca |
| 440 | 195 | ACCAGUCCAAUACCAUCCUtt | 802 | AGGAUGGUAUUGGACUGGUac |
| 441 | 196 | CCAGUCCAAUACCAUCCUGtt | 803 | CAGGAUGGUAUUGGACUGGta |
| 442 | 197 | CAGUCCAAUACCAUCCUGCtt | 804 | GCAGGAUGGUAUUGGACUGgt |
| 443 | 198 | AGUCCAAUACCAUCCUGCGtt | 805 | CGCAGGAUGGUAUUGGACUgg |
| 444 | 199 | GUCCAAUACCAUCCUGCGUtt | 806 | ACGCAGGAUGGUAUUGGACtg |
| 445 | 200 | UCCAAUACCAUCCUGCGUCtt | 807 | GACGCAGGAUGGUAUUGGAct |
| 446 | 201 | CCAAUACCAUCCUGCGUCAtt | 808 | UGACGCAGGAUGGUAUUGGac |
| 447 | 202 | CAAUACCAUCCUGCGUCACtt | 809 | GUGACGCAGGAUGGUAUUGga |
| 448 | 203 | AAUACCAUCCUGCGUCACCtt | 810 | GGUGACGCAGGAUGGUAUUgg |
| 449 | 204 | AUACCAUCCUGCGUCACCUtt | 811 | AGGUGACGCAGGAUGGUAUtg |
| 450 | 205 | UACCAUCCUGCGUCACCUGtt | 812 | CAGGUGACGCAGGAUGGUAtt |
| 451 | 206 | ACCAUCCUGCGUCACCUGGtt | 813 | CCAGGUGACGCAGGAUGGUat |
| 452 | 207 | CCAUCCUGCGUCACCUGGGtt | 814 | CCCAGGUGACGCAGGAUGGta |
| 453 | 208 | CAUCCUGCGUCACCUGGGCtt | 815 | GCCCAGGUGACGCAGGAUGgt |
| 454 | 209 | AUCCUGCGUCACCUGGGCCtt | 816 | GGCCCAGGUGACGCAGGAUgg |
| 455 | 210 | UCCUGCGUCACCUGGGCCGtt | 817 | CGGCCCAGGUGACGCAGGAtg |
| 456 | 211 | CCUGCGUCACCUGGGCCGCtt | 818 | GCGGCCCAGGUGACGCAGGat |

TABLE 1-continued

RNAi molecule sequences for GST-7c

| Ref Pos | SEQ ID NO | SENSE STRAND (5'-->3') SEQ ID NOS: 2 to 608 | SEQ ID NO | ANTISENSE STRAND (5'-->3') SEQ ID NOS: 609 to 1215 |
|---|---|---|---|---|
| 457 | 212 | CUGCGUCACCUGGGCCGCAtt | 819 | UGCGGCCCAGGUGACGCAGga |
| 458 | 213 | UGCGUCACCUGGGCCGCACtt | 820 | GUGCGGCCCAGGUGACGCAgg |
| 459 | 214 | GCGUCACCUGGGCCGCACCtt | 821 | GGUGCGGCCCAGGUGACGCag |
| 460 | 215 | CGUCACCUGGGCCGCACCCtt | 822 | GGGUGCGGCCCAGGUGACGca |
| 461 | 216 | GUCACCUGGGCCGCACCCUtt | 823 | AGGGUGCGGCCCAGGUGACgc |
| 462 | 217 | UCACCUGGGCCGCACCCUUtt | 824 | AAGGGUGCGGCCCAGGUGAcg |
| 463 | 218 | CACCUGGGCCGCACCCUUGtt | 825 | CAAGGGUGCGGCCCAGGUGac |
| 464 | 219 | ACCUGGGCCGCACCCUUGGtt | 826 | CCAAGGGUGCGGCCCAGGUga |
| 465 | 220 | CCUGGGCCGCACCCUUGGGtt | 827 | CCCAAGGGUGCGGCCCAGGtg |
| 466 | 221 | CUGGGCCGCACCCUUGGGCtt | 828 | GCCCAAGGGUGCGGCCCAGgt |
| 467 | 222 | UGGGCCGCACCCUUGGGCUtt | 829 | AGCCCAAGGGUGCGGCCCAgg |
| 468 | 223 | GGGCCGCACCCUUGGGCUCtt | 830 | GAGCCCAAGGGUGCGGCCCag |
| 469 | 224 | GGCCGCACCCUUGGGCUCUtt | 831 | AGAGCCCAAGGGUGCGGCCa |
| 470 | 225 | GCCGCACCCUUGGGCUCUAtt | 832 | UAGAGCCCAAGGGUGCGGCcc |
| 471 | 226 | CCGCACCCUUGGGCUCUAUtt | 833 | AUAGAGCCCAAGGGUGCGGcc |
| 472 | 227 | CGCACCCUUGGGCUCUAUGtt | 834 | CAUAGAGCCCAAGGGUGCGgc |
| 473 | 228 | GCACCCUUGGGCUCUAUGGtt | 835 | CCAUAGAGCCCAAGGGUGCgg |
| 474 | 229 | CACCCUUGGGCUCUAUGGGtt | 836 | CCCAUAGAGCCCAAGGGUGcg |
| 475 | 230 | ACCCUUGGGCUCUAUGGGAtt | 837 | UCCCAUAGAGCCCAAGGGUgc |
| 476 | 231 | CCCUUGGGCUCUAUGGGAAtt | 838 | UUCCCAUAGAGCCCAAGGGtg |
| 477 | 232 | CCUUGGGCUCUAUGGGAAGtt | 839 | CUUCCCAUAGAGCCCAAGGgt |
| 478 | 233 | CUUGGGCUCUAUGGGAAGGtt | 840 | CCUUCCCAUAGAGCCCAAGgg |
| 479 | 234 | UUGGGCUCUAUGGGAAGGAtt | 841 | UCCUUCCCAUAGAGCCCAAgg |
| 480 | 235 | UGGGCUCUAUGGGAAGGACtt | 842 | GUCCUUCCCAUAGAGCCCAag |
| 481 | 236 | GGGCUCUAUGGGAAGGACCtt | 843 | GGUCCUUCCCAUAGAGCCCaa |
| 482 | 237 | GGCUCUAUGGGAAGGACCAtt | 844 | UGGUCCUUCCCAUAGAGCCca |
| 483 | 238 | GCUCUAUGGGAAGGACCAGtt | 845 | CUGGUCCUUCCCAUAGAGCcc |
| 484 | 239 | CUCUAUGGGAAGGACCAGCtt | 846 | GCUGGUCCUUCCCAUAGAGcc |
| 485 | 240 | UCUAUGGGAAGGACCAGCAtt | 847 | UGCUGGUCCUUCCCAUAGAgc |
| 486 | 241 | CUAUGGGAAGGACCAGCAGtt | 848 | CUGCUGGUCCUUCCCAUAGag |
| 487 | 242 | UAUGGGAAGGACCAGCAGGtt | 849 | CCUGCUGGUCCUUCCCAUAga |
| 488 | 243 | AUGGGAAGGACCAGCAGGAtt | 850 | UCCUGCUGGUCCUUCCCAUag |
| 489 | 244 | UGGGAAGGACCAGCAGGAGtt | 851 | CUCCUGCUGGUCCUUCCCAta |
| 490 | 245 | GGGAAGGACCAGCAGGAGGtt | 852 | CCUCCUGCUGGUCCUUCCCat |
| 491 | 246 | GGAAGGACCAGCAGGAGGCtt | 853 | GCCUCCUGCUGGUCCUUCCca |
| 492 | 247 | GAAGGACCAGCAGGAGGCAtt | 854 | UGCCUCCUGCUGGUCCUUCcc |
| 493 | 248 | AAGGACCAGCAGGAGGCAGtt | 855 | CUGCCUCCUGCUGGUCCUUcc |

TABLE 1-continued

RNAi molecule sequences for GST-7c

| Ref Pos | SEQ ID NO | SENSE STRAND (5'-->3') SEQ ID NOS: 2 to 608 | SEQ ID NO | ANTISENSE STRAND (5'-->3') SEQ ID NOS: 609 to 1215 |
|---|---|---|---|---|
| 494 | 249 | AGGACCAGCAGGAGGCAGCtt | 856 | GCUGCCUCCUGCUGGUCCUtc |
| 495 | 250 | GGACCAGCAGGAGGCAGCCtt | 857 | GGCUGCCUCCUGCUGGUCCtt |
| 496 | 251 | GACCAGCAGGAGGCAGCCCtt | 858 | GGGCUGCCUCCUGCUGGUCct |
| 497 | 252 | ACCAGCAGGAGGCAGCCCUtt | 859 | AGGGCUGCCUCCUGCUGGUcc |
| 498 | 253 | CCAGCAGGAGGCAGCCCUGtt | 860 | CAGGGCUGCCUCCUGCUGGtc |
| 499 | 254 | CAGCAGGAGGCAGCCCUGGtt | 861 | CCAGGGCUGCCUCCUGCUGgt |
| 500 | 255 | AGCAGGAGGCAGCCCUGGUtt | 862 | ACCAGGGCUGCCUCCUGCUgg |
| 501 | 256 | GCAGGAGGCAGCCCUGGUGtt | 863 | CACCAGGGCUGCCUCCUGCtg |
| 502 | 257 | CAGGAGGCAGCCCUGGUGGtt | 864 | CCACCAGGGCUGCCUCCUGct |
| 503 | 258 | AGGAGGCAGCCCUGGUGGAtt | 865 | UCCACCAGGGCUGCCUCCUgc |
| 504 | 259 | GGAGGCAGCCCUGGUGGACtt | 866 | GUCCACCAGGGCUGCCUCCtg |
| 505 | 260 | GAGGCAGCCCUGGUGGACAtt | 867 | UGUCCACCAGGGCUGCCUCct |
| 506 | 261 | AGGCAGCCCUGGUGGACAUtt | 868 | AUGUCCACCAGGGCUGCCUcc |
| 507 | 262 | GGCAGCCCUGGUGGACAUGtt | 869 | CAUGUCCACCAGGGCUGCCtc |
| 508 | 263 | GCAGCCCUGGUGGACAUGGtt | 870 | CCAUGUCCACCAGGGCUGCct |
| 509 | 264 | CAGCCCUGGUGGACAUGGUtt | 871 | ACCAUGUCCACCAGGGCUGcc |
| 510 | 265 | AGCCCUGGUGGACAUGGUGtt | 872 | CACCAUGUCCACCAGGGCUgc |
| 511 | 266 | GCCCUGGUGGACAUGGUGAtt | 873 | UCACCAUGUCCACCAGGGCtg |
| 512 | 267 | CCCUGGUGGACAUGGUGAAtt | 874 | UUCACCAUGUCCACCAGGGct |
| 513 | 268 | CCUGGUGGACAUGGUGAAUtt | 875 | AUUCACCAUGUCCACCAGGgc |
| 514 | 269 | CUGGUGGACAUGGUGAAUGtt | 876 | CAUUCACCAUGUCCACCAGgg |
| 515 | 270 | UGGUGGACAUGGUGAAUGAtt | 877 | UCAUUCACCAUGUCCACCAgg |
| 516 | 271 | GGUGGACAUGGUGAAUGACtt | 878 | GUCAUUCACCAUGUCCACCag |
| 517 | 272 | GUGGACAUGGUGAAUGACGtt | 879 | CGUCAUUCACCAUGUCCACca |
| 518 | 273 | UGGACAUGGUGAAUGACGGtt | 880 | CCGUCAUUCACCAUGUCCAcc |
| 519 | 274 | GGACAUGGUGAAUGACGGCtt | 881 | GCCGUCAUUCACCAUGUCCac |
| 520 | 275 | GACAUGGUGAAUGACGGCGtt | 882 | CGCCGUCAUUCACCAUGUCca |
| 521 | 276 | ACAUGGUGAAUGACGGCGUtt | 883 | ACGCCGUCAUUCACCAUGUcc |
| 522 | 277 | CAUGGUGAAUGACGGCGUGtt | 884 | CACGCCGUCAUUCACCAUGtc |
| 523 | 278 | AUGGUGAAUGACGGCGUGGtt | 885 | CCACGCCGUCAUUCACCAUgt |
| 524 | 279 | UGGUGAAUGACGGCGUGGAtt | 886 | UCCACGCCGUCAUUCACCAtg |
| 525 | 280 | GGUGAAUGACGGCGUGGAGtt | 887 | CUCCACGCCGUCAUUCACCat |
| 526 | 281 | GUGAAUGACGGCGUGGAGGtt | 888 | CCUCCACGCCGUCAUUCACca |
| 527 | 282 | UGAAUGACGGCGUGGAGGAtt | 889 | UCCUCCACGCCGUCAUUCAcc |
| 528 | 283 | GAAUGACGGCGUGGAGGACtt | 890 | GUCCUCCACGCCGUCAUUCac |
| 529 | 284 | AAUGACGGCGUGGAGGACCtt | 891 | GGUCCUCCACGCCGUCAUUca |
| 530 | 285 | AUGACGGCGUGGAGGACCUtt | 892 | AGGUCCUCCACGCCGUCAUtc |

TABLE 1-continued

RNAi molecule sequences for GST-7c

| Ref Pos | SEQ ID NO | SENSE STRAND (5'-->3') SEQ ID NOS: 2 to 608 | SEQ ID NO | ANTISENSE STRAND (5'-->3') SEQ ID NOS: 609 to 1215 |
|---|---|---|---|---|
| 531 | 286 | UGACGGCGUGGAGGACCUCtt | 893 | GAGGUCCUCCACGCCGUCAtt |
| 532 | 287 | GACGGCGUGGAGGACCUCCtt | 894 | GGAGGUCCUCCACGCCGUCat |
| 533 | 288 | ACGGCGUGGAGGACCUCCGtt | 895 | CGGAGGUCCUCCACGCCGUca |
| 534 | 289 | CGGCGUGGAGGACCUCCGCtt | 896 | GCGGAGGUCCUCCACGCCGtc |
| 535 | 290 | GGCGUGGAGGACCUCCGCUtt | 897 | AGCGGAGGUCCUCCACGCCgt |
| 536 | 291 | GCGUGGAGGACCUCCGCUGtt | 898 | CAGCGGAGGUCCUCCACGCcg |
| 537 | 292 | CGUGGAGGACCUCCGCUGCtt | 899 | GCAGCGGAGGUCCUCCACGcc |
| 538 | 293 | GUGGAGGACCUCCGCUGCAtt | 900 | UGCAGCGGAGGUCCUCCACgc |
| 539 | 294 | UGGAGGACCUCCGCUGCAAtt | 901 | UUGCAGCGGAGGUCCUCCAcg |
| 540 | 295 | GGAGGACCUCCGCUGCAAAtt | 902 | UUUGCAGCGGAGGUCCUCCac |
| 541 | 296 | GAGGACCUCCGCUGCAAAUtt | 903 | AUUUGCAGCGGAGGUCCUCca |
| 542 | 297 | AGGACCUCCGCUGCAAAUAtt | 904 | UAUUUGCAGCGGAGGUCCUcc |
| 543 | 298 | GGACCUCCGCUGCAAAUACtt | 905 | GUAUUUGCAGCGGAGGUCCtc |
| 544 | 299 | GACCUCCGCUGCAAAUACAtt | 906 | UGUAUUUGCAGCGGAGGUCct |
| 545 | 300 | ACCUCCGCUGCAAAUACAUtt | 907 | AUGUAUUUGCAGCGGAGGUcc |
| 546 | 301 | CCUCCGCUGCAAAUACAUCtt | 908 | GAUGUAUUUGCAGCGGAGGtc |
| 547 | 302 | CUCCGCUGCAAAUACAUCUtt | 909 | AGAUGUAUUUGCAGCGGAGgt |
| 548 | 303 | UCCGCUGCAAAUACAUCUCtt | 910 | GAGAUGUAUUUGCAGCGGAgg |
| 549 | 304 | CCGCUGCAAAUACAUCUCCtt | 911 | GGAGAUGUAUUUGCAGCGGag |
| 550 | 305 | CGCUGCAAAUACAUCUCCCtt | 912 | GGGAGAUGUAUUUGCAGCGga |
| 551 | 306 | GCUGCAAAUACAUCUCCCUtt | 913 | AGGGAGAUGUAUUUGCAGCgg |
| 552 | 307 | CUGCAAAUACAUCUCCCUCtt | 914 | GAGGGAGAUGUAUUUGCAGcg |
| 553 | 308 | UGCAAAUACAUCUCCCUCAtt | 915 | UGAGGGAGAUGUAUUUGCAgc |
| 554 | 309 | GCAAAUACAUCUCCCUCAUtt | 916 | AUGAGGGAGAUGUAUUUGCag |
| 555 | 310 | CAAAUACAUCUCCCUCAUCtt | 917 | GAUGAGGGAGAUGUAUUUGca |
| 556 | 311 | AAAUACAUCUCCCUCAUCUtt | 918 | AGAUGAGGGAGAUGUAUUUgc |
| 557 | 312 | AAUACAUCUCCCUCAUCUAtt | 919 | UAGAUGAGGGAGAUGUAUUtg |
| 558 | 313 | AUACAUCUCCCUCAUCUACtt | 920 | GUAGAUGAGGGAGAUGUAUtt |
| 559 | 314 | UACAUCUCCCUCAUCUACAtt | 921 | UGUAGAUGAGGGAGAUGUAtt |
| 560 | 315 | ACAUCUCCCUCAUCUACACtt | 922 | GUGUAGAUGAGGGAGAUGUat |
| 561 | 316 | CAUCUCCCUCAUCUACACCtt | 923 | GGUGUAGAUGAGGGAGAUGta |
| 562 | 317 | AUCUCCCUCAUCUACACCAtt | 924 | UGGUGUAGAUGAGGGAGAUgt |
| 563 | 318 | UCUCCCUCAUCUACACCAAtt | 925 | UUGGUGUAGAUGAGGGAGAtg |
| 563 | 319 | GCUCCCUCAUCUACACCAAtt | 926 | UUGGUGUAGAUGAGGGAGCtg |
| 564 | 320 | CUCCCUCAUCUACACCAACtt | 927 | GUUGGUGUAGAUGAGGGAGat |
| 565 | 321 | UCCCUCAUCUACACCAACUtt | 928 | AGUUGGUGUAGAUGAGGGAga |
| 565 | 322 | CUCCCUCAUCUACACCAAAtt | 929 | UUUGGUGUAGAUGAGGGAGat |

TABLE 1-continued

RNAi molecule sequences for GST-7c

| Ref Pos | SEQ ID NO | SENSE STRAND (5'-->3') SEQ ID NOS: 2 to 608 | SEQ ID NO | ANTISENSE STRAND (5'-->3') SEQ ID NOS: 609 to 1215 |
|---|---|---|---|---|
| 566 | 323 | CCCUCAUCUACACCAACUAtt | 930 | UAGUUGGUGUAGAUGAGGGag |
| 567 | 324 | CCUCAUCUACACCAACUAUtt | 931 | AUAGUUGGUGUAGAUGAGGga |
| 567 | 325 | CCUCAUCUACACCAACUAAtt | 932 | UUAGUUGGUGUAGAUGAGGga |
| 568 | 326 | CUCAUCUACACCAACUAUGtt | 933 | CAUAGUUGGUGUAGAUGAGgg |
| 569 | 327 | UCAUCUACACCAACUAUGAtt | 934 | UCAUAGUUGGUGUAGAUGAgg |
| 570 | 328 | CAUCUACACCAACUAUGAGtt | 935 | CUCAUAGUUGGUGUAGAUGag |
| 571 | 329 | AUCUACACCAACUAUGAGGtt | 936 | CCUCAUAGUUGGUGUAGAUga |
| 572 | 330 | UCUACACCAACUAUGAGGCtt | 937 | GCCUCAUAGUUGGUGUAGAtg |
| 573 | 331 | CUACACCAACUAUGAGGCGtt | 938 | CGCCUCAUAGUUGGUGUAGat |
| 574 | 332 | UACACCAACUAUGAGGCGGtt | 939 | CCGCCUCAUAGUUGGUGUAga |
| 575 | 333 | ACACCAACUAUGAGGCGGGtt | 940 | CCCGCCUCAUAGUUGGUGUag |
| 576 | 334 | CACCAACUAUGAGGCGGGCtt | 941 | GCCCGCCUCAUAGUUGGUGta |
| 577 | 335 | ACCAACUAUGAGGCGGGCAtt | 942 | UGCCCGCCUCAUAGUUGGUgt |
| 578 | 336 | CCAACUAUGAGGCGGGCAAtt | 943 | UUGCCCGCCUCAUAGUUGGtg |
| 579 | 337 | CAACUAUGAGGCGGGCAAGtt | 944 | CUUGCCCGCCUCAUAGUUGgt |
| 580 | 338 | AACUAUGAGGCGGGCAAGGtt | 945 | CCUUGCCCGCCUCAUAGUUgg |
| 581 | 339 | ACUAUGAGGCGGGCAAGGAtt | 946 | UCCUUGCCCGCCUCAUAGUtg |
| 582 | 340 | CUAUGAGGCGGGCAAGGAUtt | 947 | AUCCUUGCCCGCCUCAUAGtt |
| 583 | 341 | UAUGAGGCGGGCAAGGAUGtt | 948 | CAUCCUUGCCCGCCUCAUAgt |
| 584 | 342 | AUGAGGCGGGCAAGGAUGAtt | 949 | UCAUCCUUGCCCGCCUCAUag |
| 585 | 343 | UGAGGCGGGCAAGGAUGACtt | 950 | GUCAUCCUUGCCCGCCUCAta |
| 586 | 344 | GAGGCGGGCAAGGAUGACUtt | 951 | AGUCAUCCUUGCCCGCCUCat |
| 587 | 345 | AGGCGGGCAAGGAUGACUAtt | 952 | UAGUCAUCCUUGCCCGCCUca |
| 588 | 346 | GGCGGGCAAGGAUGACUAUtt | 953 | AUAGUCAUCCUUGCCCGCCtc |
| 589 | 347 | GCGGGCAAGGAUGACUAUGtt | 954 | CAUAGUCAUCCUUGCCCGCct |
| 590 | 348 | CGGGCAAGGAUGACUAUGUtt | 955 | ACAUAGUCAUCCUUGCCCGcc |
| 591 | 349 | GGGCAAGGAUGACUAUGUGtt | 956 | CACAUAGUCAUCCUUGCCCgc |
| 592 | 350 | GGCAAGGAUGACUAUGUGAtt | 957 | UCACAUAGUCAUCCUUGCCcg |
| 593 | 351 | GCAAGGAUGACUAUGUGAAtt | 958 | UUCACAUAGUCAUCCUUGCcc |
| 594 | 352 | CAAGGAUGACUAUGUGAAGtt | 959 | CUUCACAUAGUCAUCCUUGcc |
| 595 | 353 | AAGGAUGACUAUGUGAAGGtt | 960 | CCUUCACAUAGUCAUCCUUgc |
| 596 | 354 | AGGAUGACUAUGUGAAGGCtt | 961 | GCCUUCACAUAGUCAUCCUtg |
| 597 | 355 | GGAUGACUAUGUGAAGGCAtt | 962 | UGCCUUCACAUAGUCAUCCtt |
| 598 | 356 | GAUGACUAUGUGAAGGCACtt | 963 | GUGCCUUCACAUAGUCAUCct |
| 599 | 357 | AUGACUAUGUGAAGGCACUtt | 964 | AGUGCCUUCACAUAGUCAUcc |
| 600 | 358 | UGACUAUGUGAAGGCACUGtt | 965 | CAGUGCCUUCACAUAGUCAtc |
| 601 | 359 | GACUAUGUGAAGGCACUGCtt | 966 | GCAGUGCCUUCACAUAGUCat |

TABLE 1-continued

RNAi molecule sequences for GST-7c

| Ref Pos | SEQ ID NO | SENSE STRAND (5'-->3') SEQ ID NOS: 2 to 608 | SEQ ID NO | ANTISENSE STRAND (5'-->3') SEQ ID NOS: 609 to 1215 |
|---|---|---|---|---|
| 602 | 360 | ACUAUGUGAAGGCACUGCCtt | 967 | GGCAGUGCCUUCACAUAGUca |
| 603 | 361 | CUAUGUGAAGGCACUGCCCtt | 968 | GGGCAGUGCCUUCACAUAGtc |
| 604 | 362 | UAUGUGAAGGCACUGCCCGtt | 969 | CGGGCAGUGCCUUCACAUAgt |
| 605 | 363 | AUGUGAAGGCACUGCCCGGtt | 970 | CCGGGCAGUGCCUUCACAUag |
| 606 | 364 | UGUGAAGGCACUGCCCGGGtt | 971 | CCCGGGCAGUGCCUUCACAta |
| 607 | 365 | GUGAAGGCACUGCCCGGGCtt | 972 | GCCCGGGCAGUGCCUUCACat |
| 608 | 366 | UGAAGGCACUGCCCGGGCAtt | 973 | UGCCCGGGCAGUGCCUUCAca |
| 609 | 367 | GAAGGCACUGCCCGGGCAAtt | 974 | UUGCCCGGGCAGUGCCUUCac |
| 610 | 368 | AAGGCACUGCCCGGGCAACtt | 975 | GUUGCCCGGGCAGUGCCUUca |
| 611 | 369 | AGGCACUGCCCGGGCAACUtt | 976 | AGUUGCCCGGGCAGUGCCUtc |
| 612 | 370 | GGCACUGCCCGGGCAACUGtt | 977 | CAGUUGCCCGGGCAGUGCCtt |
| 613 | 371 | GCACUGCCCGGGCAACUGAtt | 978 | UCAGUUGCCCGGGCAGUGCct |
| 614 | 372 | CACUGCCCGGGCAACUGAAtt | 979 | UUCAGUUGCCCGGGCAGUGcc |
| 615 | 373 | ACUGCCCGGGCAACUGAAGtt | 980 | CUUCAGUUGCCCGGGCAGUgc |
| 616 | 374 | CUGCCCGGGCAACUGAAGCtt | 981 | GCUUCAGUUGCCCGGGCAGtg |
| 617 | 375 | UGCCCGGGCAACUGAAGCCtt | 982 | GGCUUCAGUUGCCCGGGCAgt |
| 618 | 376 | GCCCGGGCAACUGAAGCCUtt | 983 | AGGCUUCAGUUGCCCGGGCag |
| 619 | 377 | CCCGGGCAACUGAAGCCUUtt | 984 | AAGGCUUCAGUUGCCCGGGca |
| 620 | 378 | CCGGGCAACUGAAGCCUUUtt | 985 | AAAGGCUUCAGUUGCCCGGgc |
| 621 | 379 | CGGGCAACUGAAGCCUUUUtt | 986 | AAAAGGCUUCAGUUGCCCGgg |
| 622 | 380 | GGGCAACUGAAGCCUUUUGtt | 987 | CAAAAGGCUUCAGUUGCCCgg |
| 623 | 381 | GGCAACUGAAGCCUUUUGAtt | 988 | UCAAAAGGCUUCAGUUGCCcg |
| 624 | 382 | GCAACUGAAGCCUUUUGAGtt | 989 | CUCAAAAGGCUUCAGUUGCcc |
| 625 | 383 | CAACUGAAGCCUUUUGAGAtt | 990 | UCUCAAAAGGCUUCAGUUGcc |
| 626 | 384 | AACUGAAGCCUUUUGAGACtt | 991 | GUCUCAAAAGGCUUCAGUUgc |
| 627 | 385 | ACUGAAGCCUUUUGAGACCtt | 992 | GGUCUCAAAAGGCUUCAGUtg |
| 627 | 386 | ACUGAAGCCUUUUGAGACAtt | 993 | UGUCUCAAAAGGCUUCAGUtg |
| 628 | 387 | CUGAAGCCUUUUGAGACCCtt | 994 | GGGUCUCAAAAGGCUUCAGtt |
| 629 | 388 | UGAAGCCUUUUGAGACCCUtt | 995 | AGGGUCUCAAAAGGCUUCAgt |
| 630 | 389 | GAAGCCUUUUGAGACCCUGtt | 996 | CAGGGUCUCAAAAGGCUUCag |
| 631 | 390 | AAGCCUUUUGAGACCCUGCtt | 997 | GCAGGGUCUCAAAAGGCUUca |
| 631 | 391 | GAAGCCUUUUGAGACCCUAtt | 998 | UAGGGUCUCAAAAGGCUUCag |
| 632 | 392 | AGCCUUUUGAGACCCUGCUtt | 999 | AGCAGGGUCUCAAAAGGCUtc |
| 632 | 393 | CGCCUUUUGAGACCCUGCAtt | 1000 | UGCAGGGUCUCAAAAGGCGtc |
| 632 | 394 | AGCCUUUUGAGACCCUGCAtt | 1001 | UGCAGGGUCUCAAAAGGCUtc |
| 633 | 395 | GCCUUUUGAGACCCUGCUGtt | 1002 | CAGCAGGGUCUCAAAAGGCtt |
| 634 | 396 | CCUUUUGAGACCCUGCUGUtt | 1003 | ACAGCAGGGUCUCAAAAGGct |

TABLE 1-continued

RNAi molecule sequences for GST-7c

| Ref Pos | SEQ ID NO | SENSE STRAND (5'-->3') SEQ ID NOS: 2 to 608 | SEQ ID NO | ANTISENSE STRAND (5'-->3') SEQ ID NOS: 609 to 1215 |
|---|---|---|---|---|
| 634 | 397 | CCUUUUGAGACCCUGCUGAtt | 1004 | UCAGCAGGGUCUCAAAAGGct |
| 635 | 398 | CUUUUGAGACCCUGCUGUCtt | 1005 | GACAGCAGGGUCUCAAAAGgc |
| 635 | 399 | CUUUUGAGACCCUGCUGUAtt | 1006 | UACAGCAGGGUCUCAAAAGgc |
| 636 | 400 | UUUUGAGACCCUGCUGUCCtt | 1007 | GGACAGCAGGGUCUCAAAAgg |
| 637 | 401 | UUUGAGACCCUGCUGUCCCtt | 1008 | GGGACAGCAGGGUCUCAAAag |
| 638 | 402 | UUGAGACCCUGCUGUCCCAtt | 1009 | UGGGACAGCAGGGUCUCAAaa |
| 639 | 403 | UGAGACCCUGCUGUCCCAGtt | 1010 | CUGGGACAGCAGGGUCUCAaa |
| 640 | 404 | GAGACCCUGCUGUCCCAGAtt | 1011 | UCUGGGACAGCAGGGUCUCaa |
| 641 | 405 | AGACCCUGCUGUCCCAGAAtt | 1012 | UUCUGGGACAGCAGGGUCUca |
| 642 | 406 | GACCCUGCUGUCCCAGAACtt | 1013 | GUUCUGGGACAGCAGGGUCtc |
| 643 | 407 | ACCCUGCUGUCCCAGAACCtt | 1014 | GGUUCUGGGACAGCAGGGUct |
| 643 | 408 | ACCCUGCUGUCCCAGAACAtt | 1015 | UGUUCUGGGACAGCAGGGUct |
| 644 | 409 | CCCUGCUGUCCCAGAACCAtt | 1016 | UGGUUCUGGGACAGCAGGGtc |
| 645 | 410 | CCUGCUGUCCCAGAACCAGtt | 1017 | CUGGUUCUGGGACAGCAGGgt |
| 646 | 411 | CUGCUGUCCCAGAACCAGGtt | 1018 | CCUGGUUCUGGGACAGCAGgg |
| 647 | 412 | UGCUGUCCCAGAACCAGGGtt | 1019 | CCCUGGUUCUGGGACAGCAgg |
| 648 | 413 | UGCUGUCCCAGAACCAGGAtt | 1020 | UCCUGGUUCUGGGACAGCAgg |
| 648 | 414 | GCUGUCCCAGAACCAGGGAtt | 1021 | UCCCUGGUUCUGGGACAGCag |
| 649 | 415 | CUGUCCCAGAACCAGGGAGtt | 1022 | CUCCCUGGUUCUGGGACAGca |
| 650 | 416 | UGUCCCAGAACCAGGGAGGtt | 1023 | CCUCCCUGGUUCUGGGACAgc |
| 651 | 417 | GUCCCAGAACCAGGGAGGCtt | 1024 | GCCUCCCUGGUUCUGGGACag |
| 652 | 418 | UCCCAGAACCAGGGAGGCAtt | 1025 | UGCCUCCCUGGUUCUGGGAca |
| 653 | 419 | CCCAGAACCAGGGAGGCAAtt | 1026 | UUGCCUCCCUGGUUCUGGGac |
| 654 | 420 | CCAGAACCAGGGAGGCAAGtt | 1027 | CUUGCCUCCCUGGUUCUGGga |
| 655 | 421 | CAGAACCAGGGAGGCAAGAtt | 1028 | UCUUGCCUCCCUGGUUCUGgg |
| 656 | 422 | AGAACCAGGGAGGCAAGACtt | 1029 | GUCUUGCCUCCCUGGUUCUgg |
| 657 | 423 | GAACCAGGGAGGCAAGACCtt | 1030 | GGUCUUGCCUCCCUGGUUCtg |
| 658 | 424 | AACCAGGGAGGCAAGACCUtt | 1031 | AGGUCUUGCCUCCCUGGUUct |
| 659 | 425 | ACCAGGGAGGCAAGACCUUtt | 1032 | AAGGUCUUGCCUCCCUGGUtc |
| 660 | 426 | CCAGGGAGGCAAGACCUUCtt | 1033 | GAAGGUCUUGCCUCCCUGGtt |
| 661 | 427 | CAGGGAGGCAAGACCUUCAtt | 1034 | UGAAGGUCUUGCCUCCCUGgt |
| 662 | 428 | AGGGAGGCAAGACCUUCAUtt | 1035 | AUGAAGGUCUUGCCUCCCUgg |
| 663 | 429 | GGGAGGCAAGACCUUCAUUtt | 1036 | AAUGAAGGUCUUGCCUCCCtg |
| 664 | 430 | GGAGGCAAGACCUUCAUUGtt | 1037 | CAAUGAAGGUCUUGCCUCCct |
| 665 | 431 | GAGGCAAGACCUUCAUUGUtt | 1038 | ACAAUGAAGGUCUUGCCUCcc |
| 666 | 432 | AGGCAAGACCUUCAUUGUGtt | 1039 | CACAAUGAAGGUCUUGCCUcc |
| 667 | 433 | GGCAAGACCUUCAUUGUGGtt | 1040 | CCACAAUGAAGGUCUUGCCtc |

TABLE 1-continued

RNAi molecule sequences for GST-7c

| Ref Pos | SEQ ID NO | SENSE STRAND (5'-->3') SEQ ID NOS: 2 to 608 | SEQ ID NO | ANTISENSE STRAND (5'-->3') SEQ ID NOS: 609 to 1215 |
|---|---|---|---|---|
| 668 | 434 | GCAAGACCUUCAUUGUGGGtt | 1041 | CCCACAAUGAAGGUCUUGCct |
| 669 | 435 | CAAGACCUUCAUUGUGGGAtt | 1042 | UCCCACAAUGAAGGUCUUGcc |
| 670 | 436 | AAGACCUUCAUUGUGGGAGtt | 1043 | CUCCCACAAUGAAGGUCUUGc |
| 671 | 437 | AGACCUUCAUUGUGGGAGAtt | 1044 | UCUCCCACAAUGAAGGUCUtg |
| 672 | 438 | GACCUUCAUUGUGGGAGACtt | 1045 | GUCUCCCACAAUGAAGGUCtt |
| 673 | 439 | ACCUUCAUUGUGGGAGACCtt | 1046 | GGUCUCCCACAAUGAAGGUct |
| 674 | 440 | CCUUCAUUGUGGGAGACCAtt | 1047 | UGGUCUCCCACAAUGAAGGtc |
| 675 | 441 | CUUCAUUGUGGGAGACCAGtt | 1048 | CUGGUCUCCCACAAUGAAGgt |
| 676 | 442 | UUCAUUGUGGGAGACCAGAtt | 1049 | UCUGGUCUCCCACAAUGAAgg |
| 677 | 443 | UCAUUGUGGGAGACCAGAUtt | 1050 | AUCUGGUCUCCCACAAUGAag |
| 678 | 444 | CAUUGUGGGAGACCAGAUCtt | 1051 | GAUCUGGUCUCCCACAAUGaa |
| 679 | 445 | AUUGUGGGAGACCAGAUCUtt | 1052 | AGAUCUGGUCUCCCACAAUga |
| 680 | 446 | UUGUGGGAGACCAGAUCUCtt | 1053 | GAGAUCUGGUCUCCCACAAtg |
| 681 | 447 | UGUGGGAGACCAGAUCUCCtt | 1054 | GGAGAUCUGGUCUCCCACAat |
| 682 | 448 | GUGGGAGACCAGAUCUCCUtt | 1055 | AGGAGAUCUGGUCUCCCACaa |
| 683 | 449 | UGGGAGACCAGAUCUCCUUtt | 1056 | AAGGAGAUCUGGUCUCCCAca |
| 684 | 450 | GGGAGACCAGAUCUCCUUCtt | 1057 | GAAGGAGAUCUGGUCUCCCac |
| 685 | 451 | GGAGACCAGAUCUCCUUCGtt | 1058 | CGAAGGAGAUCUGGUCUCCca |
| 686 | 452 | GAGACCAGAUCUCCUUCGCtt | 1059 | GCGAAGGAGAUCUGGUCUCcc |
| 687 | 453 | AGACCAGAUCUCCUUCGCUtt | 1060 | AGCGAAGGAGAUCUGGUCUcc |
| 688 | 454 | GACCAGAUCUCCUUCGCUGtt | 1061 | CAGCGAAGGAGAUCUGGUCtc |
| 689 | 455 | ACCAGAUCUCCUUCGCUGAtt | 1062 | UCAGCGAAGGAGAUCUGGUct |
| 690 | 456 | CCAGAUCUCCUUCGCUGACtt | 1063 | GUCAGCGAAGGAGAUCUGGtc |
| 691 | 457 | CAGAUCUCCUUCGCUGACUtt | 1064 | AGUCAGCGAAGGAGAUCUGgt |
| 692 | 458 | AGAUCUCCUUCGCUGACUAtt | 1065 | UAGUCAGCGAAGGAGAUCUgg |
| 693 | 459 | GAUCUCCUUCGCUGACUACtt | 1066 | GUAGUCAGCGAAGGAGAUCtg |
| 694 | 460 | AUCUCCUUCGCUGACUACAtt | 1067 | UGUAGUCAGCGAAGGAGAUct |
| 695 | 461 | UCUCCUUCGCUGACUACAAtt | 1068 | UUGUAGUCAGCGAAGGAGAtc |
| 696 | 462 | CUCCUUCGCUGACUACAACtt | 1069 | GUUGUAGUCAGCGAAGGAGat |
| 697 | 463 | UCCUUCGCUGACUACAACCtt | 1070 | GGUUGUAGUCAGCGAAGGAga |
| 698 | 464 | CCUUCGCUGACUACAACCUtt | 1071 | AGGUUGUAGUCAGCGAAGGag |
| 699 | 465 | CUUCGCUGACUACAACCUGtt | 1072 | CAGGUUGUAGUCAGCGAAGga |
| 700 | 466 | UUCGCUGACUACAACCUGCtt | 1073 | GCAGGUUGUAGUCAGCGAAgg |
| 701 | 467 | UCGCUGACUACAACCUGCUtt | 1074 | AGCAGGUUGUAGUCAGCGAag |
| 702 | 468 | CGCUGACUACAACCUGCUGtt | 1075 | CAGCAGGUUGUAGUCAGCGaa |
| 703 | 469 | GCUGACUACAACCUGCUGGtt | 1076 | CCAGCAGGUUGUAGUCAGCga |
| 704 | 470 | CUGACUACAACCUGCUGGAtt | 1077 | UCCAGCAGGUUGUAGUCAGcg |

TABLE 1-continued

RNAi molecule sequences for GST-7c

| Ref Pos | SEQ ID NO | SENSE STRAND (5'-->3') SEQ ID NOS: 2 to 608 | SEQ ID NO | ANTISENSE STRAND (5'-->3') SEQ ID NOS: 609 to 1215 |
|---|---|---|---|---|
| 705 | 471 | UGACUACAACCUGCUGGACUtt | 1078 | GUCCAGCAGGUUGUAGUCAgc |
| 706 | 472 | GACUACAACCUGCUGGACUUtt | 1079 | AGUCCAGCAGGUUGUAGUCag |
| 707 | 473 | ACUACAACCUGCUGGACUUtt | 1080 | AAGUCCAGCAGGUUGUAGUca |
| 708 | 474 | CUACAACCUGCUGGACUUGtt | 1081 | CAAGUCCAGCAGGUUGUAGtc |
| 709 | 475 | UACAACCUGCUGGACUUGCtt | 1082 | GCAAGUCCAGCAGGUUGUAgt |
| 710 | 476 | ACAACCUGCUGGACUUGCUtt | 1083 | AGCAAGUCCAGCAGGUUGUag |
| 711 | 477 | CAACCUGCUGGACUUGCUGtt | 1084 | CAGCAAGUCCAGCAGGUUGta |
| 712 | 478 | AACCUGCUGGACUUGCUGCtt | 1085 | GCAGCAAGUCCAGCAGGUUgt |
| 713 | 479 | ACCUGCUGGACUUGCUGCUtt | 1086 | AGCAGCAAGUCCAGCAGGUtg |
| 714 | 480 | CCUGCUGGACUUGCUGCUGtt | 1087 | CAGCAGCAAGUCCAGCAGGtt |
| 715 | 481 | CUGCUGGACUUGCUGCUGAtt | 1088 | UCAGCAGCAAGUCCAGCAGgt |
| 716 | 482 | UGCUGGACUUGCUGCUGAUtt | 1089 | AUCAGCAGCAAGUCCAGCAgg |
| 717 | 483 | GCUGGACUUGCUGCUGAUCtt | 1090 | GAUCAGCAGCAAGUCCAGCag |
| 718 | 484 | CUGGACUUGCUGCUGAUCCtt | 1091 | GGAUCAGCAGCAAGUCCAGca |
| 719 | 485 | UGGACUUGCUGCUGAUCCAtt | 1092 | UGGAUCAGCAGCAAGUCCAgc |
| 720 | 486 | GGACUUGCUGCUGAUCCAUtt | 1093 | AUGGAUCAGCAGCAAGUCCag |
| 721 | 487 | GACUUGCUGCUGAUCCAUGtt | 1094 | CAUGGAUCAGCAGCAAGUCca |
| 722 | 488 | ACUUGCUGCUGAUCCAUGAtt | 1095 | UCAUGGAUCAGCAGCAAGUcc |
| 723 | 489 | CUUGCUGCUGAUCCAUGAGtt | 1096 | CUCAUGGAUCAGCAGCAAGtc |
| 724 | 490 | UUGCUGCUGAUCCAUGAGGtt | 1097 | CCUCAUGGAUCAGCAGCAAgt |
| 725 | 491 | UGCUGCUGAUCCAUGAGGUtt | 1098 | ACCUCAUGGAUCAGCAGCAag |
| 726 | 492 | GCUGCUGAUCCAUGAGGUCtt | 1099 | GACCUCAUGGAUCAGCAGCaa |
| 727 | 493 | CUGCUGAUCCAUGAGGUCCtt | 1100 | GGACCUCAUGGAUCAGCAGca |
| 728 | 494 | UGCUGAUCCAUGAGGUCCUtt | 1101 | AGGACCUCAUGGAUCAGCAgc |
| 729 | 495 | GCUGAUCCAUGAGGUCCUAtt | 1102 | UAGGACCUCAUGGAUCAGCag |
| 730 | 496 | CUGAUCCAUGAGGUCCUAGtt | 1103 | CUAGGACCUCAUGGAUCAGca |
| 731 | 497 | UGAUCCAUGAGGUCCUAGCtt | 1104 | GCUAGGACCUCAUGGAUCAgc |
| 732 | 498 | GAUCCAUGAGGUCCUAGCCtt | 1105 | GGCUAGGACCUCAUGGAUCag |
| 733 | 499 | AUCCAUGAGGUCCUAGCCCtt | 1106 | GGGCUAGGACCUCAUGGAUca |
| 750 | 500 | CCCUGGCUGCCUGGAUGCGtt | 1107 | CGCAUCCAGGCAGCCAGGGgc |
| 751 | 501 | CCUGGCUGCCUGGAUGCGUtt | 1108 | ACGCAUCCAGGCAGCCAGGgg |
| 752 | 502 | CUGGCUGCCUGGAUGCGUUtt | 1109 | AACGCAUCCAGGCAGCCAGgg |
| 753 | 503 | UGGCUGCCUGGAUGCGUUCtt | 1110 | GAACGCAUCCAGGCAGCCAgg |
| 754 | 504 | GGCUGCCUGGAUGCGUUCCtt | 1111 | GGAACGCAUCCAGGCAGCCag |
| 755 | 505 | GCUGCCUGGAUGCGUUCCCtt | 1112 | GGGAACGCAUCCAGGCAGCca |
| 773 | 506 | CCCUGCUCUCAGCAUAUGUtt | 1113 | ACAUAUGCUGAGAGCAGGGgg |
| 774 | 507 | CCUGCUCUCAGCAUAUGUGtt | 1114 | CACAUAUGCUGAGAGCAGGgg |

TABLE 1-continued

RNAi molecule sequences for GST-7c

| Ref Pos | SEQ ID NO | SENSE STRAND (5'-->3') SEQ ID NOS: 2 to 608 | SEQ ID NO | ANTISENSE STRAND (5'-->3') SEQ ID NOS: 609 to 1215 |
|---|---|---|---|---|
| 775 | 508 | CUGCUCUCAGCAUAUGUGGtt | 1115 | CCACAUAUGCUGAGAGCAGgg |
| 776 | 509 | UGCUCUCAGCAUAUGUGGGtt | 1116 | CCCACAUAUGCUGAGAGCAgg |
| 793 | 510 | GGGCGCCUCAGUGCCCGGCtt | 1117 | GCCGGGCACUGAGGCGCCCca |
| 794 | 511 | GGCGCCUCAGUGCCCGGCCtt | 1118 | GGCCGGGCACUGAGGCGCCcc |
| 795 | 512 | GCGCCUCAGUGCCCGGCCCtt | 1119 | GGGCCGGGCACUGAGGCGCcc |
| 796 | 513 | CGCCUCAGUGCCCGGCCCAtt | 1120 | UGGGCCGGGCACUGAGGCGcc |
| 797 | 514 | GCCUCAGUGCCCGGCCCAAtt | 1121 | UUGGGCCGGGCACUGAGGCgc |
| 798 | 515 | CCUCAGUGCCCGGCCCAAGtt | 1122 | CUUGGGCCGGGCACUGAGGcg |
| 799 | 516 | CUCAGUGCCCGGCCCAAGCtt | 1123 | GCUUGGGCCGGGCACUGAGgc |
| 800 | 517 | UCAGUGCCCGGCCCAAGCUtt | 1124 | AGCUUGGGCCGGGCACUGAgg |
| 801 | 518 | CAGUGCCCGGCCCAAGCUCtt | 1125 | GAGCUUGGGCCGGGCACUGag |
| 802 | 519 | AGUGCCCGGCCCAAGCUCAtt | 1126 | UGAGCUUGGGCCGGGCACUga |
| 803 | 520 | GUGCCCGGCCCAAGCUCAAtt | 1127 | UUGAGCUUGGGCCGGGCACtg |
| 804 | 521 | UGCCCGGCCCAAGCUCAAGtt | 1128 | CUUGAGCUUGGGCCGGGCAct |
| 805 | 522 | GCCCGGCCCAAGCUCAAGGtt | 1129 | CCUUGAGCUUGGGCCGGGCac |
| 806 | 523 | CCCGGCCCAAGCUCAAGGCtt | 1130 | GCCUUGAGCUUGGGCCGGGca |
| 807 | 524 | CCGGCCCAAGCUCAAGGCCtt | 1131 | GGCCUUGAGCUUGGGCCGGgc |
| 808 | 525 | CGGCCCAAGCUCAAGGCCUtt | 1132 | AGGCCUUGAGCUUGGGCCGgg |
| 809 | 526 | GGCCCAAGCUCAAGGCCUUtt | 1133 | AAGGCCUUGAGCUUGGGCCgg |
| 810 | 527 | GCCCAAGCUCAAGGCCUUCtt | 1134 | GAAGGCCUUGAGCUUGGGCcg |
| 811 | 528 | CCCAAGCUCAAGGCCUUCCtt | 1135 | GGAAGGCCUUGAGCUUGGGcc |
| 812 | 529 | CCAAGCUCAAGGCCUUCCUtt | 1136 | AGGAAGGCCUUGAGCUUGGgc |
| 813 | 530 | CAAGCUCAAGGCCUUCCUGtt | 1137 | CAGGAAGGCCUUGAGCUUGgg |
| 814 | 531 | AAGCUCAAGGCCUUCCUGGtt | 1138 | CCAGGAAGGCCUUGAGCUUgg |
| 815 | 532 | AGCUCAAGGCCUUCCUGGCtt | 1139 | GCCAGGAAGGCCUUGAGCUtg |
| 816 | 533 | GCUCAAGGCCUUCCUGGCCtt | 1140 | GGCCAGGAAGGCCUUGAGCtt |
| 817 | 534 | CUCAAGGCCUUCCUGGCCUtt | 1141 | AGGCCAGGAAGGCCUUGAGct |
| 818 | 535 | UCAAGGCCUUCCUGGCCUCtt | 1142 | GAGGCCAGGAAGGCCUUGAgc |
| 819 | 536 | CAAGGCCUUCCUGGCCUCCtt | 1143 | GGAGGCCAGGAAGGCCUUGag |
| 820 | 537 | AAGGCCUUCCUGGCCUCCCtt | 1144 | GGGAGGCCAGGAAGGCCUUga |
| 837 | 538 | CCCUGAGUACGUGAACCUCtt | 1145 | GAGGUUCACGUACUCAGGGga |
| 838 | 539 | CCUGAGUACGUGAACCUCCtt | 1146 | GGAGGUUCACGUACUCAGGgg |
| 839 | 540 | CUGAGUACGUGAACCUCCCtt | 1147 | GGGAGGUUCACGUACUCAGgg |
| 856 | 541 | CCCAUCAAUGGCAACGGGAtt | 1148 | UCCCGUUGCCAUUGAUGGGga |
| 857 | 542 | CCAUCAAUGGCAACGGGAAtt | 1149 | UUCCCGUUGCCAUUGAUGGgg |
| 858 | 543 | CAUCAAUGGCAACGGGAAAtt | 1150 | UUUCCCGUUGCCAUUGAUGgg |
| 859 | 544 | AUCAAUGGCAACGGGAAACtt | 1151 | GUUUCCCGUUGCCAUUGAUgg |

TABLE 1-continued

RNAi molecule sequences for GST-7c

| Ref Pos | SEQ ID NO | SENSE STRAND (5'-->3') SEQ ID NOS: 2 to 608 | SEQ ID NO | ANTISENSE STRAND (5'-->3') SEQ ID NOS: 609 to 1215 |
|---|---|---|---|---|
| 860 | 545 | UCAAUGGCAACGGGAAACAtt | 1152 | UGUUUCCCGUUGCCAUUGAtg |
| 861 | 546 | CAAUGGCAACGGGAAACAGtt | 1153 | CUGUUUCCCGUUGCCAUUGat |
| 862 | 547 | AAUGGCAACGGGAAACAGUtt | 1154 | ACUGUUUCCCGUUGCCAUUga |
| 863 | 548 | AUGGCAACGGGAAACAGUGtt | 1155 | CACUGUUUCCCGUUGCCAUtg |
| 864 | 549 | UGGCAACGGGAAACAGUGAtt | 1156 | UCACUGUUUCCCGUUGCCAtt |
| 865 | 550 | GGCAACGGGAAACAGUGAGtt | 1157 | CUCACUGUUUCCCGUUGCcat |
| 866 | 551 | GCAACGGGAAACAGUGAGGtt | 1158 | CCUCACUGUUUCCCGUUGCca |
| 867 | 552 | CAACGGGAAACAGUGAGGGtt | 1159 | CCCUCACUGUUUCCCGUUGcc |
| 868 | 553 | AACGGGAAACAGUGAGGGUtt | 1160 | ACCCUCACUGUUUCCCGUUgc |
| 869 | 554 | ACGGGAAACAGUGAGGGUUtt | 1161 | AACCCUCACUGUUUCCCGUUtg |
| 870 | 555 | CGGGAAACAGUGAGGGUUGtt | 1162 | CAACCCUCACUGUUUCCCGtt |
| 871 | 556 | GGGAAACAGUGAGGGUUGGtt | 1163 | CCAACCCUCACUGUUUCCCgt |
| 872 | 557 | GGAAACAGUGAGGGUUGGGtt | 1164 | CCCAACCCUCACUGUUUCCcg |
| 891 | 558 | GGGACUCUGAGCGGGAGGCtt | 1165 | GCCUCCCGCUCAGAGUCCCcc |
| 892 | 559 | GGACUCUGAGCGGGAGGCAtt | 1166 | UGCCUCCCGCUCAGAGUCCcc |
| 894 | 560 | ACUCUGAGCGGGAGGCAGAtt | 1167 | UCUGCCUCCCGCUCAGAGUcc |
| 896 | 561 | UCUGAGCGGGAGGCAGAGUtt | 1168 | ACUCUGCCUCCCGCUCAGAgt |
| 897 | 562 | CUGAGCGGGAGGCAGAGUUtt | 1169 | AACUCUGCCUCCCGCUCAGag |
| 898 | 563 | UGAGCGGGAGGCAGAGUUUtt | 1170 | AAACUCUGCCUCCCGCUCAga |
| 899 | 564 | GAGCGGGAGGCAGAGUUUGtt | 1171 | CAAACUCUGCCUCCCGCUCag |
| 900 | 565 | AGCGGGAGGCAGAGUUUGCtt | 1172 | GCAAACUCUGCCUCCCGCUca |
| 901 | 566 | GCGGGAGGCAGAGUUUGCCtt | 1173 | GGCAAACUCUGCCUCCCGCtc |
| 902 | 567 | CGGGAGGCAGAGUUUGCCUtt | 1174 | AGGCAAACUCUGCCUCCCGct |
| 903 | 568 | GGGAGGCAGAGUUUGCCUUtt | 1175 | AAGGCAAACUCUGCCUCCCgc |
| 904 | 569 | GGAGGCAGAGUUUGCCUUCtt | 1176 | GAAGGCAAACUCUGCCUCCcg |
| 905 | 570 | GAGGCAGAGUUUGCCUUCCtt | 1177 | GGAAGGCAAACUCUGCCUCcc |
| 906 | 571 | AGGCAGAGUUUGCCUUCCUtt | 1178 | AGGAAGGCAAACUCUGCCUcc |
| 907 | 572 | GGCAGAGUUUGCCUUCCUUtt | 1179 | AAGGAAGGCAAACUCUGCCtc |
| 908 | 573 | GCAGAGUUUGCCUUCCUUUtt | 1180 | AAAGGAAGGCAAACUCUGCct |
| 909 | 574 | CAGAGUUUGCCUUCCUUUCtt | 1181 | GAAAGGAAGGCAAACUCUGcc |
| 910 | 575 | AGAGUUUGCCUUCCUUUCUtt | 1182 | AGAAAGGAAGGCAAACUCUgc |
| 911 | 576 | GAGUUUGCCUUCCUUUCUCtt | 1183 | GAGAAAGGAAGGCAAACUCtg |
| 912 | 577 | AGUUUGCCUUCCUUUCUCCtt | 1184 | GGAGAAAGGAAGGCAAACUct |
| 913 | 578 | GUUUGCCUUCCUUUCUCCAtt | 1185 | UGGAGAAAGGAAGGCAAACtc |
| 914 | 579 | UUUGCCUUCCUUUCUCCAGtt | 1186 | CUGGAGAAAGGAAGGCAAAct |
| 915 | 580 | UUGCCUUCCUUUCUCCAGGtt | 1187 | CCUGGAGAAAGGAAGGCAAac |
| 916 | 581 | UGCCUUCCUUUCUCCAGGAtt | 1188 | UCCUGGAGAAAGGAAGGCAaa |

TABLE 1-continued

RNAi molecule sequences for GST-7c

| Ref Pos | SEQ ID NO | SENSE STRAND (5'-->3') SEQ ID NOS: 2 to 608 | SEQ ID NO | ANTISENSE STRAND (5'-->3') SEQ ID NOS: 609 to 1215 |
|---|---|---|---|---|
| 917 | 582 | GCCUUCCUUUCUCCAGGACUtt | 1189 | GUCCUGGAGAAAGGAAGGCaa |
| 918 | 583 | CCUUCCUUUCUCCAGGACCtt | 1190 | GGUCCUGGAGAAAGGAAGGca |
| 919 | 584 | CUUCCUUUCUCCAGGACCAtt | 1191 | UGGUCCUGGAGAAAGGAAGgc |
| 920 | 585 | UUCCUUUCUCCAGGACCAAtt | 1192 | UUGGUCCUGGAGAAAGGAAgg |
| 921 | 586 | UCCUUUCUCCAGGACCAAUtt | 1193 | AUUGGUCCUGGAGAAAGGAag |
| 922 | 587 | CCUUUCUCCAGGACCAAUAtt | 1194 | UAUUGGUCCUGGAGAAAGGaa |
| 923 | 588 | CUUUCUCCAGGACCAAUAAtt | 1195 | UUAUUGGUCCUGGAGAAAGga |
| 924 | 589 | UUUCUCCAGGACCAAUAAAtt | 1196 | UUUAUUGGUCCUGGAGAAAgg |
| 925 | 590 | UUCUCCAGGACCAAUAAAAtt | 1197 | UUUUAUUGGUCCUGGAGAAag |
| 926 | 591 | UCUCCAGGACCAAUAAAAUtt | 1198 | AUUUUAUUGGUCCUGGAGAaa |
| 927 | 592 | CUCCAGGACCAAUAAAAUUtt | 1199 | AAUUUUAUUGGUCCUGGAGaa |
| 928 | 593 | UCCAGGACCAAUAAAAUUUtt | 1200 | AAAUUUUAUUGGUCCUGGAga |
| 929 | 594 | CCAGGACCAAUAAAAUUUCtt | 1201 | GAAAUUUUAUUGGUCCUGGag |
| 930 | 595 | CAGGACCAAUAAAAUUUCUtt | 1202 | AGAAAUUUUAUUGGUCCUGga |
| 931 | 596 | AGGACCAAUAAAAUUUCUAtt | 1203 | UAGAAAUUUUAUUGGUCCUgg |
| 932 | 597 | GGACCAAUAAAAUUUCUAAtt | 1204 | UUAGAAAUUUUAUUGGUCCtg |
| 933 | 598 | GACCAAUAAAAUUUCUAAGtt | 1205 | CUUAGAAAUUUUAUUGGUCct |
| 934 | 599 | ACCAAUAAAAUUUCUAAGAtt | 1206 | UCUUAGAAAUUUUAUUGGUcc |
| 935 | 600 | CCAAUAAAAUUUCUAAGAGtt | 1207 | CUCUUAGAAAUUUUAUUGGtc |
| 936 | 601 | CAAUAAAAUUUCUAAGAGAtt | 1208 | UCUCUUAGAAAUUUUAUUGgt |
| 937 | 602 | AAUAAAAUUUCUAAGAGAGtt | 1209 | CUCUCUUAGAAAUUUUAUUgg |
| 938 | 603 | AUAAAAUUUCUAAGAGAGCtt | 1210 | GCUCUCUUAGAAAUUUUAUtg |
| 939 | 604 | UAAAAUUUCUAAGAGAGCUtt | 1211 | AGCUCUCUUAGAAAUUUUAtt |
| 940 | 605 | AAAAUUUCUAAGAGAGCUAtt | 1212 | UAGCUCUCUUAGAAAUUUUat |
| 941 | 606 | AAAUUUCUAAGAGAGCUAAtt | 1213 | UUAGCUCUCUUAGAAAUUUta |
| 942 | 607 | AAUUUCUAAGAGAGCUAAAtt | 1214 | UUUAGCUCUCUUAGAAAUUtt |
| 943 | 608 | AUUUCUAAGAGAGCUAAAAtt | 1215 | UUUUAGCUCUCUUAGAAAUtt |

Key for Table 1: Upper case A, G, C and U referred to for ribo-A, ribo-G, ribo-C and ribo-U respectively. The lower case letters a, g, c, t represent 2'-deoxy-A, 2'-deoxy-G, 2'-deoxy-C and thymidine respectively.

TABLE 2

RNAi molecule sequences for GST-7c

| ID | Ref Pos | SEQ ID NO | SENSE STRAND (5'-->3') SEQ ID NOS: 1216 to 1280 | SEQ ID NO | ANTISENSE STRAND (5'-->3') SEQ ID NOS: 1281 to 1345 |
|---|---|---|---|---|---|
| A1 | 652 | 1216 | UCCCAGAACCAGGGAGGCAtt | 1281 | UGCCUCCCUGGUUCUGGGAca |
| A10 | 635 | 1217 | CUUUUGAGACCCUGCUGUCtt | 1282 | GACAGCAGGGUCUCAAAAGgc |
| A11 | 649 | 1218 | CUGUCCCAGAACCAGGGAGtt | 1283 | CUCCCUGGUUCUGGGACAGca |

TABLE 2-continued

RNAi molecule sequences for GST-7c

| ID | Ref Pos | SEQ ID NO SEQ ID NOS: 1216 to 1280 | SENSE STRAND (5'-->3') | SEQ ID NO SEQ ID NOS: 1281 to 1345 | ANTISENSE STRAND (5'-->3') |
|---|---|---|---|---|---|
| A12 | 650 | 1219 | UGUCCCAGAACCAGGGAGGtt | 1284 | CCUCCCUGGUUCUGGGACAgc |
| A13 | 631 | 1220 | AAGCCUUUUGAGACCCUGCtt | 1285 | GCAGGGUCUCAAAAGGCUUca |
| A14 | 638 | 1221 | UUGAGACCCUGCUGUCCCAtt | 1286 | UGGGACAGCAGGGUCUCAAaa |
| A15 | 636 | 1222 | UUUUGAGACCCUGCUGUCCtt | 1287 | GGACAGCAGGGUCUCAAAAgg |
| A16 | 640 | 1223 | GAGACCCUGCUGUCCCAGAtt | 1288 | UCUGGGACAGCAGGGUCUCaa |
| A17 | 332 | 1224 | GCUGGAAGGAGGAGGUGGUtt | 1289 | ACCACCUCCUCCUUCCAGCtc |
| A18 | 333 | 1225 | CUGGAAGGAGGAGGUGGUGtt | 1290 | CACCACCUCCUCCUUCCAGct |
| A19 | 321 | 1226 | UCAGGGCCAGAGCUGGAAGtt | 1291 | CUUCCAGCUCUGGCCCUGAtc |
| A2 | 639 | 1227 | UGAGACCCUGCUGUCCCAGtt | 1292 | CUGGGACAGCAGGGUCUCAaa |
| A20 | 323 | 1228 | AGGGCCAGAGCUGGAAGGAtt | 1293 | UCCUUCCAGCUCUGGCCCUga |
| A21 | 331 | 1229 | AGCUGGAAGGAGGAGGUGGtt | 1294 | CCACCUCCUCCUUCCAGCUct |
| A22 | 641 | 1230 | AGACCCUGCUGUCCCAGAAtt | 1295 | UUCUGGGACAGCAGGGUCUca |
| A23 | 330 | 1231 | GAGCUGGAAGGAGGAGGUGtt | 1296 | CACCUCCUCCUUCCAGCUCtg |
| A25 | 647 | 1232 | UGCUGUCCCAGAACCAGGGtt | 1297 | CCCUGGUUCUGGGACAGCAgg |
| A26 | 653 | 1233 | CCCAGAACCAGGGAGGCAAtt | 1298 | UUGCCUCCCUGGUUCUGGGac |
| A3 | 654 | 1234 | CCAGAACCAGGGAGGCAAGtt | 1299 | CUUGCCUCCCUGGUUCUGGga |
| A4 | 637 | 1235 | UUUGAGACCCUGCUGUCCCtt | 1300 | GGGACAGCAGGGUCUCAAAag |
| AS | 642 | 1236 | GACCCUGCUGUCCCAGAACtt | 1301 | GUUCUGGGACAGCAGGGUCtc |
| A6 | 319 | 1237 | GAUCAGGGCCAGAGCUGGAtt | 1302 | UCCAGCUCUGGCCCUGAUCtg |
| A7 | 632 | 1238 | AGCCUUUUGAGACCCUGCUtt | 1303 | AGCAGGGUCUCAAAAGGCUtc |
| A8 | 633 | 1239 | GCCUUUUGAGACCCUGCUGtt | 1304 | CAGCAGGGUCUCAAAAGGCtt |
| A9 | 634 | 1240 | CCUUUUGAGACCCUGCUGUtt | 1305 | ACAGCAGGGUCUCAAAAGGct |
| AG7 | 632 | 1241 | CGCCUUUUGAGACCCUGCAtt | 1306 | UGCAGGGUCUCAAAAGGCGtc |
| AK1 | 257 | 1242 | CCUACACCGUGGUCUAUUUtt | 1307 | AAAUAGACCACGGUGUAGGgc |
| AK10 | 681 | 1243 | UGUGGGAGACCAGAUCUCCtt | 1308 | GGAGAUCUGGUCUCCCACAat |
| AK11 | 901 | 1244 | GCGGGAGGCAGAGUUUGCCtt | 1309 | GGCAAACUCUGCCUCCCGCtc |
| AK12 | 922 | 1245 | CCUUUCUCCAGGACCAAUAtt | 1310 | UAUUGGUCCUGGAGAAAGGaa |
| AK13/A24 | 643 | 1246 | ACCCUGCUGUCCCAGAACCtt | 1311 | GGUUCUGGGACAGCAGGGUct |
| AK2 | 267 | 1247 | GGUCUAUUUCCCAGUUCGAtt | 1312 | UCGAACUGGGAAAUAGACCac |
| AK3 | 512 | 1248 | CCCUGGUGGACAUGGUGAAtt | 1313 | UUCACCAUGUCCACCAGGGct |
| AK4 | 560 | 1249 | ACAUCUCCCUCAUCUACACtt | 1314 | GUGUAGAUGAGGGAGAUGUat |
| AK5 | 593 | 1250 | GCAAGGAUGACUAUGUGAAtt | 1315 | UUCACAUAGUCAUCCUUGCcc |
| AK6 | 698 | 1251 | CCUUCGCUGACUACAACCUtt | 1316 | AGGUUGUAGUCAGCGAAGGag |
| AK7 | 313 | 1252 | CUGGCAGAUCAGGGCCAGAtt | 1317 | UCUGGCCCUGAUCUGCCAGca |
| AK8 | 421 | 1253 | GACGGAGACCUCACCCUGUtt | 1318 | ACAGGGUGAGGUCUCCGUCct |
| AK9 | 590 | 1254 | CGGGCAAGGAUGACUAUGUtt | 1319 | ACAUAGUCAUCCUUGCCCGcc |

TABLE 2-continued

RNAi molecule sequences for GST-7c

| ID | Ref Pos | SEQ ID NO SEQ ID NOS: 1216 to 1280 | SENSE STRAND (5'-->3') | SEQ ID NO SEQ ID NOS: 1281 to 1345 | ANTISENSE STRAND (5'-->3') |
|---|---|---|---|---|---|
| AU10 | 635 | 1255 | CUUUUGAGACCCUGCUGUAtt | 1320 | UACAGCAGGGUCUCAAAAGgc |
| AU23 | 330 | 1256 | GAGCUGGAAGGAGGAGGUAtt | 1321 | UACCUCCUCCUUCCAGCUCtg |
| AU24 | 643 | 1257 | ACCCUGCUGUCCCAGAACAtt | 1322 | UGUUCUGGGACAGCAGGGUct |
| AU25 | 648 | 1258 | UGCUGUCCCAGAACCAGGAtt | 1323 | UCCUGGUUCUGGGACAGCAgg |
| AU7 | 632 | 1259 | AGCCUUUUGAGACCCUGCAtt | 1324 | UGCAGGGUCUCAAAAGGCUtc |
| AU9 | 634 | 1260 | CCUUUUGAGACCCUGCUGAtt | 1325 | UCAGCAGGGUCUCAAAAGGct |
| B1 | 629 | 1261 | UGAAGCCUUUUGAGACCCUtt | 1326 | AGGGUCUCAAAAGGCUUCAgt |
| B10 | 627 | 1262 | ACUGAAGCCUUUUGAGACCtt | 1327 | GGUCUCAAAAGGCUUCAGUtg |
| B11 | 596 | 1263 | AGGAUGACUAUGUGAAGGCtt | 1328 | GCCUUCACAUAGUCAUCCUtg |
| B12 | 597 | 1264 | GGAUGACUAUGUGAAGGCAtt | 1329 | UGCCUUCACAUAGUCAUCCtt |
| B13 | 598 | 1265 | GAUGACUAUGUGAAGGCACtt | 1330 | GUGCCUUCACAUAGUCAUCct |
| B14 | 564 | 1266 | CUCCCUCAUCUACACCAACtt | 1331 | GUUGGUGUAGAUGAGGGAGat |
| B2 | 630 | 1267 | GAAGCCUUUUGAGACCCUGtt | 1332 | CAGGGUCUCAAAAGGCUUCag |
| B3 | 563 | 1268 | UCUCCCUCAUCUACACCAAtt | 1333 | UUGGUGUAGAUGAGGGAGAtg |
| B4 | 567 | 1269 | CCUCAUCUACACCAACUAUtt | 1334 | AUAGUUGGUGUAGAUGAGGga |
| B5 | 566 | 1270 | CCCUCAUCUACACCAACUAtt | 1335 | UAGUUGGUGUAGAUGAGGGag |
| B6 | 625 | 1271 | CAACUGAAGCCUUUUGAGAtt | 1336 | UCUCAAAAGGCUUCAGUUGcc |
| B7 | 626 | 1272 | AACUGAAGCCUUUUGAGACtt | 1337 | GUCUCAAAAGGCUUCAGUUgc |
| B8 | 628 | 1273 | CUGAAGCCUUUUGAGACCCtt | 1338 | GGGUCUCAAAAGGCUUCAGtt |
| B9 | 565 | 1274 | UCCCUCAUCUACACCAACUtt | 1339 | AGUUGGUGUAGAUGAGGGAga |
| BG3 | 563 | 1275 | GCUCCCUCAUCUACACCAAtt | 1340 | UUGGUGUAGAUGAGGGAGCtg |
| BU02 | 631 | 1276 | GAAGCCUUUUGAGACCCUAtt | 1341 | UAGGGUCUCAAAAGGCUUCag |
| BU10 | 627 | 1277 | ACUGAAGCCUUUUGAGACAtt | 1342 | UGUCUCAAAAGGCUUCAGUtg |
| BU14 | 565 | 1278 | CUCCCUCAUCUACACCAAAtt | 1343 | UUUGGUGUAGAUGAGGGAGat |
| BU4 | 567 | 1279 | CCUCAUCUACACCAACUAAtt | 1344 | UUAGUUGGUGUAGAUGAGGga |
| C1-934 | 934 | 1280 | ACCAAUAAAAUUUCUAAGAtt | 1345 | UCUUAGAAAUUUUAUUGGUcc |

Key for Table 2: Upper case A, G, C and U referred to for ribo-A, ribo-G, ribo-C and ribo-U respectively. The lower case letters a, g, c, t represent 2'-deoxy-A, 2'-deoxy-G, 2'-deoxy-C and thymidine respectively.

For example, a siRNA of this invention may have an antisense strand which is SEQ ID NO:1341, and a sense strand which is SEQ ID NO:1276, or chemically modified strands thereof.

For example, a siRNA of this invention may have an antisense strand which is SEQ ID NO:1305, and a sense strand which is SEQ ID NO:1240, or chemically modified strands thereof.

Chemical modifications may comprise a 2'-OMe substituent group on any nucleotide in any position in a strand, as well as other modifications known in the art.

Methods for Modulating GST-π and Treating Malignant Tumor

Embodiments of this invention can provide RNAi molecules that can be used to down regulate or inhibit the expression of GST-π and/or GST-π proteins.

In some embodiments, a RNAi molecule of this invention can be used to down regulate or inhibit the expression of GST-π and/or GST-π proteins arising from GST-π haplotype polymorphisms that may be associated with a disease or condition such as malignant tumor.

Monitoring of GST-π protein or mRNA levels can be used to characterize gene silencing, and to determine the efficacy of compounds and compositions of this invention.

The RNAi molecules of this disclosure can be used individually, or in combination with other siRNAs for modulating the expression of one or more genes.

The RNAi molecules of this disclosure can be used individually, or in combination, or in conjunction with other known drugs for preventing or treating diseases, or ameliorating symptoms of conditions or disorders associated with GST-π, including malignant tumor.

The RNAi molecules of this invention can be used to modulate or inhibit the expression of GST-π in a sequence-specific manner.

The RNAi molecules of this disclosure can include a guide strand for which a series of contiguous nucleotides are at least partially complementary to a GST-π mRNA.

In certain aspects, malignant tumor may be treated by RNA interference using a RNAi molecule of this invention.

Treatment of malignant tumor may be characterized in suitable cell-based models, as well as ex vivo or in vivo animal models.

Treatment of malignant tumor may be characterized by determining the level of GST-π mRNA or the level of GST-π protein in cells of affected tissue.

Treatment of malignant tumor may be characterized by non-invasive medical scanning of an affected organ or tissue.

Embodiments of this invention may include methods for preventing, treating, or ameliorating the symptoms of a GST-π associated disease or condition in a subject in need thereof.

In some embodiments, methods for preventing, treating, or ameliorating the symptoms of malignant tumor in a subject can include administering to the subject a RNAi molecule of this invention to modulate the expression of a GST-π gene in the subject or organism.

In some embodiments, this invention contemplates methods for down regulating the expression of a GST-π gene in a cell or organism, by contacting the cell or organism with a RNAi molecule of this invention.

RNA Interference

RNA interference (RNAi) refers to sequence-specific post-transcriptional gene silencing in animals mediated by short interfering RNAs (siRNAs). See, e.g., Zamore et al., Cell, 2000, Vol. 101, pp. 25-33; Fire et al., Nature, 1998, Vol. 391, pp. 806811; Sharp, Genes & Development, 1999, Vol. 13, pp. 139-141.

An RNAi response in cells can be triggered by a double stranded RNA (dsRNA), although the mechanism is not yet fully understood. Certain dsRNAs in cells can undergo the action of Dicer enzyme, a ribonuclease III enzyme. See, e.g., Zamore et al., Cell, 2000, Vol. 101, pp. 25-33; Hammond et al., Nature, 2000, Vol. 404, pp. 293-296. Dicer can process the dsRNA into shorter pieces of dsRNA, which are siRNAs.

In general, siRNAs can be from about 21 to about 23 nucleotides in length and include a base pair duplex region about 19 nucleotides in length.

RNAi involves an endonuclease complex known as the RNA induced silencing complex (RISC). An siRNA has an antisense or guide strand which enters the RISC complex and mediates cleavage of a single stranded RNA target having a sequence complementary to the antisense strand of the siRNA duplex. The other strand of the siRNA is the passenger strand. Cleavage of the target RNA takes place in the middle of the region complementary to the antisense strand of the siRNA duplex See, e.g., Elbashir et al., Genes & Development, 2001, Vol. 15, pp. 188-200.

As used herein, the term "sense strand" refers to a nucleotide sequence of a siRNA molecule that is partially or fully complementary to at least a portion of a corresponding antisense strand of the siRNA molecule. The sense strand of a siRNA molecule can include a nucleic acid sequence having homology with a target nucleic acid sequence.

As used herein, the term "antisense strand" refers to a nucleotide sequence of a siRNA molecule that is partially or fully complementary to at least a portion of a target nucleic acid sequence. The antisense strand of a siRNA molecule can include a nucleic acid sequence that is complementary to at least a portion of a corresponding sense strand of the siRNA molecule.

RNAi molecules can down regulate or knock down gene expression by mediating RNA interference in a sequence-specific manner. See, e.g., Zamore et al., Cell, 2000, Vol. 101, pp. 25-33; Elbashir et al., Nature, 2001, Vol. 411, pp. 494-498; Kreutzer et al., WO2000/044895; Zernicka-Goetz et al., WO2001/36646; Fire et al., WO1999/032619; Plaetinck et al., WO2000/01846; Mello et al., WO2001/029058.

As used herein, the terms "inhibit," "down-regulate," or "reduce" with respect to gene expression means that the expression of the gene, or the level of mRNA molecules encoding one or more proteins, or the activity of one or more of the encoded proteins is reduced below that observed in the absence of a RNAi molecule or siRNA of this invention. For example, the level of expression, level of mRNA, or level of encoded protein activity may be reduced by at least 1%, or at least 10%, or at least 20%, or at least 50%, or at least 90%, or more from that observed in the absence of a RNAi molecule or siRNA of this invention.

RNAi molecules can also be used to knock down viral gene expression, and therefore affect viral replication.

RNAi molecules can be made from separate polynucleotide strands: a sense strand or passenger strand, and an antisense strand or guide strand. The guide and passenger strands are at least partially complementary. The guide strand and passenger strand can form a duplex region having from about 15 to about 49 base pairs.

In some embodiments, the duplex region of a siRNA can have 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 base pairs.

In certain embodiments, a RNAi molecule can be active in a RISC complex, with a length of duplex region active for RISC.

In additional embodiments, a RNAi molecule can be active as a Dicer substrate, to be converted to a RNAi molecule that can be active in a RISC complex.

In some aspects, a RNAi molecule can have complementary guide and passenger sequence portions at opposing ends of a long molecule, so that the molecule can form a duplex region with the complementary sequence portions, and the strands are linked at one end of the duplex region by either nucleotide or non-nucleotide linkers. For example, a hairpin arrangement, or a stem and loop arrangement. The linker interactions with the strands can be covalent bonds or non-covalent interactions.

A RNAi molecule of this disclosure may include a nucleotide, non-nucleotide, or mixed nucleotide/non-nucleotide linker that joins the sense region of the nucleic acid to the antisense region of the nucleic acid. A nucleotide linker can be a linker of ≥2 nucleotides in length, for example about 3, 4, 5, 6, 7, 8, 9, or 10 nucleotides in length. The nucleotide linker can be a nucleic acid aptamer. By "aptamer" or "nucleic acid aptamer" as used herein refers to a nucleic acid molecule that binds specifically to a target molecule wherein the nucleic acid molecule has sequence that includes a sequence recognized by the target molecule in its natural setting. Alternately, an aptamer can be a nucleic acid molecule that binds to a target molecule, where the target molecule does not naturally bind to a nucleic acid. For example, the aptamer can be used to bind to a ligand-binding domain of a protein, thereby preventing interaction of the naturally occurring ligand with the protein. See, e.g., Gold et al., Annu Rev Biochem, 1995, Vol. 64, pp. 763-797; Brody et al., J. Biotechnol., 2000, Vol. 74, pp. 5-13; Hermann et al., Science, 2000, Vol. 287, pp. 820-825.

Examples of a non-nucleotide linker include an abasic nucleotide, polyether, polyamine, polyamide, peptide, carbohydrate, lipid, polyhydrocarbon, or other polymeric compounds, for example polyethylene glycols such as those having from 2 to 100 ethylene glycol units. Some examples are described in Seela et al., Nucleic Acids Research, 1987, Vol. 15, pp. 3113-3129; Cload et al., J. Am. Chem. Soc., 1991, Vol. 113, pp. 6324-6326; Jaeschke et al., Tetrahedron Lett., 1993, Vol. 34, pp. 301; Arnold et al., WO1989/002439; Usman et al., WO1995/006731; Dudycz et al., WO1995/011910, and Ferentz et al., J. Am. Chem. Soc., 1991, Vol. 113, pp. 4000-4002.

A RNAi molecule can have one or more overhangs from the duplex region. The overhangs, which are non-base-paired, single strand regions, can be from one to eight nucleotides in length, or longer. An overhang can be a 3'-end overhang, wherein the 3'-end of a strand has a single strand region of from one to eight nucleotides. An overhang can be a 5'-end overhang, wherein the 5'-end of a strand has a single strand region of from one to eight nucleotides.

The overhangs of a RNAi molecule can have the same length, or can be different lengths.

A RNAi molecule can have one or more blunt ends, in which the duplex region ends with no overhang, and the strands are base paired to the end of the duplex region.

A RNAi molecule of this disclosure can have one or more blunt ends, or can have one or more overhangs, or can have a combination of a blunt end and an overhang end.

A 5'-end of a strand of a RNAi molecule may be in a blunt end, or can be in an overhang. A 3'-end of a strand of a RNAi molecule may be in a blunt end, or can be in an overhang.

A 5'-end of a strand of a RNAi molecule may be in a blunt end, while the 3'-end is in an overhang. A 3'-end of a strand of a RNAi molecule may be in a blunt end, while the 5'-end is in an overhang.

In some embodiments, both ends of a RNAi molecule are blunt ends.

In additional embodiments, both ends of a RNAi molecule have an overhang.

The overhangs at the 5'- and 3'-ends may be of different lengths.

In certain embodiments, a RNAi molecule may have a blunt end where the 5'-end of the antisense strand and the 3'-end of the sense strand do not have any overhanging nucleotides.

In further embodiments, a RNAi molecule may have a blunt end where the 3'-end of the antisense strand and the 5'-end of the sense strand do not have any overhanging nucleotides.

A RNAi molecule may have mismatches in base pairing in the duplex region.

Any nucleotide in an overhang of a RNAi molecule can be a deoxyribonucleotide, or a ribonucleotide.

One or more deoxyribonucleotides may be at the 5'-end, where the 3'-end of the other strand of the RNAi molecule may not have an overhang, or may not have a deoxyribonucleotide overhang.

One or more deoxyribonucleotides may be at the 3'-end, where the 5'-end of the other strand of the RNAi molecule may not have an overhang, or may not have a deoxyribonucleotide overhang.

In some embodiments, one or more, or all of the overhang nucleotides of a RNAi molecule may be 2'-deoxyribonucleotides.

Dicer Substrate RNAi Molecules

In some aspects, a RNAi molecule can be of a length suitable as a Dicer substrate, which can be processed to produce a RISC active RNAi molecule. See, e.g., Rossi et al., US2005/0244858.

A double stranded RNA (dsRNA) that is a Dicer substrate can be of a length sufficient such that it is processed by Dicer to produce an active RNAi molecule, and may further include one or more of the following properties: (i) the Dicer substrate dsRNA can be asymmetric, for example, having a 3' overhang on the antisense strand, and (ii) the Dicer substrate dsRNA can have a modified 3' end on the sense strand to direct orientation of Dicer binding and processing of the dsRNA to an active RNAi molecule.

In certain embodiments, the longest strand in a Dicer substrate dsRNA may be 24-30 nucleotides in length.

A Dicer substrate dsRNA can be symmetric or asymmetric.

In some embodiments, a Dicer substrate dsRNA can have a sense strand of 22-28 nucleotides and an antisense strand of 24-30 nucleotides.

In certain embodiments, a Dicer substrate dsRNA may have an overhang on the 3' end of the antisense strand.

In further embodiments, a Dicer substrate dsRNA may have a sense strand 25 nucleotides in length, and an antisense strand 27 nucleotides in length, with a 2 base 3'-overhang. The overhang may be 1, 2 or 3 nucleotides in length. The sense strand may also have a 5' phosphate.

An asymmetric Dicer substrate dsRNA may have two deoxyribonucleotides at the 3'-end of the sense strand in place of two of the ribonucleotides.

The sense strand of a Dicer substrate dsRNA may be from about 22 to about 30, or from about 22 to about 28; or from about 24 to about 30; or from about 25 to about 30; or from about 26 to about 30; or from about 26 and 29; or from about 27 to about 28 nucleotides in length.

The sense strand of a Dicer substrate dsRNA may be 22, 23, 24, 25, 26, 27, 28, 29 or 30 nucleotides in length.

In certain embodiments, a Dicer substrate dsRNA may have sense and antisense strands that are at least about 25 nucleotides in length, and no longer than about 30 nucleotides in length.

In certain embodiments, a Dicer substrate dsRNA may have sense and antisense strands that are 26 to 29 nucleotides in length.

In certain embodiments, a Dicer substrate dsRNA may have sense and antisense strands that are 27 nucleotides in length.

The sense and antisense strands of a Dicer substrate dsRNA may be the same length as in being blunt ended, or different lengths as in having overhangs, or may have a blunt end and an overhang.

A Dicer substrate dsRNA may have a duplex region of 19, 20, 21, 22, 23, 24, 25, 26 or 27 nucleotides in length.

The antisense strand of a Dicer substrate dsRNA may have any sequence that anneals to at least a portion of the sequence of the sense strand under biological conditions, such as within the cytoplasm of a eukaryotic cell.

A Dicer substrate with a sense and an antisense strand can be linked by a third structure, such as a linker group or a linker oligonucleotide. The linker connects the two strands of the dsRNA, for example, so that a hairpin is formed upon annealing.

The sense and antisense strands of a Dicer substrate are in general complementary, but may have mismatches in base pairing.

In some embodiments, a Dicer substrate dsRNA can be asymmetric such that the sense strand has 22-28 nucleotides and the antisense strand has 24-30 nucleotides.

A region of one of the strands, particularly the antisense strand, of the Dicer substrate dsRNA may have a sequence length of at least 19 nucleotides, wherein these nucleotides are in the 21-nucleotide region adjacent to the 3' end of the antisense strand and are sufficiently complementary to a nucleotide sequence of the RNA produced from the target gene.

An antisense strand of a Dicer substrate dsRNA can have from 1 to 9 ribonucleotides on the 5'-end, to give a length of 22-28 nucleotides. When the antisense strand has a length of 21 nucleotides, then 1-7 ribonucleotides, or 2-5 ribonucleotides, or 4 ribonucleotides may be added on the 3'-end. The added ribonucleotides may have any sequence.

A sense strand of a Dicer substrate dsRNA may have 24-30 nucleotides. The sense strand may be substantially complementary with the antisense strand to anneal to the antisense strand under biological conditions.

Methods of Use of RNAi Molecules

The nucleic acid molecules and RNAi molecules of this invention may be delivered to a cell or tissue by direct application of the molecules, or with the molecules combined with a carrier or a diluent.

The nucleic acid molecules and RNAi molecules of this invention can be delivered or administered to a cell, tissue, organ, or subject by direct application of the molecules with a carrier or diluent, or any other delivery vehicle that acts to assist, promote or facilitate entry into a cell, for example, viral sequences, viral material, or lipid or liposome formulations.

The nucleic acid molecules and RNAi molecules of this invention can be complexed with cationic lipids, packaged within liposomes, or otherwise delivered to target cells or tissues. The nucleic acid or nucleic acid complexes can be locally administered to relevant tissues ex vivo, or in vivo through direct dermal application, transdermal application, or injection.

Delivery systems may include, for example, aqueous and nonaqueous gels, creams, emulsions, microemulsions, liposomes, ointments, aqueous and nonaqueous solutions, lotions, aerosols, hydrocarbon bases and powders, and can contain excipients such as solubilizers and permeation enhancers.

Compositions and methods of this disclosure can include an expression vector that includes a nucleic acid sequence encoding at least one RNAi molecule of this invention in a manner that allows expression of the nucleic acid molecule.

The nucleic acid molecules and RNAi molecules of this invention can be expressed from transcription units inserted into DNA or RNA vectors. Recombinant vectors can be DNA plasmids or viral vectors. Viral vectors can be used that provide for transient expression of nucleic acid molecules.

For example, the vector may contain sequences encoding both strands of a RNAi molecule of a duplex, or a single nucleic acid molecule that is self-complementary and thus forms a RNAi molecule. An expression vector may include a nucleic acid sequence encoding two or more nucleic acid molecules.

A nucleic acid molecule may be expressed within cells from eukaryotic promoters. Those skilled in the art realize that any nucleic acid can be expressed in eukaryotic cells from the appropriate DNA/RNA vector.

In some aspects, a viral construct can be used to introduce an expression construct into a cell, for transcription of a dsRNA construct encoded by the expression construct.

Lipid formulations can be administered to animals by intravenous, intramuscular, or intraperitoneal injection, or orally or by inhalation or other methods as are known in the art.

Pharmaceutically acceptable formulations for administering oligonucleotides are known and can be used.

EXAMPLES

Example 1

In vitro transfection was performed in an A549 cell line to determine siRNA knockdown efficacy. Dose dependent knockdown for GST-π mRNA was observed with siRNAs as shown in Table 3.

TABLE 3

Dose dependent knockdown for GST-π mRNA in an A549 cell line

| siRNA | IC50 (pM) |
|---|---|
| A9 | 27, 29 |
| B2 | 121 |
| B3 | 235 |
| B4 | 229 |
| B13 | 23, 34 |
| BU02 | 21, 25, 34 |

Example 2

Protocol for in vitro knockdown.

One day before the transfection, plate the cells in a 96-well plate at 2×103 cells per well with 100 µl of DMEM (HyClone Cat. #SH30243.01) containing 10% FBS and culture in a 37° C. incubator containing a humidified atmosphere of 5% CO2 in air. Before transfection, change medium to 90 µl of Opti-MEM I Reduced Serum Medium (Life Technologies Cat. #31985-070) containing 2% FBS. Mix 0.2 µl of Lipofectamine RNAiMax (Life Technologies Cat. #13778-100) with 4.8 µl of Opti-MEM I for 5 minutes at room temperature. Mix 1 µl of siRNA with 4 µl of Opti-MEM I and combine with the LF2000 solution and then mix gently, without vortex. Wait for 5 minutes at room temperature. Incubate the mixture for 10 minutes at room temperature to allow the RNA-RNAiMax complexes to form. Add the 10 µl of RNA-RNAiMax complexes to a well and shake the plate gently by hand. Incubate the cells in a 37° C. incubator containing a humidified atmosphere of 5% CO2 in air for 2 hours. Change medium to fresh-MEM I Reduced Serum Medium (Life Technologies Cat. #31985-070) containing 2% FBS. 24 hours after transfection, wash the cells with ice-cold PBS once. Lyse the cells with 50 µl of Cell-to-Ct Lysis Buffer (Life Technologies Cat. #4391851 C) for 5-30 minutes at room temperature. Add 5 µl of Stop Solution and incubate for 2 minutes at room temperature. Measure mRNA level by RT-qPCR with TAQMAN immediately. Alternatively, the samples can be frozen at −80° C. and assayed at a later time.

Example 3

FIG. 2 shows in vivo knockdown efficacy for GST-π siRNA. Dose dependent knockdown of GST-π mRNA was observed in vivo with BU02 siRNA targeted to GST-π, as shown in FIG. 2.

Example 4

Figure 3:
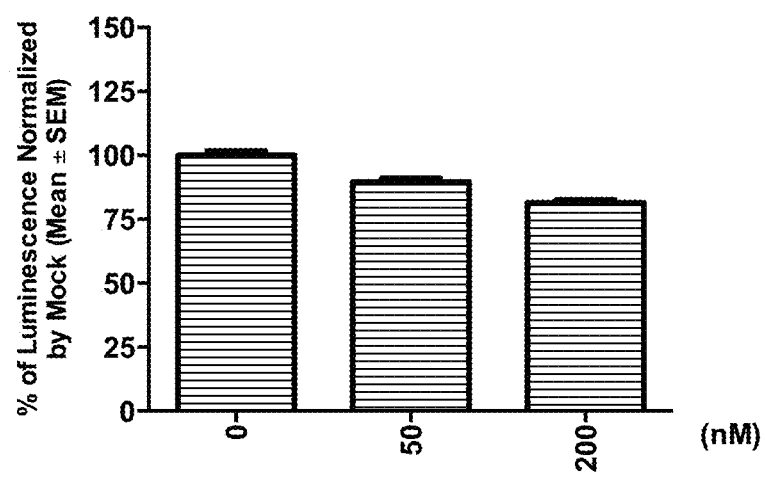
FIG. 3 shows inhibition of proliferation by GST-π siRNA. Dose-dependent inhibition of proliferation was observed in an A549 cell line in vitro with siRNA targeted to GST-π, as shown in FIG. 3.

FIG. 3 shows inhibition of cell proliferation by GST-π targeted siRNA. Dose-dependent inhibition of proliferation was observed in an A549 cell line in vitro with siRNA targeted to GST-π, as shown in FIG. 3.

Example 5

Figure 4:
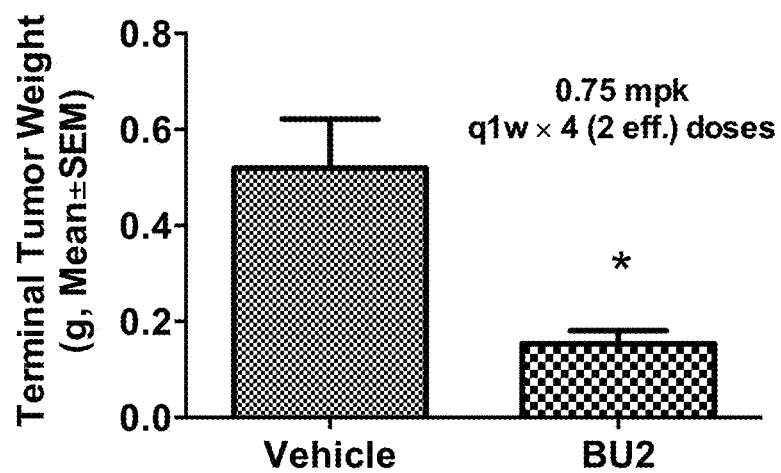
FIG. 4 shows tumor inhibition efficacy for GST-π siRNA. A pancreatic cancer xenograft model was utilized with a relatively low dose at 0.75 mg/kg of siRNA targeted to GST-π. The GST-π siRNA demonstrated significant tumor inhibition efficacy.

FIG. 4 shows tumor inhibition efficacy for GST-π siRNA (BU02). A pancreatic cancer xenograft model was utilized with a relatively low dose at 0.75 mg/kg of siRNA targeted to GST-π. The GST-π siRNA demonstrated significant and unexpectedly advantageous tumor inhibition efficacy at day 28.

In this experiment, A549 and PANC-1 cell lines were obtained from ATCC. The cell suspension was mixed well with ice thawed BD matrigel at 1:1 ratio for injection. Each mouse, athymic nude female mice, 6 to 8 weeks, Charles River, was inoculated subcutaneously in the right flank with 0.1 ml of an inoculum of $2\times10^6$ (A549) or $2.5\times10^6$ (PANC-1) cells using a 25 G needle and syringe (1 inoculum per mouse). Mice were anesthetized for inoculation. On the day when the established tumors reached approximately 250-350 mm$^3$ (A549) or 150-250 mm$^3$ (PANC-1) animals were subjected to bolus injection through tail vein. Animals were sacrificed by overdosed $CO_2$ and tumors dissected at different time points following the dosing. Tumors were first wet weighted, and then separated into three parts for measurement of GST-π knockdown, biodistribution of siRNA, and biomarker analysis. The samples were snap frozen in liquid nitrogen and stored at $-80°$ C. until ready to be processed for bioanalysis.

Example 6: Orthotopic A549 Lung Cancer Mouse Model

The GST-π siRNAs of this invention can exhibit profound reduction of orthotopic lung cancer tumors in vivo. In this example, a GST-π siRNA provided gene knockdown potency in vivo when administered in a liposomal formulation to the orthotopic lung cancer tumors in athymic nude mice.

In general, an orthotopic tumor model can exhibit direct clinical relevance for drug efficacy and potency, as well as improved predictive ability. In the orthotopic tumor model, tumor cells are implanted directly into the same kind of organ from which the cells originated.

The anti-tumor efficacy of the siRNA formulation against human lung cancer A549 was evaluated by comparing the final primary tumor weights measured at necropsy for the treatment group and the vehicle control group.

Orthotopic lung cancer tumor inhibition was observed in vivo for a GST-π siRNA based on structure BU2 (SEQ ID NOs:1276 and 1341). An orthotopic A549 lung cancer mouse model was utilized with a relatively low dose at 2 mg/kg of the siRNA targeted to GST-π.

The GST-π siRNA showed significant and unexpectedly advantageous lung tumor inhibition efficacy in this six-week study. After 43 days, the GST-π siRNA showed markedly advantageous tumor inhibition efficacy, with final tumor average weights significantly reduced by 2.8-fold as compared to control.

For this study, male NCr nu/nu mice, 5-6 weeks old, were used. The experimental animals were maintained in a HEPA filtered environment during the experimental period. The siRNA formulations were stored at 4° C. before use, and warmed to room temperature 10 minutes prior to injection in mouse.

For this A549 human lung cancer orthotopic model, on the day of surgical orthotopic implantation (SOI), the stock tumors were harvested from the subcutaneous site of animals bearing A549 tumor xenograft and placed in RPMI-1640 medium. Necrotic tissues were removed and viable tissues were cut into 1.5-2 mm$^3$ pieces. The animals were anesthetized with isoflurane inhalation and the surgical area was sterilized with iodine and alcohol. A transverse incision approximately 1.5 cm long was made in the left chest wall of the mouse using a pair of surgical scissors. An intercostal incision was made between the third and the fourth rib and the left lung was exposed. One A549 tumor fragment was transplanted to the surface of the lung with an 8-0 surgical suture (nylon). The chest wall was closed with a 6-0 surgical suture (silk). The lung was re-inflated by intrathoracic puncture using a 3 cc syringe with a 25 G×1½ needle to draw out the remaining air in the chest cavity. The chest wall was closed with a 6-0 surgical silk suture. All procedures of the operation described above were performed with a 7× magnification microscope under HEPA filtered laminar flow hoods.

Three days after tumor implantation, the model tumor-bearing mice were randomly divided into groups of ten mice per group. For the group of interest, treatment of the ten mice was initiated three days after tumor implantation.

For the group of interest, the formulation was (Ionizable lipid:cholesterol:DOPE:DOPC:DPPE-PEG-2K:DSPE-PEG-2K), a liposomal composition. The liposomes encapsulated the GST-π siRNA.

For the study endpoint, the experimental mice were sacrificed forty-two days after treatment initiation. Primary tumors were excised and weighed on an electronic balance for subsequent analysis.

For an estimation of compound toxicity, the mean body weight of the mice in the treated and control groups was maintained within the normal range during the entire experimental period. Other symptoms of toxicity were not observed in the mice.

Example 7

Effect of small interfering RNA (siRNA) targeting GST-π on A549 cell growth in nude mice and angiogenesis on chorioallantoic membrane (CAM) assay. Three pairs of GST-π siRNA-plasmid and non-silencing-plasmid are constructed, and transfected into A549 cells through LIPO-FECTAMINE 2000, respectively. The most effective pair of GST-π siRNA-plasmid is selected by ELISA and real-time RT-PCR. A549 cells are transfected with selected GST-π siRNA-plasmid, A549 cells are transfected with non-silencing-plasmid, and A549 cells without transfection are inoculated into nude mice, respectively. Chick embryos are randomly divided into four groups and CAM is treated by different solutions for 48 h: culture media DMEM as negative control group, un-transfected A549 cell culture supernatants as positive control group, GST-π siRNA A549 cell culture supernatants as GST-π siRNA group and non-silencing siRNA A549 cell culture supernatants as non-silencing siRNA group. The CAMs were harvested on day 12 for microscopic assays.

Compared with control group, GST-π siRNA-plasmid induces reduction in GST-π secretion by A549 cells accompanied by reduction in GST-π mRNA. Compared with non-silencing siRNA group, the mean tumor volume of murine xenograft is reduced in GST-π siRNA group; time for xenografts growing to 50 mm³ is delayed. GST-π contents in xenograft are reduced. In CAM assays, GST-π content is zero in negative group, and in GST-π siRNA group is reduced by 20-70% compared to non-silencing siRNA group or positive group; vessels branch points of CAM in GST-π siRNA group or non-silencing siRNA group or positive group are increased compared with negative group; total vessel length of CAM in GST-π siRNA group is increased compared with negative group, while in non-silencing siRNA group or positive group it is increased. Compared with negative control group, the proliferation of microvessels is increased when cell culture supernatant with GST-π is added in GST-π siRNA group, significant proliferated vessels are observed in non-silencing siRNA group or positive group.

Example 8

Cell culture. The human non-small cell lung carcinoma cell line, A549 is cultured in F-12K medium (ATCC) supplemented with 10% FBS (FBS, Invitrogen) at 37° C. in a humidified atmosphere with 5% $CO_2$. The cells stably expressing control, or GSTπ siRNAs are generated by transducing A549TR cells with the respective lentiviral transduction particles as per manufacturer's instructions (Sigma-Aldrich). Resistant clones are selected in 2.5 μg/mL puromycin (Invivogen) for 12 d, isolated using cloning cylinders, and subsequently expanded and maintained in puromycin-containing medium.

Example 9

GST-π targeted siRNA results in profound regression of tumor volume in vivo.

A lipid formulation is used to encapsulate and deliver siRNA in nanoparticles to xenografts of human A549 lung cancer cells in scid mice. The xenografts are tested to identify the presence of KRAS mutations or aberrant levels of expression compared to normal cells. When tumors became established (>100 mm³), mice are treated with either GST-π targeted siRNA or Control (non-specific) siRNA every 2 days for 2 weeks. The trial is halted when the control group has to be euthanized.

Results: Treatment with GST-π targeted siRNA prevents tumor expansion and results in dramatic tumor volume reduction.

The tumors that are recovered are sectioned and visualized by TUNEL staining. GST-π targeted siRNA-treated tumors display significantly higher levels of apoptosis. RNA is extracted from the tumors, and real-time PCR is performed to examine specific knockdown of GST-π.

Results: Treatment with GST-π targeted siRNA dramatically reduces expression of GST-π in vivo.

Example 10

The GST-π siRNAs of this invention exhibited increased serum stability.

A GST-π siRNA was incubated in human serum and detection of remaining siRNA at various time points was done by HPLS/LCMS. The half-life ($t_{1/2}$) in serum for both the sense strand and antisense strand of the GST-π siRNA (SEQ ID Nos:1276 and 1341) was about 100 minutes.

Example 11

The GST-π siRNAs of this invention exhibited enhanced stability in formulation in plasma.

A GST-π siRNA was incubated in a formulation in plasma and detection of remaining siRNA was done at various time points. The half-life ($t_{1/4}$) in plasma of a formulation of GST-π siRNA (SEQ ID Nos:1276 and 1341) was significantly longer than 100 hours.

The GST-π siRNA was prepared in a liposomal formulation having the composition (Ionizing lipid:cholesterol:DOPE:DOPC:DPPE-PEG-2K) (25:30:20:20:5). The z-average size for the liposomal nanoparticles was 40.0 nm, and the siRNA was 91% encapsulated.

The formulation was incubated in 50% human serum in PBS for 40 min, 1.5 h, 3 h, 24 h, and 96 h. The amount of the GST-π siRNA was determined by an ELISA-based assay.

Example 12

The GST-π siRNAs of this invention can exhibit profound reduction of cancer xenograft tumors in vivo. The GST-π siRNAs can provide gene knockdown potency in vivo when administered in a liposomal formulation to the cancer xenograft tumors.

Tumor inhibition efficacy was observed for a GST-π siRNA (SEQ ID NOs:1276 and 1341). Dose dependent knockdown of GST-π mRNA was observed in vivo with the siRNA targeted to GST-π. A cancer xenograft model was utilized with a siRNA targeted to GST-π.

The GST-π siRNA showed significant and unexpectedly advantageous tumor inhibition efficacy within a few days after administration. Treatment with a GST-π siRNA resulted in significant reduction of GST-π mRNA expression 4 days after injection in a lipid formulation. At the higher dose of 4 mg/kg, significant reduction of about 40% was detected 24 hours after injection.

The GST-π siRNA was administered in a single injection of 10 mL/kg of a liposomal formulation having the composition (Ionizable lipid:Cholesterol:DOPE:DOPC:DPPE-PEG-2K) (25:30:20:20:5).

For the cancer xenograft model, an A549 cell line was obtained from ATCC. The cells were maintained in RPMI-1640 supplemented with 10% Fetal Bovine Serum and 100 U/ml penicillin and 100 μg/ml streptomycin. Cells were split 48 hrs before inoculation so that cells were in log phase growth when harvested. Cells were lightly trypsinized with trypsin-EDTA and harvested from tissue culture. The number of viable cells was counted and determined in a hemocytometer in the presence of trypan blue (only viable cells are counted). The cells were resuspended to a concentration of 4×10⁷/ml in RPMI media without serum. Then the cell suspension was mixed well with ice thawed BD matrigel at 1:1 ratio for injection.

Mice were Charles River Laboratory Athymic Nude (nu/nu) Female Mice, immuno-compromised, 6-8 weeks old, 3 mice per group.

For tumor model preparation, each mouse was inoculated subcutaneously in the right flank with 0.1 ml an inoculum of 2×10⁶ of A549 cells using a 25 G needle and syringe, one inoculum per mouse. Mice were not anesthetized for inoculation.

For tumor volume measurements and randomization, tumor size was measured to the nearest 0.1 mm. Tumor volumes were calculated using the formula: Tumor volume=length×width²/2. Tumor volumes were monitored twice a week. Once the established tumors reached approximately 350-600 mm³, the mice were assigned into groups with varied time points. On the same day, test articles were administered according to the dosing regimen.

For dosage administration, on the day when the established tumors reached approximately 350-600 mm$^3$, the test articles were taken out from 4° C. fridge. Before being applied to syringes, the bottle containing formulation was reverted by hand for a few times to make a homogeneous solution.

For body weight, mice were weighed to the nearest 0.1 g. Body weights were monitored and recorded twice for weeks, for the rest of weeks, including the day of study termination.

For tumors collection, animals were sacrificed by overdosed $CO_2$ and tumors were dissected at 0, 24, 48, 72, 96 (optional), and 168 hours following the dosing. Tumors were first wet weighted, and then separated into three parts for KD, distribution and biomarker analysis. The samples were snap frozen in liquid nitrogen and stored at −80° C. until ready to be processed.

The embodiments described herein are not limiting and one skilled in the art can readily appreciate that specific combinations of the modifications described herein can be tested without undue experimentation toward identifying nucleic acid molecules with improved RNAi activity.

All publications, patents and literature specifically mentioned herein are incorporated by reference in their entirety for all purposes.

It is understood that this invention is not limited to the particular methodology, protocols, materials, and reagents described, as these may vary. It is also to be understood that the terminology used herein is for the purpose of describing particular embodiments only, and is not intended to limit the scope of the present invention. It will be readily apparent to one skilled in the art that varying substitutions and modifications can be made to the description disclosed herein without departing from the scope and spirit of the description, and that those embodiments are within the scope of this description and the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprises," "comprising", "containing," "including", and "having" can be used interchangeably, and shall be read expansively and without limitation.

Recitation of ranges of values herein are merely intended to serve as a shorthand method of referring individually to each separate value falling within the range, unless otherwise indicated herein, and each separate value is incorporated into the specification as if it were individually recited herein. For Markush groups, those skilled in the art will recognize that this description includes the individual members, as well as subgroups of the members of the Markush group.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever.

All of the features disclosed in this specification may be combined in any combination. Each feature disclosed in this specification may be replaced by an alternative feature serving the same, equivalent, or similar purpose.

What is claimed is:

1. A nucleic acid molecule, wherein:
the molecule has a polynucleotide sense strand and a polynucleotide antisense strand;
wherein a contiguous region of the antisense strand is complementary to a sequence of an mRNA encoding GST-π; and
wherein the antisense strand is UAGGGUCU-CAAAAGGCUUCag (SEQ ID NO:1341), and the sense strand is GAAGCCUUUUGAGACCCUAtt (SEQ ID NO:1276); or wherein the antisense strand is ACAGCAGGGUCUCAAAAGGct (SEQ ID NO:1305), and the sense strand is CCUUUUGAGAC-CCUGCUGUtt (SEQ ID NO:1240)
wherein upper case letters refer to ribonucleotides and lower case letters refer to deoxyribonucleotides.

2. The nucleic acid molecule of claim 1, wherein the polynucleotide sense strand and the polynucleotide antisense strand are connected as a single strand, and form a duplex region connected at one end by a loop.

3. The nucleic acid molecule of claim 1, wherein the molecule is an RNAi molecule active for gene silencing.

4. The nucleic acid molecule of claim 1, wherein the molecule is active for inhibiting expression of GST-π.

5. The nucleic acid molecule of claim 1, wherein the molecule has an IC50 for knockdown of GST-π in A549 cells of less than 100 pM.

6. A composition comprising one or more nucleic acid molecules of claim 1 and a pharmaceutically acceptable carrier.

7. The composition of claim 6, wherein the carrier is a lipid molecule or liposome.

8. A method for treating pancreatic cancer or lung cancer, the method comprising administering to a subject in need a composition of claim 6.

9. The method of claim 8, wherein the disease is pancreatic cancer.

10. The nucleic acid molecule of claim 1, wherein at least one or more nucleotides in any strand is chemically modified.

* * * * *